US009074225B2

(12) United States Patent
Ridley et al.

(10) Patent No.: US 9,074,225 B2
(45) Date of Patent: Jul. 7, 2015

(54) BIOSYNTHESIS OF 1-ALKENES IN ENGINEERED MICROORGANISMS

(75) Inventors: Christian Perry Ridley, Acton, MA (US); Nikos Basil Reppas, Brookline, MA (US)

(73) Assignee: Joule Unlimited Technologies, Inc., Bedford, MA (US)

( * ) Notice: Subject to any disclaimer, the term of this patent is extended or adjusted under 35 U.S.C. 154(b) by 20 days.

(21) Appl. No.: 12/821,107

(22) Filed: Jun. 22, 2010

(65) Prior Publication Data
US 2010/0330642 A1 Dec. 30, 2010

Related U.S. Application Data

(60) Provisional application No. 61/219,369, filed on Jun. 22, 2009.

(51) Int. Cl.
*C12P 5/02* (2006.01)
*C12N 9/12* (2006.01)
*C12N 1/12* (2006.01)
*C12N 9/10* (2006.01)

(52) U.S. Cl.
CPC . *C12P 5/026* (2013.01); *C12N 1/12* (2013.01); *C12N 9/1029* (2013.01)

(58) Field of Classification Search
CPC .............................. C12P 5/026; C12N 9/1029
USPC ............................................... 435/167, 252.3
See application file for complete search history.

(56) References Cited

U.S. PATENT DOCUMENTS

| | | | |
|---|---|---|---|
| 5,059,532 A | 10/1991 | Kimura et al. | |
| 6,951,729 B1 | 10/2005 | Dewolf, Jr. et al. | |
| 2009/0139134 A1* | 6/2009 | Yoshikuni et al. | 44/307 |
| 2010/0330642 A1 | 12/2010 | Ridley et al. | |
| 2011/0091952 A1 | 4/2011 | Sherman et al. | |
| 2012/0208253 A1 | 8/2012 | Ridley | |

FOREIGN PATENT DOCUMENTS

| | | |
|---|---|---|
| WO | WO 2008/119134 A1 | 10/2008 |
| WO | WO/2009/062190 | 5/2009 |
| WO | WO/2009/111513 | 9/2009 |
| WO | WO 2010/044960 A1 | 4/2010 |
| WO | WO 2011/011689 | 1/2011 |
| WO | WO 2012/050931 | 4/2012 |

OTHER PUBLICATIONS

Witkowski et al. Biochemistry. Sep. 7, 1999; 38(36): 11643-50.*
Mendez-Perez, D. et al., "A Gene Encoding a Modular Synthase is Involved in α-olefin Biosynthese in *Synechococcus*sp. PCC7002," *Appl. Environ. Microbiol.*, Apr. 29, 2011, 20 pages. doi: 10.1128/AEM.00467-11.
Gehret, J. et al., "Terminal Alkene Formation by the Thioesterase of Curacin a Biosynthesis: Structure of a Decarboxylating Thioesterase," *JBC Papers in Press*, Feb. 27, 2011, nineteen pages. [Online] [Retrieved Apr. 18, 2011] Retrieved from the Internet <URL:http://www.jbc.org/cgi/doi/10.1074/jbc.M110.214635>.
Arora, P., et al., "Mechanistic and Functional Insights into Fatty Acid Activation in Mycobacterium Tuberculosis," *Nature Chemical Biology*, 2009, pp. 166-173, vol. 5, No. 3.
Goodloe, R.S., et al., "Structure and Composition of Hydrocarbons and Fatty Acids from a Marine Blue-Green Alga, *Synechococcus* sp.," *Biochimica et Biophysica Acta*, 1982, pp. 485-492, vol. 710.
Gu, L. et al., "Polyketide Decarboxylative Chain Termination Preceded by O-Sulfonation in Curacin a Biosynthesis," *Journal of the American Chemical Society*, 2009, pp. 16033-16035, vol. 131, No. 44.
Hansen, D.B. et al., "The Loading Module of Mycosubtilin: An Adenylation Domain with Fatty Acid Selectivity," *Journal of the American Chemical Society*, 2007, pp. 6366-6367, vol. 129.
Higashi, S. et al., "An in Vivo Study of Substrate Specificities of Acyl-lipid Desaturases and Acyltransferases in Lipid Synthesis in *Synechocystis* PCC6803," *Plant Physiology*, 1993, pp. 1275-1278, vol. 102.
Kaczmarzyk, D. et al., "Fatty Acid Activation in Cyanobacteria Mediated by Acyl-Acyl Carrier Protein Synthetase Enables Fatty Acid Recycling," *Plant Physiology*, 2010, pp. 1598-1610, vol. 152.
Koketsu, K. et al., "Reconstruction of the Saframycin Core Scaffold Defines Dual Pictet-Spengler Mechanisms," *Nature Chemical Biology*, 2010, pp. 408-410, vol. 6.
Kopp, F. et al., "Harnessing the Chemical Activation Inherent to Carrier Protein-Bound Thioesters for the Characterization of Lipopeptide Fatty Acid Tailoring Enzymes," *Journal of the American Chemical Society*, 2008, pp. 2656-2666, vol. 130.
Li, L. et al., "Characterization of the Saframycin a Gene Cluster from *Streptomyces lavendulae* NRRL 11002 Revealing a Nonribosomal Peptide Synthetase System for Assembling the Unusual Tetrapeptidyl Skeleton in an Iterative Manner," *Journal of Bacteriology*, 2008, pp. 251-263, vol. 190.
Li, T. et al., "Synechococcus sp. PCC 7002, Complete Genome: GenBank: CP000951.1. Region: 1205897-1214059," Mar. 14, 2008, four pages [Online] [Retrieved Dec. 1, 2010] Retrieved from the Internet <Url:http://www.ncbi.nlm.nih.gov/nuccore/169884305?from=1205897&to=1214059 &report=gbwithparts.>.
Lin, J.-W. et al., "Nucleotide Sequence and Functional Analysis of the *luxE* Gene Encoding Acyl-Protein Synthetase of the *lux* Operon from *Photobacterium leiognathi*," *Biochemical and Biophysical Research Communications*, 1996, pp. 764-773, vol. 228.
Moore, B. et al., "Biosynthesis and Attachment of Novel Polyketide Synthase Starter Units," *Natural Product Reports*, 2002, pp. 70-99, vol. 19.
Murata, N. et al. "Modes of Fatty-Acid Desaturation in Cyanobacteria," *Plant Cell Physiology*, 1992, pp. 933-941, vol. 33.
PCT International Search Report and Written Opinion, PCT Application No. PCT/US2010/039558, Oct. 6, 2010, eight pages.
Williams, J.P. et al., "The Manipulation of the Fatty Acid Composition of Glycerolipids in Cyanobacteria Using Exogenous Fatty Acids," *Plant Cell Physiology*, 1990, pp. 495-503, vol. 31.
Winters, K. et al., "Hydrocarbons of Blue-Green Algae: Geochemical Significance," Science, 1969, pp. 467-468, vol. 163.

(Continued)

*Primary Examiner* — Tekchand Saidha
*Assistant Examiner* — Md. Younus Meah
(74) *Attorney, Agent, or Firm* — Fenwick & West LLP; Chang B. Hong

(57) ABSTRACT

Various 1-alkenes, including 1-nonadecene and 1-octadecene, are synthesized by the engineered microorganisms and methods of the invention. In certain embodiments, the microorganisms comprise recombinant 1-alkene synthases. The engineered microorganisms may be photosynthetic microorganisms such as cyanobacteria.

18 Claims, 7 Drawing Sheets

(56) References Cited

OTHER PUBLICATIONS

Figure 1:
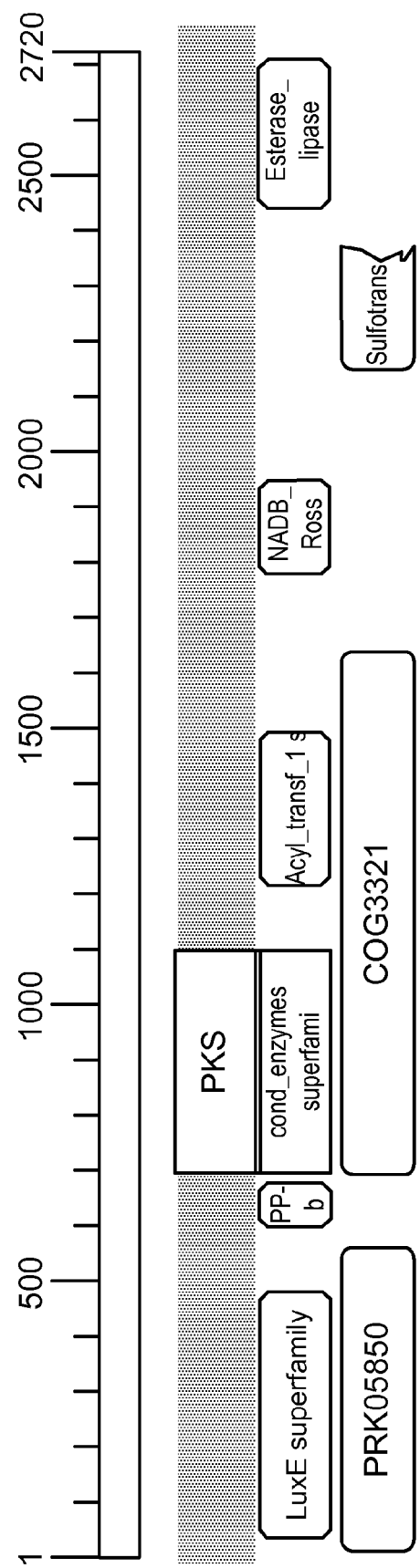

Wittman, M. et al., "Role of DptE and DptF in the Lipidation Reaction of Daptomycin," *FEBS Journal*, 2008, pp. 5343-5354, vol. 275.

Wyckoff, T.J.O. et al., "Hydrocarbon Rulers in UDP-N-acetylglucosamine acyltransferases," *The Journal of Biological Chemistry*, 1998, pp. 32369-32372, vol. 273.

Yuan, L. et al., "Modification of the Substrate Specificity of an Acyl-Acyl Carrier Protein Thioesterase by Protein Engineering," *Proceedings of the National Academy of Sciences USA*, 1995, pp. 10639-10643, vol. 92.

European Patent Office, European Search Report and Opinion, European Patent Application No. 10797586.4, Nov. 7, 2013, ten pages.

Li, T. et al., "Polyketide synthase; Synechococcus sp. (strain ATCC 27264/PCC 7002/PR-6) (Agmenellum quadruplicatum)," May 20, 2008, Database UniProtKB/TrEMBL, Database Accession No. B1XKC6, three pages. [Online] [Retrieved Oct. 25, 2013] Retrieved from the Internet <URL:http://www.ebi.ac.uk/Tools/dbfetch/dbfetch?db=uniprot&id=B1XKC6.>.

Mendez-Perez, D. et al., "Modular Synthase-Encoding Gene Involved in α-Olefin Biosynthesis in Synechococcus sp. Strain PCC 7002," *Applied and Environmental Microbiology*, Jun. 2011, pp. 4264-4267, vol. 77, No. 12.

Pfeifer, B. et al., "Biosynthesis of Polyketides in Heterologous Hosts," *Micriobiology and Molecular Biology Reviews*, Mar. 2001, pp. 106-118, vol. 65, No. 1.

State Intellectual Property Office of the People's Republic of China, Second Office Action, Chinese Patent Application No. 201080037536.0, Jul. 7, 2014, fifteen pages.

Mexican Patent Office, Office Action, Mexican Patent Application No. 12/000170, Jun. 5, 2014, four pages.

Li, T. et al., Polyketide synthase [Synechococcus sp. PCC 7002], NCBI Reference Sequence No.YP_001734428.1, GenBank, Jul. 17, 2008, three pages. [Online] [Retrieved Oct. 9, 2012] Retrieved from the Internet <URL:http://www.ncbi.nlm.nih.gov/protein/170077790?sat=13&satkey+668363.>.

Eurasian Patent Office, Official Action, Eurasian Patent Application No. 201270058, Sep. 9, 2013, five pages.

State Intellectual Property Office of the People's Republic of China, First Office Action, Chinese Patent Application No. 201080037536.0, Aug. 21, 2013, twenty pages.

Eurasian Patent Office, Office Action, Eurasian Patent Application No. 201270058, Sep. 8, 2014 four pages.

Israeli Patent Office, Office Action, Israeli Patent Application No. 217015, Jul. 31, 2014, seven pages.

Albro, P.W. et al., "Confirmation of the Identification of the Major C-29 Hydrocarbons of *Sarcina lutea*," Journal of Bateriology, Oct. 1971, pp. 213-218, vol. 108, No. 1.

Beller, H.R. et al., "Genes Involved in Long-Chain Alkene Biosynthesis in *Micrococcus luteus* " Applied and Environmental Microbiology, Feb 2010, (ePub Dec. 28, 2009), pp. 1212-1223, vol. 76, No. 4.

Genbank. CP000951 Region: 1214256-1215155 [online] Mar. 14, 2008, 2 pages, Available on the Internet: <URL:http://www.ncbi.nlm.nih.gov/nuccore/169884305?from=1214256&to=1215155&report=gbwithparts>.

PCT ISR and Written Opinion, PCT Application No. PCT/US2011/058411, Mar. 16, 2012, 18 pages.

Beluzic, R. et al., "A single mutation at Tyr$^{143}$ of human S-adenosylhomocysteine hydrolase renders the enzyme thermosensitive and affects the oxidation state of bound cofactor nicotinamide-adenine dinucleotide," *Biochemical Journal*, 2006, pp. 245-253.

Mexican Intellectual Property Office, Office Action, Mexican Patent Application No. 2012/000170, Oct. 23, 2014, ten pages.

State Intellectual Property Office of the People's Republic of China, Third Office Action, Chinese Patent Application No. 201080037536.0, Mar. 25, 2015, seven pages.

* cited by examiner

US 9,074,225 B2

BIOSYNTHESIS OF 1-ALKENES IN ENGINEERED MICROORGANISMS

CROSS-REFERENCE TO RELATED APPLICATIONS

This application claims priority to earlier filed U.S. Provisional Patent Application No. 61/219,369, filed Jun. 22, 2009, the disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 3, 2010, is named "17030 Sequence Listing.txt" and is 107,356 bytes in size.

FIELD OF THE INVENTION

This invention generally relates to genes useful in producing carbon-based products of interest in host cells. The invention also relates to methods for producing fuels and chemicals through engineering metabolic pathways in photosynthetic and non-photosynthetic organisms.

BACKGROUND OF THE INVENTION

Unsaturated linear hydrocarbons such as α-olefins or 1-alkenes are an industrially important group of molecules which can serve as lubricants and surfactants in addition to being used in fuels. The biosynthesis of organic chemicals can provide an efficient alternative to chemical synthesis. Thus, a need exists for microbial strains which can make increased yields of hydrocarbons, particularly terminal alkenes.

SUMMARY OF THE INVENTION

The invention relates to a metabolic system and methods employing such systems in the production of fuels and chemicals. Various microorganisms are genetically engineered to increase 1-alkene synthase activity for the production of alkenes (also referred to as olefins), particularly 1-alkenes, including 1-nonadecene and 1-octadecene.

The invention provides isolated polynucleotides comprising or consisting of nucleic acid sequences selected from the group consisting of coding sequences for a 1-alkene synthase and/or an A1174 hydrolase, expression optimized variants for these nucleic acid sequences and related nucleic acid sequences and fragments. The invention also provides vectors and host cells comprising the isolated polynucleotides.

The invention further provides isolated polypeptides comprising or consisting of polypeptide sequences selected from the group consisting of sequences encoded by a 1-alkene synthase gene, and related polypeptide sequences, fragments and fusions. The invention also provides isolated polypeptides comprising or consisting of polypeptide sequences selected from the group consisting of sequences encoded by an A1174 hydrolase gene, and related polypeptide sequences, fragment and fusions. Antibodies that specifically bind to the isolated polypeptides are also provided.

The invention also provides methods for expressing in a host cell a heterologous nucleic acid sequence encoding improved 1-alkene synthase activity in a 1-alkene biosynthetic pathway.

The invention also provides a coding sequence of a 1-alkene synthase activity, a nucleic acid sequence that is an expression optimized coding sequence of a 1-alkene synthase activity gene and related nucleic acid sequences and fragments. Likewise, the invention provides a coding sequence of an A1174 hydrolase activity and related nucleic acid sequences and fragments.

The invention described herein provides a gene which can be over-expressed in a range of organisms and which encodes an enzyme involved in the synthesis of 1-alkenes and other carbon-based products of interest. Over-expression of the gene can be used in combination with other genes to achieve high levels of 1-alkene production. Organisms such as a recombinant or photosynthetic bacterium (for example, cyanobacteria) can be genetically modified to optimize production of 1-alkenes using light, water and carbon dioxide. Alternatively, microorganisms can be engineered to produce 1-alkenes directly or indirectly from exogenously added carbon substrates.

In one embodiment, the invention provides an isolated or recombinant polynucleotide comprising or consisting of a nucleic acid sequence selected from the group consisting of: SEQ ID NO:1 or SEQ ID NO:3; a nucleic acid sequence that is a degenerate variant of SEQ ID NO:1 or SEQ ID NO:3; a nucleic acid sequence at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 90%, at least 95%, at least 96%, at least 97%, at least 98%, at least 99%, or at least 99.5% identical to SEQ ID NO:1 or SEQ ID NO:3; a nucleic acid sequence that encodes a polypeptide having the amino acid sequence of SEQ ID NO:2 or SEQ ID NO:4; a nucleic acid sequence that encodes a polypeptide at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO:2 or SEQ ID NO:4; and a nucleic acid sequence that hybridizes under stringent conditions to SEQ ID NO:1 or SEQ ID NO:3.

In another embodiment, the invention provides the isolated or recombinant polynucleotide of the previous paragraph, wherein the nucleic acid sequence encodes a polypeptide having 1-alkene synthase activity. In yet another embodiment, the isolated or recombinant polynucleotide encodes a polypeptide having an A1174 hydrolase activity. In yet another embodiment, the invention provides the isolated polynucleotide of the previous paragraph, wherein the nucleic acid sequence and the sequence of interest are operably linked to one or more expression control sequences. In another embodiment, the invention provides a vector comprising one of the polynucleotides in the previous paragraph. In yet another embodiment, the invention provides a host cell comprising a recombinant or isolated polynucleotide described in the previous paragraph. In a related embodiment, the host cell is selected from the group consisting of prokaryotes, eukaryotes, yeasts, filamentous fungi, protozoa, algae and synthetic cells. In yet another embodiment, the host cell produces carbon-based products of interest. In still another embodiment, the invention provides an isolated antibody or antigen-binding fragment or derivative thereof which binds selectively to one of the isolated polypeptides of the previous paragraph.

The invention also provides a method of genetically engineering an organism to increase expression of a 1-alkene synthase, comprising modifying the promoter of an endogenous 1-alkene synthase, recombinantly expressing an endogenous 1-alkene synthase in said organism, or by increasing read-through of a promoter upstream of the promoter for the organism's endogenous 1-alkene synthase by, e.g., removing the structural gene encoded by the upstream promoter.

The invention also provides a method for identifying a modified gene that improves 1-alkene synthesis by a microorganism, comprising: modifying a gene encoding a 1-alkene synthase by employing rational design, error prone PCR, site-directed mutagenesis, whole gene site saturation mutagenesis, site-directed site saturation mutagenesis, gene shuffling or correlated site saturation mutagenesis; expressing the modified synthase gene in a host cell; and screening the host cell for increased 1-alkene synthase activity (e.g., measuring increased production of 1-nonadecene or another 1-alkene of interest). In yet another embodiment, the invention provides improved enzymes identified by the aforementioned method, wherein said enzyme is characterized by improved substrate affinity, substrate catalytic conversion rate, improved thermostability, activity at a different pH, or optimized codon usage for improved expression in a host cell. In yet another embodiment, the invention provides nucleic acids encoded the aforementioned 1-alkene synthases, wherein said nucleic acid is characterized by, e.g., increased stability and/or expression when expressed in a transformed microorganism.

In yet another embodiment, the invention provides a method for the biosynthetic production of 1-alkenes, comprising: culturing an engineered microorganism in a culture medium, wherein said engineered microorganism comprises a recombinant 1-alkene synthase, and wherein said engineered microorganism produces 1-alkenes, and wherein the amount of said 1-alkenes produced by said engineered microorganism is greater than the amount that would be produced by an otherwise identical microorganism, cultured under identical conditions, but lacking said recombinant 1-alkene synthase. In a related embodiment, the amount of 1-nonadecene produced is at least two times, at least three times, or between two and ten times the amount produced by an otherwise identical microorganism lacking said recombinant 1-alkene synthase. In another related embodiment, the amount of 1-nonadecene produced is at least 0.75% dry cell weight ("DCW"). In a related embodiment, the recombinant 1-alkene synthase is an endogenous 1-alkene synthase expressed, at least in part, from a promoter other than its native promoter. In yet another related embodiment, the recombinant 1-alkene synthase is a heterologous 1-alkene synthase. In yet another related embodiment, the recombinant 1-alkene synthase is expressed from a heterologous promoter. In yet another related embodiment, the 1-alkene synthase is endogenous to said microorganism but is recombinantly expressed from a heterologous promoter.

In another embodiment of the method for producing 1-alkenes, the engineered microorganism is a photosynthetic microorganism, wherein exposing said engineered microorganism to light and carbon dioxide results in the production of alkenes by said microorganism. In a related embodiment, the engineered microorganism is a cyanobacterium. In yet another embodiment of the method for producing 1-alkenes, the 1-alkenes are selected from the group consisting of 1-nonadecene and 1-octadecene. In yet another embodiment of the method, said 1-alkenes are isolated from said cyanobacterium or said culture medium. In yet another embodiment, exogenous fatty acids are added to said culture medium as a substrate for said recombinant 1-alkene synthase.

In another embodiment, the invention provides a method for the biosynthetic production of an olefin, comprising (1) culturing a cyanobacterium in a culture medium, wherein said cyanobacterium comprises a 1-alkene synthase activity, and wherein said culture medium comprises an exogenous fatty acid; and (2) exposing said engineered cyanobacterium to light and carbon dioxide, wherein said exposure results in the production of an olefin by said cyanobacterium, and wherein the amount of said olefin produced is greater than the amount that would be produced by an otherwise identical cyanobacterium, cultured under identical conditions but in the absence of said exogenous fatty acid. In a related embodiment, the concentration of exogenously added fatty acid in said culture medium is at least 1 µg/ml. In other related embodiments, the concentration is at least 10 µg/ml, at least 50 µg/ml, at least 100 µg/ml, at least 500 µg/ml, at least 1 mg/ml, at least 10 mg/ml, at least 50 mg/ml, at least 100 mg/ml, or at least 500 mg/ml or a range between any two of these concentrations (i.e., between 1 µg/ml and 500 mg/ml). In yet another related embodiment, the fatty acid is an odd-chain fatty acid, such as, e.g., tridecanoic acid. In yet another related embodiment, the fatty acid is tridecanoic acid and the olefin produced is 1-octadecene. In yet another related embodiment, the amount of said 1-octadecene produced is at least 0.01% dry cell weight ("DCW"), at least 0.039% dry cell weight, at least 0.05% dry cell weight, at least 0.1% dry cell weight. In yet another related embodiment, the amount of said 1-octadecene produced is between 0.3% dry cell weight and 1% dry cell weight. In yet another related embodiment, the % DCW of said 1-octadecene produced is at least half the % DCW of 1-nonadecene produced by the microorganism. In yet another related embodiment, the fatty acid is an even-chain fatty acid and the olefin produced is 1-nonadecene. In yet another related embodiment, the olefin produced is isolated from said cyanobacterium or said culture medium.

In yet another embodiment, the invention provides a method for the biosynthetic production of alkenes, comprising (1) culturing an engineered microorganism in a culture medium, wherein said engineered microorganism comprises a modification, wherein said modification reduces the activity of an A1174 hydrolase native to said cyanobacterium; and (2) exposing said engineered microorganism to light and carbon dioxide, wherein said exposure results in the production of alkenes by said engineered microorganisms, wherein said alkenes comprise 1-alkenes, and wherein the amount of 1-alkenes produced is greater than the amount that would be produced by an otherwise identical cyanobacterium, cultured under identical conditions, but lacking said modification. In a related embodiment, the 1-alkenes include 1-nonadecene. In yet another related embodiment, the microorganism is a cyanobacteria.

In yet another embodiment, the invention provides an engineered cyanobacterium, wherein said cyanobacterium comprises a mutation in an A1174 hydrolase, wherein the mutation reduces the activity of said hydrolase. In yet another embodiment, the mutation is a knockout mutation, e.g., a deletion of all or part of the structural gene encoding the A1174 hydrolase.

In yet another embodiment, the invention provides an engineered cell for the production of olefins, wherein said cell comprises a recombinant nonA gene, and wherein the activity of the protein encoded by said nonA gene is greater than the activity of said protein in an otherwise identical cell lacking said recombinant nonA gene. In a related embodiment, the recombinant nonA gene is a heterologous gene. In yet another related embodiment, the recombinant nonA gene comprises a recombinant promoter. In yet another related embodiment, the engineered cyanobacterium comprises a deletion of all or part of the structural gene encoding the A1174 hydrolase.

In yet another embodiment, the invention provides an engineered cyanobacterium, wherein said cyanobacterium comprises a nonA knockout.

In various related embodiments, the 1-alkene synthase in the methods and compositions recited above is at least 50%, at least 60%, at least 70%, at least 80%, at least 85%, at least 80%, or at least 95% identical to the 1-alkene synthase of SEQ ID NO:2, SEQ ID NO:8 or SEQ ID NO:9. In yet other embodiments, the 1-alkene synthase is identical to the 1-alkene synthase of SEQ ID NO:2, SEQ ID NO:8 or SEQ ID NO:9.

In various related embodiments, the microorganism in the methods and compositions recited above is *E. coli*. In other related embodiments, the microorganism is a species of *Synechococcus*. In still other related embodiments, the microorganism is *Synechococcus* sp. PCC 7002.

Additional information related to the invention may be found in the following Drawings and Detailed Description.

DRAWINGS

FIG. 1 shows a representation of the domains found in the 1-alkene synthase YP_001734428 (NonA), as identified by the conserved domain (CD) searching program available on the NCBI website. Abbreviations for domains: acyl-carrier protein (ACP); phosphopantetheinyl (PP); ketosynthase (KS); acyltransferase (AT); ketoreductase (KR); sulfotransferase (ST); and thioesterase (TE). By reference to the YP_001734428 gene sequence, the domains are located at the following residues: LuxE domain: 10-557; ACP domain: 598-675; KS domain: 693-1095; AT domain: 1216-1490; KR domain: 1777-1943; ST domain: 2145-2360; TE domain: 2449-2708.

Figure 2:
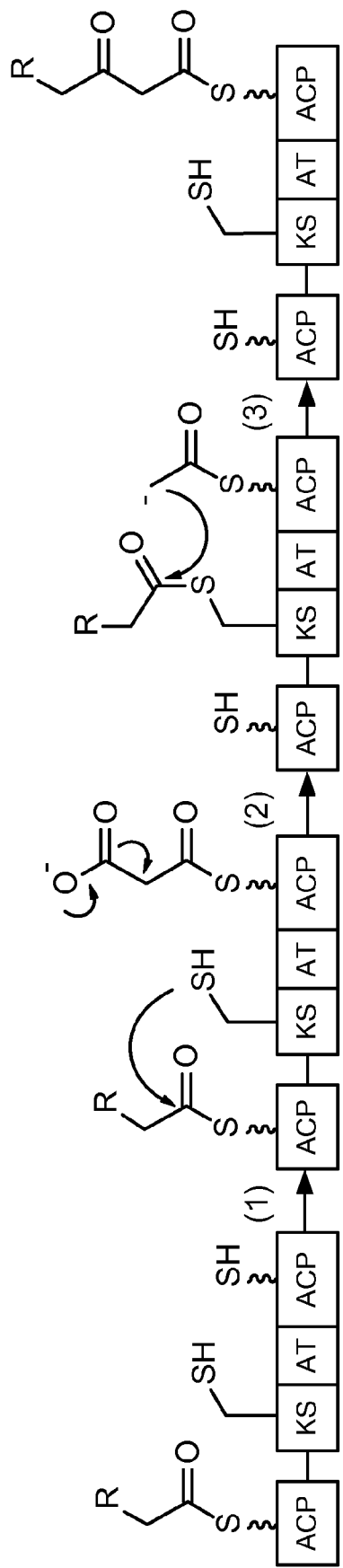

FIG. 2 summarizes the Claisen condensation catalyzed by polyketide synthases (PKSs). In step 1, an acyltransferase (AT) catalyzes thioester exchange between a specific extender unit (in this case malonyl-CoA) and a thiol group on a pantetheinyl group attached to an ACP. CoA is displaced in this reaction. All ACPs must be post-translationally modified by a phosphopantetheinyl transferase in order to be active. In step 2, the (poly)ketide chain is transferred from the upstream ACP to an active site serine on the KS as the extender unit undergoes decarboxylation. In step 3, the ester linkage on the KS undergoes nucleophilic attack by the carbanion to yield a new polyketide chain that has been extended by two carbons.

Figure 3:
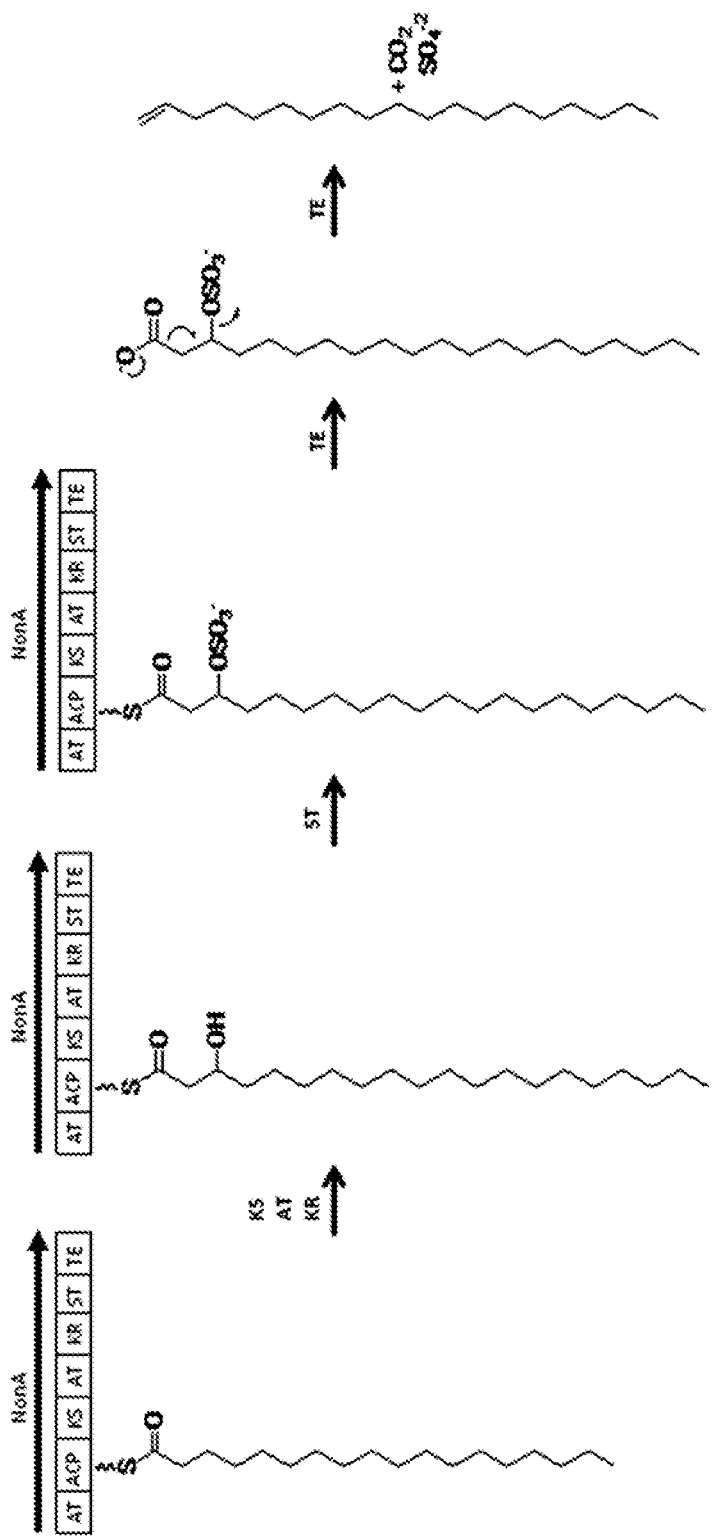

FIG. 3 illustrates the putative mechanism of 1-nonadecene biosynthesis from stearic acid, stearyl-ACP or stearyl-CoA. AT, acyltransferase; ACP, acyl-carrier protein; KS, ketosynthase; KR, ketoreductase; ST, sulfotransferase; TE, thioesterase.

Figure 4:
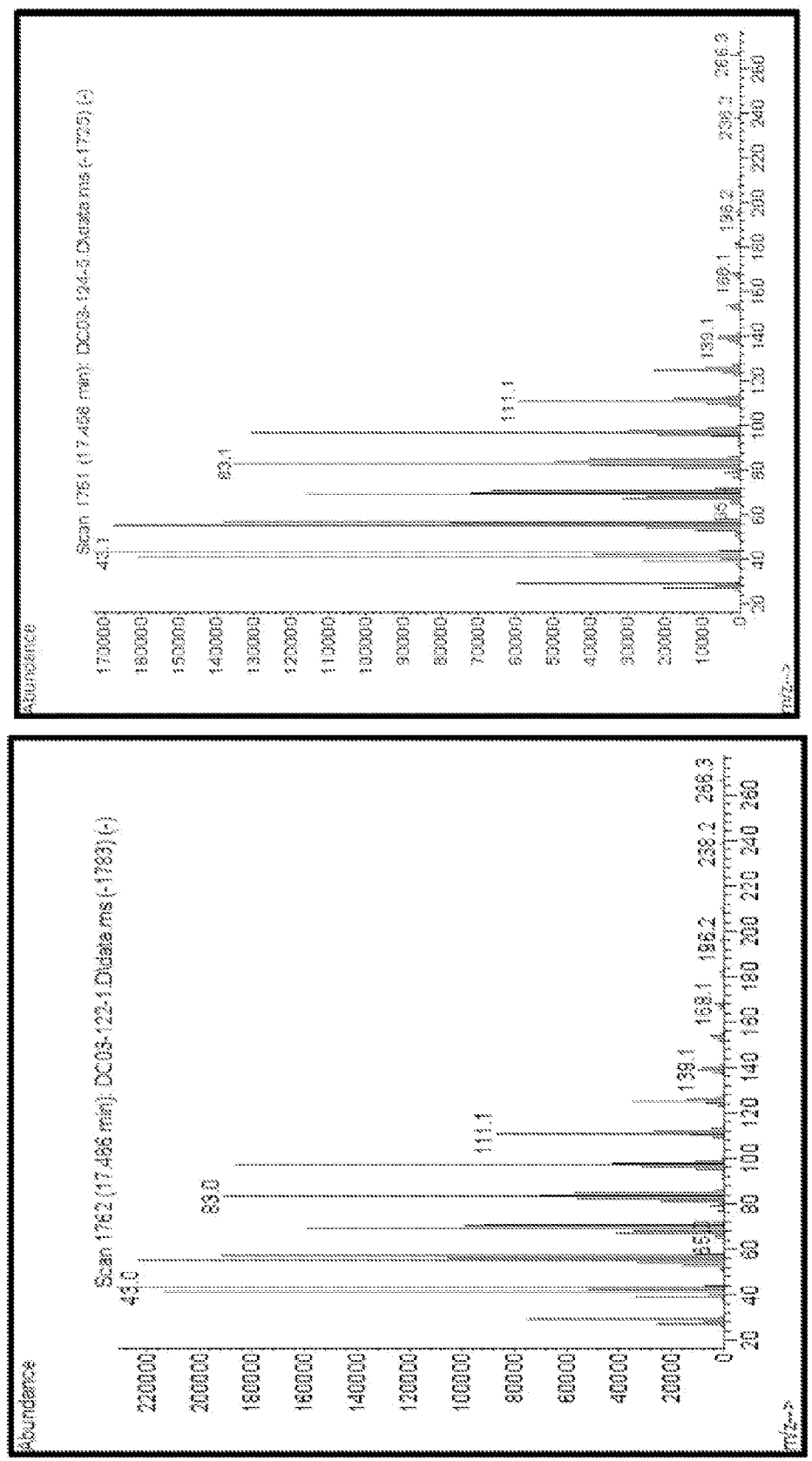

FIG. 4 shows the MS fragmentation patterns of 1-nonadecene (left) and the corresponding peak in the JCC138 cell pellet extract (right).

Figure 5:
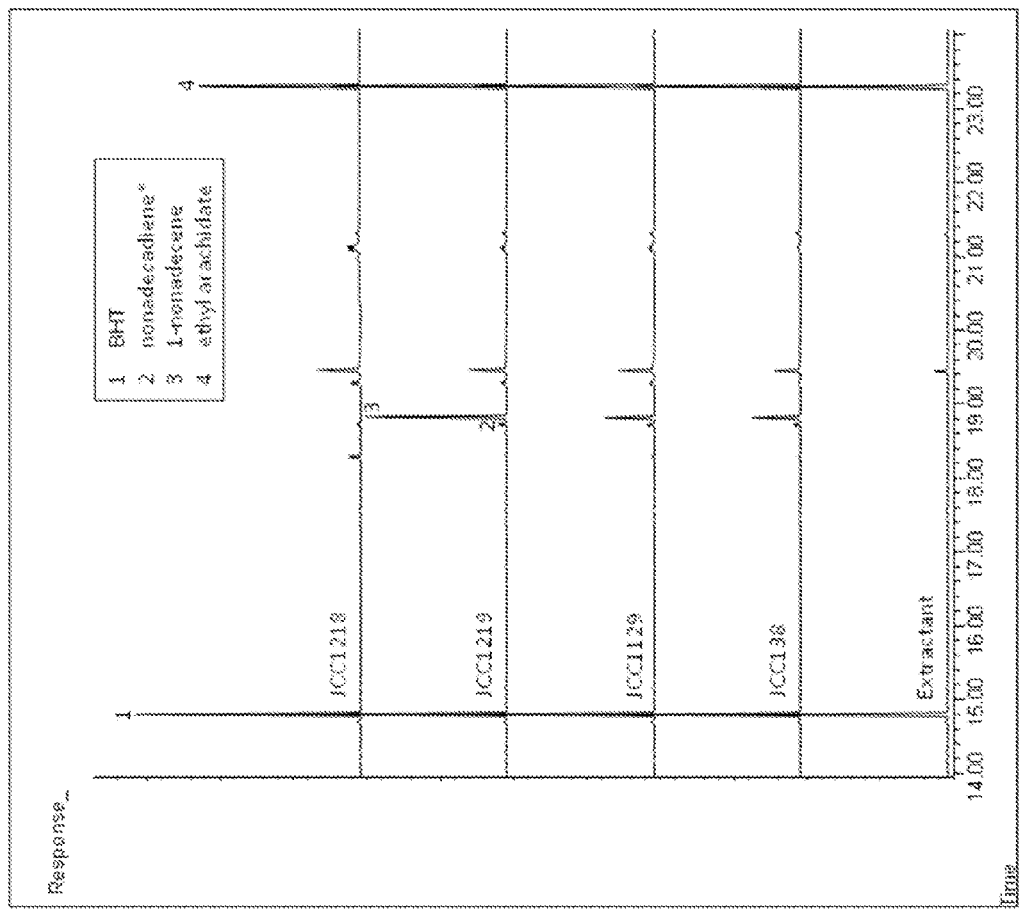
Figure 6:
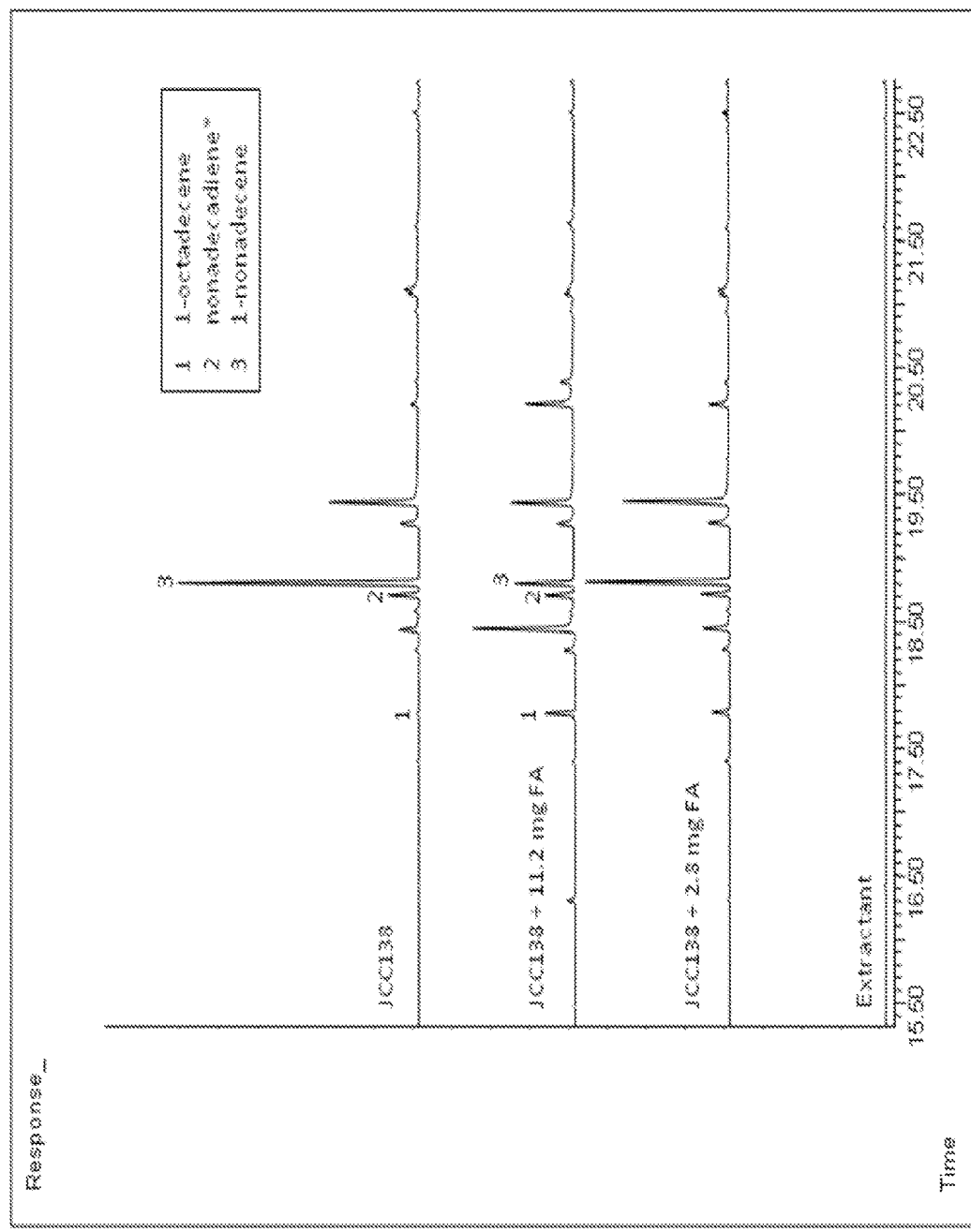

FIG. 5 shows GC/FID chromatograms in stacked form allowing comparison of the cell pellet extracts from the indicated cyanobacterial strains. The interval between tick marks on the FID response axis is 100,000. *Nonadecadiene co-elutes with an unrelated metabolite under these conditions. BHT=butylated hydroxytoluene FIG. 6 shows GC/FID chromatograms in stacked form allowing comparison of the acetone cell pellet extracts of JCC138 incubated with 0, 2.8 or 11.2 mg of tridecanoic acid. The interval between tick marks on the FID response axis is 10,000. *Nonadecadiene co-elutes with an unrelated metabolite under these conditions.

Figure 7:
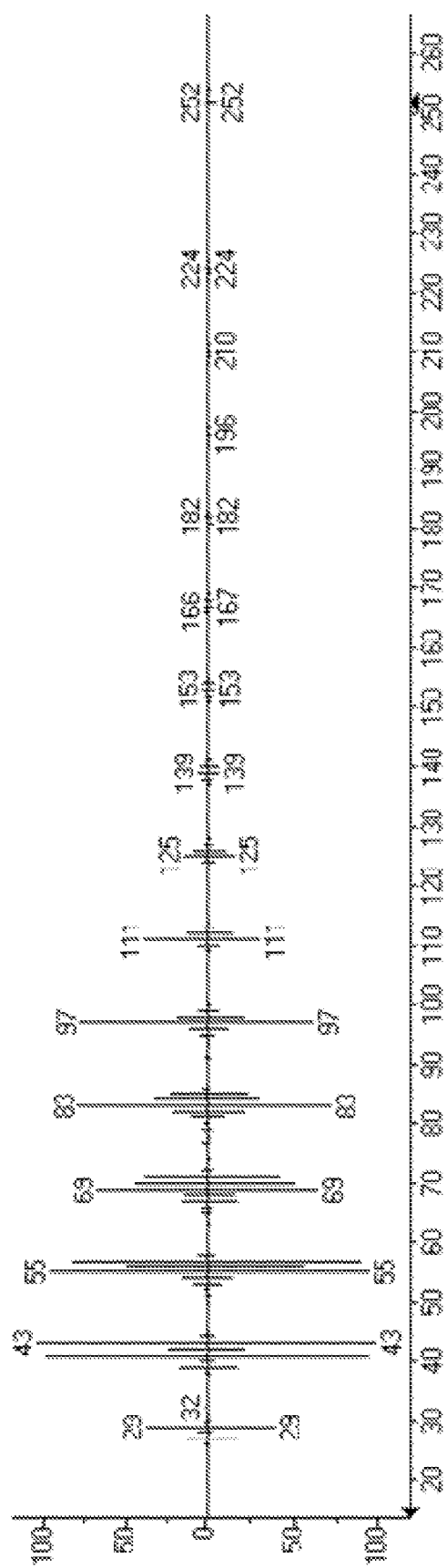

FIG. 7 shows MS fragmentation spectra of the JCC138 1-octadecene peak (top mass spectrum) plotted against the 1-octadecene spectrum in the NIST library (bottom mass spectrum).

DETAILED DESCRIPTION OF THE INVENTION

Unless otherwise defined herein, scientific and technical terms used in connection with the invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art. The methods and techniques are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol. I, CRC Press (1976); *Handbook of Biochemistry: Section A Proteins*, Vol. II, CRC Press (1976); *Essentials of Glycobiology*, Cold Spring Harbor Laboratory Press (1999).

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material or substantially free of culture medium when produced by recombinant techniques or substantially free of chemical precursors or other chemicals when chemically synthesized.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. For example, a "recombinant 1-alkene synthase" can be a protein encoded by a heterologous 1-alkene synthase gene; or a protein encoded by a duplicate copy of an endogenous 1-alkene synthase gene; or a protein encoded by a modified endogenous 1-alkene synthase gene; or a protein encoded by an endogenous 1-alkene synthase gene expressed from a heterologous promoter; or a protein encoded by an endogenous 1-alkene synthase gene where expression is driven, at least in part, by an endogenous promoter different from the organism's native 1-alkene synthase promoter.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

A particular, non-limiting example of a mathematical algorithm utilized for the comparison of sequences is that of Karlin and Altschul (*Proc. Natl. Acad. Sci.* (1990) USA 87:2264-68; *Proc. Natl. Acad. Sci.* USA (1993) 90: 5873-77) as used in the NBLAST and XBLAST programs (version 2.0) of Altschul et al. (*J. Mol. Biol.* (1990) 215:403-10). BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (*Nucleic Acids Research* (1997) 25(17):3389-3402). When utilizing BLAST and Gapped BLAST programs, the default parameters of the respective programs (e.g., XBLAST and NBLAST) can be used (http://www.ncbi.nlm.nih.gov). One skilled in the art may also use the ALIGN program incorporating the non-linear algorithm of Myers and Miller (*Comput. Appl. Biosci.* (1988) 4:11-17). For amino acid sequence comparison using the ALIGN program one skilled in the art may use a PAM120 weight residue table, a gap length penalty of 12, and a gap penalty of 4.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 71%, 72%, 73%, 74%, 75%, 76%, 77%, 78%, 79%, 80%, 81%, 82%, 83%, 84%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Intermediate ranges e.g., at 65-70° C. or at 42-50° C. are also within the scope of the invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$(° C.)=81.5+16.6($\log_{10}[Na^+]$)+0.41 (% G+C)−(600/N), where N is the number of bases in the hybrid, and [$Na^+$] is the concentration of sodium ions in the hybridization buffer ([$Na^+$] for 1×SSC=0.165 M).

The skilled practitioner recognizes that reagents can be added to hybridization and/or wash buffers. For example, to decrease non-specific hybridization of nucleic acid molecules to, for example, nitrocellulose or nylon membranes, blocking agents, including but not limited to, BSA or salmon or herring sperm carrier DNA and/or detergents, including but not limited to, SDS, chelating agents EDTA, Ficoll, PVP and the like can be used. When using nylon membranes, in particular, an additional, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (Church and Gilbert (1984) *Proc. Natl. Acad. Sci*. USA 81:1991-1995,) or, alternatively, 0.2×SSC, 1% SDS.

The nucleic acids (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "derived from" is intended to include the isolation (in whole or in part) of a polynucleotide segment from an indicated source. The term is intended to include, for example, direct cloning, PCR amplification, or artificial synthesis from, or based on, a sequence associated with the indicated polynucleotide source.

The term "gene" as used herein refers to a nucleotide sequence that can direct synthesis of an enzyme or other polypeptide molecule (e.g., can comprise coding sequences, for example, a contiguous open reading frame (ORF) which encodes a polypeptide) or can itself be functional in the organism. A gene in an organism can be clustered within an operon, as defined herein, wherein the operon is separated from other genes and/or operons by intergenic DNA. Individual genes contained within an operon can overlap without intergenic DNA between the individual genes.

An "isolated gene," as described herein, includes a gene which is essentially free of sequences which naturally flank the gene in the chromosomal DNA of the organism from which the gene is derived (i.e., is free of adjacent coding sequences which encode a second or distinct polypeptide or RNA molecule, adjacent structural sequences or the like) and optionally includes 5' and 3' regulatory sequences, for example promoter sequences and/or terminator sequences. In one embodiment, an isolated gene includes predominantly coding sequences for a polypeptide.

The term "expression" when used in relation to the transcription and/or translation of a nucleotide sequence as used herein generally includes expression levels of the nucleotide sequence being enhanced, increased, resulting in basal or housekeeping levels in the host cell, constitutive, attenuated, decreased or repressed.

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

A "deletion" is the removal of one or more nucleotides from a nucleic acid molecule or one or more amino acids from a protein, the regions on either side being joined together.

A "knock-out" is a gene whose level of expression or activity has been reduced to zero. In some examples, a gene is knocked-out via deletion of some or all of its coding sequence. In other examples, a gene is knocked-out via introduction of one or more nucleotides into its open-reading frame, which results in translation of a non-sense or otherwise non-functional protein product.

The term "codon usage" is intended to refer to analyzing a nucleic acid sequence to be expressed in a recipient host organism (or acellular extract thereof) for the occurrence and use of preferred codons the host organism transcribes advantageously for optimal nucleic acid sequence transcription. The recipient host may be recombinantly altered with any preferred codon. Alternatively, a particular cell host can be selected that already has superior codon usage, or the nucleic acid sequence can be genetically engineered to change a limiting codon to a non-limiting codon (e.g., by introducing a silent mutation(s)).

The term "vector" as used herein is intended to refer to a nucleic acid molecule capable of transporting another nucleic acid to which it has been linked. One type of vector is a "plasmid," which refers to a circular double stranded DNA loop into which additional DNA segments may be ligated. Other vectors include cosmids, bacterial artificial chromosomes (BAC) and yeast artificial chromosomes (YAC), fosmids, phage and phagemids. Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Expression optimization" as used herein is defined as one or more optional modifications to the nucleotide sequence in the promoter and terminator elements resulting in desired rates and levels of transcription and translation into a protein product encoded by said nucleotide sequence. Expression optimization as used herein also includes designing an effectual predicted secondary structure (for example, stem-loop structures and termination sequences) of the messenger ribonucleic acid (mRNA) sequence to promote desired levels of protein production. Other genes and gene combinations essential for the production of a protein may be used, for example genes for proteins in a biosynthetic pathway, required for post-translational modifications or required for a heteromultimeric protein, wherein combinations of genes are chosen for the effect of optimizing expression of the desired levels of protein product. Conversely, one or more genes optionally may be "knocked-out" or otherwise altered such that lower or eliminated expression of said gene or genes achieves the desired expression levels of protein. Additionally, expression optimization can be achieved through codon optimization. Codon optimization, as used herein, is defined as modifying a nucleotide sequence for effectual use of host cell bias in relative concentrations of transfer ribonucleic acids (tRNA) such that the desired rate and levels of gene nucleotide sequence translation into a final protein product are achieved, without altering the peptide sequence encoded by the nucleotide sequence.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

An isolated or purified polypeptide is substantially free of cellular material or other contaminating polypeptides from the expression host cell from which the polypeptide is derived, or substantially free from chemical precursors or other chemicals when chemically synthesized. In one embodiment, an isolated or purified polypeptide has less than about 30% (by dry weight) of contaminating polypeptide or chemicals, more advantageously less than about 20% of contaminating polypeptide or chemicals, still more advantageously less than about 10% of contaminating polypeptide or chemicals, and most advantageously less than about 5% contaminating polypeptide or chemicals.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The terms "thermal stability" and "thermostability" are used interchangeably and refer to the ability of an enzyme (e.g., whether expressed in a cell, present in an cellular extract, cell lysate, or in purified or partially purified form) to exhibit the ability to catalyze a reaction at least at about 20° C., preferably at about 25° C. to 35° C., more preferably at about 37° C. or higher, in more preferably at about 50° C. or higher, and even more preferably at least about 60° C. or higher.

The term "chimeric" refers to an expressed or translated polypeptide in which a domain or subunit of a particular homologous or non-homologous protein is genetically engineered to be transcribed, translated and/or expressed collinearly in the nucleotide and amino acid sequence of another homologous or non-homologous protein.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins have particular utility. The heterologous polypeptide included within the fusion protein is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "protomer" refers to a polymeric form of amino acids forming a subunit of a larger oligomeric protein structure. Protomers of an oligomeric structure may be identical or non-identical. Protomers can combine to form an oligomeric subunit, which can combine further with other identical or non-identical protomers to form a larger oligomeric protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab')$_2$, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications* (1998) Marasco, ed., Springer-Verlag New York, Inc.), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic." See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 85% overall sequence homology to its wild-type counterpart. Even more preferred are muteins having at least 90% overall sequence homology to the wild-type protein.

In an even more preferred embodiment, a mutein exhibits at least 95% sequence identity, even more preferably 98%, even more preferably 99% and even more preferably 99.9% overall sequence identity.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-331 and 25:365-389 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K);

5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., Nucleic Acids Res. 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. (Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

To determine the percent identity of two amino acid sequences or of two nucleic acids, the sequences are aligned for optimal comparison purposes, and, if necessary, gaps can be introduced in the first amino acid or nucleic acid sequence for optimal alignment with a second amino or nucleic acid sequence. When a position in the first sequence is occupied by the same amino acid residue or nucleotide as the corresponding position in the second sequence, then the molecules are identical at that position. The percent identity between the two sequences is a function of the number of identical positions shared by the sequences as evaluated, for example, by calculating # of identical positions/total # of positions×100. Additional evaluations of the sequence alignment can include a numeric penalty taking into account the number of gaps and size of said gaps necessary to produce an optimal alignment.

"Specific binding" refers to the ability of two molecules to bind to each other in preference to binding to other molecules in the environment. Typically, "specific binding" discriminates over adventitious binding in a reaction by at least twofold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

The term "substrate affinity" as used herein refers to the binding kinetics, $K_m$, the Michaelis-Menten constant as understood by one having skill in the art, for a substrate. More particularly the $K_m$ is optimized over endogenous activity for the purpose of the invention described herein.

The term "sugar" as used herein refers to any carbohydrate endogenously produced from sunlight, carbon dioxide and water, any carbohydrate produced endogenously and/or any carbohydrate from any exogenous carbon source such as biomass, comprising a sugar molecule or pool or source of such sugar molecules.

The term "carbon source" as used herein refers to carbon dioxide, exogenous sugar or biomass.

"Carbon-based products of interest" include alcohols such as ethanol, propanol, isopropanol, butanol, fatty alcohols, fatty acid esters, wax esters; hydrocarbons and alkanes such as propane, octane, diesel, Jet Propellant 8 (JP8); polymers such as 1-nonadecene, terephthalate, 1,3-propanediol, 1,4-butanediol, polyols, Polyhydroxyalkanoates (PHA), poly-beta-hydroxybutyrate (PHB), acrylate, adipic acid, ϵ-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids, olefins, alkenes and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

A "biofuel" as used herein is any fuel that derives from a biological source. A "fuel" refers to one or more hydrocarbons (e.g., 1-alkenes), one or more alcohols, one or more fatty esters or a mixture thereof. Preferably, liquid hydrocarbons are used.

As used herein, the term "hydrocarbon" generally refers to a chemical compound that consists of the elements carbon (C), hydrogen (H) and optionally oxygen (O). There are essentially three types of hydrocarbons, e.g., aromatic hydrocarbons, saturated hydrocarbons and unsaturated hydrocarbons such as alkenes, alkynes, and dienes. The term also includes fuels, biofuels, plastics, waxes, solvents and oils. Hydrocarbons encompass biofuels, as well as plastics, waxes, solvents and oils.

Polyketide synthases are enzymes or enzyme complexes that produce polyketides, a large class of secondary metabolites in bacteria, fungi, plants and animals. The invention described herein provides a recombinant 1-alkene synthase gene, which is related to type I polyketides synthases. As used herein, a "1-alkene synthase" is an enzyme which (1) comprises regions homologous or identical to each of the domains identified in FIG. 1, or whose BLAST alignment covers 90% of the length of YP_001734428.1 and has at least 50% identity to the amino acid sequence of YP_001734428.1, i.e., the 1-alkene synthase of Synechococcus sp. PCC 7002 (SEQ ID NO:2); and (2) which catalyzes the synthesis of 1-alkenes. The 1-alkene synthase is also referred to herein as NonA; the corresponding gene may be referred to as nonA.

An exemplary 1-alkene synthase is the 1-alkene synthase of Synechococcus sp. PCC 7002 (SEQ ID NO: 2). An exemplary gene encoding a 1-alkene synthase is the nonA gene of Synechococcus sp. PCC 7002 (SEQ ID NO:2). Other exemplary 1-alkene synthases are YP_002377174.1 from Cyanothece sp. PCC7424 (SEQ ID NO: 8) and ZP_03153601.1 from Cyanothece sp. PCC7822 (SEQ ID NO 9). The amino acid sequences of these genes as they appear in the NCBI database on Jun. 22, 2010 are hereby incorporated by reference. The invention also provides 1-alkene synthases that are at least 95% identical to SEQ ID NO:2, or at least 95% identical to YP_002377174.1 (SEQ ID NO: 8) or at least 95% identical to ZP_03153601.1 (SEQ ID NO: 9), in addition to engineered microorganisms expressing genes encoding these 1-alkene synthases and methods of producing 1-alkenes by culturing these microorganisms.

The invention also provides an isolated or recombinant A1174 hydrolase gene, which refers to a gene encoding a hydrolase with an amino acid sequence that is at least 95% identical to the YP_001734429.1 hydrolase of Synechococcus sp. PCC 7002 (SEQ ID NO:4).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The term "catabolic" and "catabolism" as used herein refers to the process of molecule breakdown or degradation of large molecules into smaller molecules. Catabolic or catabolism refers to a specific reaction pathway wherein the molecule breakdown occurs through a single or multitude of catalytic components or a general, whole cell process wherein the molecule breakdown occurs using more than one specified reaction pathway and a multitude of catalytic components.

The term "anabolic" and "anabolism" as used herein refers to the process of chemical construction of small molecules into larger molecules. Anabolic refers to a specific reaction pathway wherein the molecule construction occurs through a single or multitude of catalytic components or a general, whole cell process wherein the molecule construction occurs using more than one specified reaction pathway and a multitude of catalytic components.

The term "correlated" in "correlated saturation mutagenesis" as used herein refers to altering an amino acid type at two or more positions of a polypeptide to achieve an altered functional or structural attribute differing from the structural or functional attribute of the polypeptide from which the changes were made.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Nucleic Acid Sequences

The cyanobacterium Synechococcus sp. PCC7002 (formerly, Agmenellum quadruplicatum) has been shown to produce the linear alpha olefin 1-nonadecene (Winters et al. 1969). Strains which produce this metabolite also produce a nonadecadiene as a minor metabolite (Winters et al. 1969) which has been identified as 1,14-(cis)-nonadecadiene (Goodloe and Light, 1982). Feeding of $^{14}$C-labelled stearic acid resulted in incorporation of the fatty acid into 1-nonadecene demonstrating that the olefin is derived from fatty acid biosynthesis (Goodloe and Light, 1982) but the enzyme or enzymes responsible for the production of the olefin was not identified.

In one embodiment, the invention therefore provides an isolated 1-alkene synthase gene, defined above, which encodes an enzyme (NonA) related to type I polyketides synthases and which carries out the conversion of stearic acid to 1-nonadecene. Exemplary 1-alkane synthases include SYNPCC7002_A1173 (NCBI Sequence # NC_010475.1; SEQ ID NO: 1 and SEQ ID NO:2 are the nucleic acid and encoded protein sequences, respectively) and contain the catalytic domains needed to carry out the biosynthesis of 1-nonadecene (FIG. 1). The first domain is related to LuxE, which indicates that the protein can attach a fatty acid by acting as an acyltransferase (AT). LuxE is the protein which serves as an acyl-protein synthetase in the Lux operon (Lin et al. (1996)). A phosphopantetheinyl (PP) attachment site is next which is characteristic of acyl-carrier protein (ACP) domains. Several other domains are also present that include a ketosynthase (KS), an acyltransferase (AT), a ketoreductase (KR) domain, a sulfotransferase (ST) and a thioesterase (TE) domain.

In general, the biosynthesis of polyketides is similar to fatty acid synthesis, where a thioester bond is formed between a starter unit and an ACP of the PKS, and then Claisen condensations catalyzed by a β-ketosynthase (KS) occur between the acyl-thioester substrate and an acyl-CoA intermediate to form the growing polyketide chain (FIG. 2). During chain elongation each condensation step can be followed by sequential reactions of the β-carbonyl by a stereospecific β-keto reduction to form a βhydroxy, dehydration to yield α, β double bond, and an enoyl reduction resulting in the formation of a methylene. The chains are extended for a defined number of times until released from the enzyme through the action of a thioesterase domain.

The putative mechanism of 1-nonadecene biosynthesis by NonA is shown in FIG. 3. Step 1 is loading of stearic acid onto the ACP by the fatty acid acyl transferase. The likely starter unit is a thioester of stearate (i.e., stearyl-ACP or stearyl-CoA) as opposed to the free acid. In the second step, a round of chain extension occurs, extending the carbon chain by two carbons through decarboxylative condensation with malonyl-CoA. This is followed by reduction of the β-carbonyl by the ketoreductase. The sulfotransferase domain attaches a sulfonate to the β-hydroxyl to yield a sulfate group, and the thioesterase domain catalyzes hydrolysis of the thioester bond which is followed by a decarboxylative elimination of sulfate to yield the terminal alkene.

An object of the invention described herein is to recombinantly express in a host cell genes encoding 1-alkene synthase to produce 1-alkenes, including 1-nonadecene and 1-octadecene, and other carbon-based products of interest. The pathway can be over-expressed in a *Synechococcus* strain such as JCC138 (*Synechococcus* sp. PCC 7002) or any other photosynthetic organism to produce a hydrocarbon from light and carbon dioxide. It can also be expressed in non-photosynthetic organisms to produce hydrocarbons from sugar sources. Accordingly, the invention provides isolated nucleic acid molecules encoding enzymes having 1-alkene synthase activity, and variants thereof, including expression optimized forms of said polyketide and hydrolase genes, and methods of improvement thereon. The full-length nucleic acid sequence (SEQ ID NO:1) for the 1-alkene synthase gene from *Synechococcus* sp. PCC 7002, YP_001734428, is provided herein, as is the protein sequence (SEQ ID NO:2).

Also provided herein is a coding (SEQ ID NO:3) and amino acid sequence (SEQ ID NO:4) for an A1174 hydrolase, as defined above. An exemplary A1174 hydrolase is the hydrolase from *Synechococcus* sp. PCC 7002, YP_001734429 (also referred to as SYNPCC7002_A1174). In *Synechococcus* sp. PCC7002, the gene encoding this hydrolase is adjacent to the 1-alkene synthase gene. Deletion of the structural gene encoding this protein (but retaining its endogenous promoter) is shown herein to modulate the yield of 1-nonadecene produced by the cell.

In one embodiment is provided an isolated nucleic acid molecule having a nucleic acid sequence comprising or consisting of 1-alkene synthase gene homologs, variants and derivatives of the wild-type polyketide synthase gene coding sequence SEQ ID NO:1. The invention provides nucleic acid molecules comprising or consisting of sequences which are structurally and functionally optimized versions of the wild-type or native 1-alkene synthase gene. In a preferred embodiment, nucleic acid molecules and homologs, variants and derivatives comprising or consisting of sequences optimized for substrate affinity and/or substrate catalytic conversion rate are provided.

In one embodiment is provided an isolated nucleic acid molecule having a nucleic acid sequence comprising or consisting of A1174 hydrolase gene homologs, variants and derivatives of the wild-type hydrolase gene coding sequence SEQ ID NO:3. The invention provides nucleic acid molecules comprising or consisting of sequences which are structurally and functionally optimized versions of the native or wild-type A1174 hydrolase gene. In a preferred embodiment, nucleic acid molecules and homologs, variants and derivatives comprising or consisting of sequences optimized for substrate affinity and/or substrate catalytic conversion rate are provided.

In other embodiments, the invention provides vectors constructed for the preparation of nonA and/or A1174 gene-knockout strains of *Synechococcus* sp. PCC7002 and other cyanobacterial strains. These vectors contain sufficient lengths of upstream and downstream sequences relative to the respective gene flanking a selectable marker, e.g., an antibiotic resistance marker (gentamycin, kanamycin, ampicillin, etc.), such that recombination with the vector replaces the chromosomal copy of the gene with the antibiotic resistance gene. Exemplary examples of such vectors are provided herein (e.g., SEQ ID NO:5 and SEQ ID NO:6).

In other embodiments, the invention provides knockout strains of cyanobacteria and other microbes wherein the A1774 gene or the nonA gene is inactivated by mutation or deletion.

In a further embodiment is provided nucleic acid molecules and homologs, variants and derivatives thereof comprising or consisting of sequences which are variants of the 1-alkene synthase gene having at least 71% identity to SEQ ID NO:1. In a further embodiment provided nucleic acid molecules and homologs, variants and derivatives comprising or consisting of sequences which are variants of the 1-alkene synthase gene having at least 50% identity to SEQ ID NO:1 and optimized for substrate affinity, substrate catalytic conversion rate, improved thermostability, activity at a different pH and/or optimized codon usage for improved expression in a host cell. The nucleic acid sequences can be preferably 71%, 72%, 73%, 74%, 75%, 76%, 77%, 78%, 79%, 80%, 81%, 82%, 83%, 84%, 85%, 90%, 95%, 98%, 99%, 99.9% or even higher identity to the wild-type gene.

In a further embodiment is provided nucleic acid molecules and homologs, variants and derivatives thereof comprising or consisting of sequences which are variants of the A1174 hydrolase gene having at least 71% identity to SEQ ID NO:3. In a further embodiment provided nucleic acid molecules and homologs, variants and derivatives comprising or consisting of sequences which are variants of the A1174 hydrolase gene having at least 71% identity to SEQ ID NO:3 and optimized for substrate affinity, substrate catalytic conversion rate, improved thermostability, activity at a different pH and/or optimized codon usage for improved expression in a host cell. The nucleic acid sequences can be preferably 71%, 72%, 73%, 74%, 75%, 76%, 77%, 78%, 79%, 80%, 81%, 82%, 83%, 84%, 85%, 90%, 95%, 98%, 99%, 99.9% or even higher identity to the wild-type gene.

In another embodiment, the nucleic acid molecule encodes a polypeptide having the amino acid sequence of SEQ ID NO:2 and/or SEQ NO:4. Also provided is a nucleic acid molecule encoding a polypeptide sequence that is at least 50% identical to either SEQ ID NO:2 or SEQ ID NO:4. Preferably, the nucleic acid molecule encodes a polypeptide sequence of at least 55%, 60%, 70%, 80%, 90% or 95% identical to SEQ ID NO:2 or SEQ ID NO:4, and the identity can even more preferably be 98%, 99%, 99.9% or even higher.

Provided also are nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing can be performed at temperatures about 5° C. lower than the $T_m$ for the specific DNA hybrid under a particular set of conditions.

The nucleic acid molecule includes DNA molecules (e.g., linear, circular, cDNA, chromosomal DNA, double stranded or single stranded) and RNA molecules (e.g., tRNA, rRNA, mRNA) and analogs of the DNA or RNA molecules of the described herein using nucleotide analogs. The isolated nucleic acid molecule of the invention includes a nucleic acid molecule free of naturally flanking sequences (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of naturally flanking nucleotide chromosomal DNA sequences of the microorganism from which the nucleic acid molecule is derived.

The 1-alkene synthase and/or A1174 hydrolase genes, as described herein, include nucleic acid molecules, for example, a polypeptide or RNA-encoding nucleic acid molecule, separated from another gene or other genes by intergenic DNA (for example, an intervening or spacer DNA which naturally flanks the gene and/or separates genes in the chromosomal DNA of the organism).

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

In another embodiment, an isolated 1-alkene synthase-encoding nucleic acid molecule hybridizes to all or a portion of a nucleic acid molecule having the nucleotide sequence set forth in SEQ ID NO:1 or hybridizes to all or a portion of a nucleic acid molecule having a nucleotide sequence that encodes a polypeptide having the amino acid sequence of SEQ ID NO: 2. Such hybridization conditions are known to those skilled in the art (see, for example, *Current Protocols in Molecular Biology*, Ausubel et al., eds., John Wiley & Sons, Inc. (1995); *Molecular Cloning: A Laboratory Manual*, Sambrook et al., Cold Spring Harbor Press, Cold Spring Harbor, N.Y. (1989)). In another embodiment, an isolated nucleic acid molecule comprises a nucleotide sequence that is complementary to a 1-alkene synthase-encoding nucleotide sequence as set forth herein.

In another embodiment, an isolated hydrolase-encoding nucleic acid molecule hybridizes to all or a portion of a nucleic acid molecule having the nucleotide sequence set forth in SEQ ID NO:3 or hybridizes to all or a portion of a nucleic acid molecule having a nucleotide sequence that encodes a polypeptide having the amino acid sequence of SEQ ID NO: 4. Such hybridization conditions are known to those skilled in the art (see, for example, *Current Protocols in Molecular Biology*, Ausubel et al., eds., John Wiley & Sons, Inc. (1995); *Molecular Cloning: A Laboratory Manual*, Sambrook et al., Cold Spring Harbor Press, Cold Spring Harbor, N.Y. (1989)). In another embodiment, an isolated nucleic acid molecule comprises a nucleotide sequence that is complementary to a polyketide synthase-encoding nucleotide sequence as set forth herein.

The nucleic acid sequence fragments display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (Practical Approach Series), Schena (ed.), Oxford University Press (1999) (ISBN: 0199637768); *Nature Genet.* 21(1)(suppl):1-60 (1999); Microarray Biochip: Tools and Technology, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); DNA Microarrays: A Practical Approach (Practical Approach Series), Schena (ed.), Oxford University Press (1999) (ISBN: 0199637768); *Nature Genet.* 21(1)(suppl):1-60 (1999); Microarray Biochip: Tools and Technology, Schena (ed.), Eaton Publishing Company/BioTechniques Books Division (2000) (ISBN: 1881299376), the disclosures of each of which is incorporated herein by reference in its entirety.

In another embodiment, the invention provides isolated nucleic acid molecules encoding a 1-alkene synthase in a 1-nonadecene biosynthetic pathway which exhibit increased activity.

As is well known in the art, enzyme activities are measured in various ways. For example, the pyrophosphorolysis of OMP may be followed spectroscopically. Grubmeyer et al., *J. Biol. Chem.* 268:20299-20304 (1993). Alternatively, the activity of the enzyme is followed using chromatographic techniques, such as by high performance liquid chromatography. Chung and Sloan, *J. Chromatogr.* 371:71-81 (1986). As another alternative the activity is indirectly measured by determining the levels of product made from the enzyme activity. More modern techniques include using gas chromatography linked to mass spectrometry (Niessen, W. M. A. (2001). *Current practice of gas chromatography—mass spectrometry*. New York, N.Y: Marcel Dekker. (ISBN: 0824704738)). Additional modern techniques for identification of recombinant protein activity and products including liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G., R. O. Dunn, and M. O. Bagby. 1997. Biodiesel: The use of vegetable oils and their derivatives as alternative diesel fuels. *Am. Chem. Soc. Symp.* Series 666: 172-208), physical property-based methods, wet chemical methods, etc. are used to analyze the levels and the identity of the product produced by the organisms. Other methods and techniques may also be suitable for the measurement of enzyme activity, as would be known by one of skill in the art.

Another embodiment comprises mutant or chimeric 1-alkene synthase and/or A1174 hydrolase nucleic acid molecules or genes. Typically, a mutant nucleic acid molecule or mutant gene is comprised of a nucleotide sequence that has at least one alteration including, but not limited to, a simple substitution, insertion or deletion. The polypeptide of said mutant can exhibit an activity that differs from the polypeptide encoded by the wild-type nucleic acid molecule or gene. Typically, a chimeric mutant polypeptide includes an entire domain derived from another polypeptide that is genetically engineered to be collinear with a corresponding domain. Preferably, a mutant nucleic acid molecule or mutant gene encodes a polypeptide having improved activity such as substrate affinity, substrate specificity, improved thermostability, activity at a different pH, or optimized codon usage for improved expression in a host cell.

Vectors

The recombinant vector can be altered, modified or engineered to have different or a different quantity of nucleic acid sequences than in the derived or natural recombinant vector nucleic acid molecule. Preferably, the recombinant vector includes a gene or recombinant nucleic acid molecule operably linked to regulatory sequences including, but not limited to, promoter sequences, terminator sequences and/or artificial ribosome binding sites (RBSs), as defined herein.

Typically, a gene encoding 1-alkene synthase is operably linked to regulatory sequence(s) in a manner which allows for the desired expression characteristics of the nucleotide sequence. Preferably, the gene encoding a 1-alkene synthase in a 1-nonadecene biosynthetic pathway is transcribed and translated into a gene product encoded by the nucleotide sequence when the recombinant nucleic acid molecule is included in a recombinant vector, as defined herein, and is introduced into a microorganism.

The regulatory sequence may be comprised of nucleic acid sequences which modulate, regulate or otherwise affect expression of other nucleic acid sequences. In one embodiment, a regulatory sequence can be in a similar or identical position and/or orientation relative to a nucleic acid sequence as observed in its natural state, e.g., in a native position and/or orientation. For example, a gene of interest can be included in a recombinant nucleic acid molecule or recombinant vector operably linked to a regulatory sequence which accompanies or is adjacent to the gene of interest in the natural host cell, or can be adjacent to a different gene in the natural host cell, or can be operably linked to a regulatory sequence from another organism. Regulatory sequences operably linked to a gene can be from other bacterial regulatory sequences, bacteriophage regulatory sequences and the like.

In one embodiment, a regulatory sequence is a sequence which has been modified, mutated, substituted, derivated, deleted, including sequences which are chemically synthesized. Preferably, regulatory sequences include promoters, enhancers, termination signals, anti-termination signals and other expression control elements that, for example, serve as sequences to which repressors or inducers bind or serve as or encode binding sites for transcriptional and/or translational regulatory polypeptides, for example, in the transcribed mRNA (see Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989). Regulatory sequences include promoters directing constitutive expression of a nucleotide sequence in a host cell, promoters directing inducible expression of a nucleotide sequence in a host cell and promoters which attenuate or repress expression of a nucleotide sequence in a host cell. Regulating expression of a gene of interest also can be done by removing or deleting regulatory sequences. For example, sequences involved in the negative regulation of transcription can be removed such that expression of a gene of interest is enhanced. In one embodiment, a recombinant nucleic acid molecule or recombinant vector includes a nucleic acid sequence or gene that encodes at least one bacterial 1-alkene synthase, wherein the gene encoding the enzyme(s) is operably linked to a promoter or promoter sequence. Preferably, promoters include native promoters, surrogate promoters and/or bacteriophage promoters.

In one embodiment, a promoter is associated with a biochemical housekeeping gene. In another embodiment, a promoter is a bacteriophage promoter. Other promoters include tef (the translational elongation factor (TEF) promoter) which promotes high level expression in *Bacillus* (e.g. *Bacillus subtilis*). Additional advantageous promoters, for example, for use in Gram positive microorganisms include, but are not limited to, the amyE promoter or phage SP02 promoters. Additional advantageous promoters, for example, for use in Gram negative microorganisms include, but are not limited to tac, trp, tet, trp-tet, lpp, lac, lpp-lac, lacIq, T7, T5, T3, gal, trc, ara, SP6, $\lambda$-$p_R$ or $\lambda$-$p_L$.

In another embodiment, a recombinant nucleic acid molecule or recombinant vector includes a transcription terminator sequence or sequences. Typically, terminator sequences refer to the regulatory sequences which serve to terminate transcription of a gene. Terminator sequences (or tandem transcription terminators) can further serve to stabilize mRNA (e.g., by adding structure to mRNA), for example, against nucleases.

In another embodiment, a recombinant nucleic acid molecule or recombinant vector has sequences allowing for detection of the vector containing sequences (i.e., detectable and/or selectable markers), for example, sequences that overcome auxotrophic mutations (e.g. ura3 or ilvE), fluorescent markers, and/or calorimetric markers (e.g., lacZ/$\beta$-galactosidase), and/or antibiotic resistance genes (e.g., gen, spec, bla or tet).

It is understood that any one of the polyketide synthase and/or a hydrolase genes of the invention can be introduced into a vector also comprising one or more genes involved in the biosynthesis of 1-nonadecene from light, water and carbon dioxide.

Also provided are vectors, including expression vectors, which comprise the above nucleic acid molecules, as described further herein. In a first embodiment, the vectors include the isolated nucleic acid molecules described above. In an alternative embodiment, the vectors include the above-described nucleic acid molecules operably linked to one or more expression control sequences. The vectors of the instant invention may thus be used to express a polypeptide having 1-alkene synthase in a 1-nonadecene biosynthetic pathway.

Vectors useful for expression of nucleic acids in prokaryotes are well known in the art. A useful vector herein is plasmid pCDF Duet-1 that is available from Novagen. Another useful vector is the endogenous *Synechococcus* sp. PCC 7002 plasmid pAQ1 (Genbank accession number NC_010476).

Isolated Polypeptides

In one embodiment, polypeptides encoded by nucleic acid sequences are produced by recombinant DNA techniques and can be isolated from expression host cells by an appropriate purification scheme using standard polypeptide purification techniques. In another embodiment, polypeptides encoded by nucleic acid sequences are synthesized chemically using standard peptide synthesis techniques.

Included within the scope of the invention are polyketide synthase polypeptides or gene products that are derived polypeptides or gene products encoded by naturally-occurring bacterial genes. Further, included within the inventive scope, are bacteria-derived polypeptides or gene products which differ from wild-type genes, including genes that have altered, inserted or deleted nucleic acids but which encode polypeptides substantially similar in structure and/or function to the wild-type 1-alkene synthase gene. Similar variants with respect to the A1174 hydrolase are also included within the scope of the invention.

For example, it is well understood that one of skill in the art can mutate (e.g., substitute) nucleic acids which, due to the degeneracy of the genetic code, encode for an identical amino acid as that encoded by the naturally-occurring gene. This may be desirable in order to improve the codon usage of a nucleic acid to be expressed in a particular organism. Moreover, it is well understood that one of skill in the art can mutate (e.g., substitute) nucleic acids which encode for conservative amino acid substitutions. It is further well understood that one of skill in the art can substitute, add or delete amino acids to a certain degree to improve upon or at least insubstantially affect the function and/or structure of a gene product (e.g., 1-alkene synthase activity) as compared with a naturally-occurring gene product, each instance of which is intended to be included within the scope of the invention. For example, the 1-alkene synthase activity, enzyme/substrate affinity, enzyme thermostability, and/or enzyme activity at various pHs can be unaffected or rationally altered and readily evaluated using the assays described herein.

In various aspects, isolated polypeptides (including muteins, allelic variants, fragments, derivatives, and analogs) encoded by the nucleic acid molecules are provided. In one embodiment, the isolated polypeptide comprises the polypeptide sequence corresponding to SEQ ID NO:2 or SEQ ID NO:4. In an alternative embodiment, the isolated polypeptide comprises a polypeptide sequence at least 50% identical to SEQ ID NO:2 or SEQ ID NO:4. Preferably the isolated polypeptide has preferably 50%, 60%-70%, 70%-80%, 80%-90%, 90%-95%, 95%-98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to the sequences optimized for substrate affinity and/or substrate catalytic conversion rate.

According to other embodiments, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides also include fusions between the above-described polypeptide sequences and heterologous polypeptides. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cell Transformants

In other aspects, host cells transformed with the nucleic acid molecules or vectors, and descendants thereof, are provided. In some embodiments, these cells carry the nucleic acid sequences on vectors which may be freely replicating vectors, e.g., pAQ1, pAQ3, pAQ4, pAQ5, pAQ6, and pAQ7. In other embodiments, the nucleic acids have been integrated into the genome of the host cells.

The host cell encoding 1-alkene synthase can be a host cell lacking an endogenous 1-alkene synthase gene or a host with an endogenous 1-alkene synthase gene. The host cell can be engineered to express a recombinant 1-alkene synthase in addition to its endogenous 1-alkene synthase gene, and/or the host cell can be modified such that its endogenous 1-alkene synthase gene is overexpressed (e.g., by promoter swapping or by increasing read-through from an upstream promoter).

In a preferred embodiment, the host cell comprises one or more recombinant nucleic acids encoding a 1-alkene synthase (e.g., SEQ ID NO:1).

In an alternative embodiment, the host cells can be mutated by recombination with a disruption, deletion or mutation of the isolated nucleic acid so that the activity of the 1-alkene synthase is reduced or eliminated compared to a host cell lacking the mutation.

In another embodiment, the host cell containing a 1-alkene synthase is suitable for producing 1-nonadecene or 1 octadiene. In a particular embodiment, the host cell is a recombinant host cell that produces 1-nonadecene comprising a heterologous nucleic acid encoding a nucleic acid of SEQ ID NO:1.

In certain aspects, methods for expressing a polypeptide under suitable culture conditions and choice of host cell line for optimal enzyme expression, activity and stability (codon usage, salinity, pH, temperature, etc.) are provided.

In another aspect, the invention provides methods for producing 1-alkenes (e.g., 1-nonadecene, 1-octadecene, and/or other long-chain 1-alkenes) by culturing a host cell under conditions in which the 1-alkene synthase is expressed at sufficient levels to produce a measurable quantity of the -alkene of interest (e.g., 1-nonadecene, 1-octadecene, etc). In a related embodiment, methods for producing 1-alkenes are carried out by contacting a cell lysate obtained from the above host cell under conditions in which the 1-alkenes are produced from light, water and carbon dioxide. Accordingly, the invention provides enzyme extracts having improved 1-alkene synthase activity, and having, for example, thermal stability, activity at various pH, and/or superior substrate affinity or specificity.

Selected or Engineered Microorganisms for the Production of Carbon-Based Products of Interest Microorganism: Includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

A variety of host organisms can be transformed to produce 1-alkenes. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Host cells can be a Gram-negative bacterial cell or a Gram-positive bacterial cell. A Gram-negative host cell of the invention can be, e.g., *Gluconobacter, Rhizobium, Bradyrhizobium, Alcaligenes, Rhodobacter, Rhodococcus. Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas Zymobacter,* or *Acetobacter*. A Gram-positive host cell of the invention can be, e.g., *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus,*

*Sulfobacillus, Clostridium, Anaerobacter, Eubacterium, Streptococcus, Lactobacillus, Leuconostoc, Enterococcus, Lactococcus, Thermobifida, Cellulomonas,* or *Sarcina.*

Extremophiles are also contemplated as suitable organisms. Such organisms withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure tolerant organisms include piezophiles or barophiles which tolerate pressure of 130 MPa. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt tolerant organisms include halophiles (e.g., 2-5 M NaCl) *Halobacteriacea* and *Dunaliella salina*. pH tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments*. New York: Plenum (1998) and Seckbach, J. "Search for Life in the Universe with Terrestrial Microbes Which Thrive Under Extreme Conditions." In Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea*.

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysosphaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium, Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus,*

*Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis,* and *Zygonium.*

Green non-sulfur bacteria include but are not limited to the following genera: *Chloroflexus, Chloronema, Oscillochloris, Heliothrix, Herpetosiphon, Roseiflexus,* and *Thermomicrobium.*

Green sulfur bacteria include but are not limited to the following genera: *Chlorobium, Clathrochloris,* and *Prosthecochloris.*

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus,* and *Thiocystis,*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio,* and *Roseospira.*

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic sulfur-metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

In preferred embodiments the parental photoautotrophic organism can be transformed with a gene encoding 1-alkene synthase.

Preferred organisms for HyperPhotosynthetic conversion include: *Arabidopsis thaliana, Panicum virgatum, Miscanthus giganteus,* and *Zea mays* (plants), *Botryococcus braunii, Chlamydomonas reinhardtii* and *Dunaliela salina* (algae), *Synechococcus* sp PCC 7002, *Synechococcus* sp. PCC 7942, *Synechocystis* sp. PCC 6803, and *Thermosynechococcus elongatus* BP-1 (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus,* and *Rhodopseudomonas palusris* (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms include microorganisms that can be engineered to fix carbon dioxide bacteria such as *Escherichia coli, Acetobacter aceti, Bacillus subtilis,* yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens,* or *Zymomonas mobilis.*

A common theme in selecting or engineering a suitable organism is autotrophic fixation of $CO_2$ to products. This would cover photosynthesis and methanogenesis. Acetogenesis, encompassing the three types of $CO_2$ fixation; Calvin cycle, acetyl CoA pathway and reductive TCA pathway is also covered. The capability to use carbon dioxide as the sole source of cell carbon (autotrophy) is found in almost all major groups of prokaryotes. The $CO_2$ fixation pathways differ between groups, and there is no clear distribution pattern of the four presently-known autotrophic pathways. Fuchs, G. 1989. Alternative pathways of autotrophic $CO_2$ fixation, p. 365-382. In H. G. Schlegel, and B. Bowien (ed.), *Autotrophic bacteria*. Springer-Verlag, Berlin, Germany. The reductive pentose phosphate cycle (Calvin-Bassham-Benson cycle) represents the $CO_2$ fixation pathway in many aerobic autotrophic bacteria, for example, cyanobacteria.

Gene Integration and Propagation

The 1-nonadecene producing gene can be propagated by insertion into the host cell genome. Integration into the genome of the host cell is optionally done at particular loci to impair or disable unwanted gene products or metabolic pathways.

In another embodiment is described the integration of a 1-alkene synthase gene and/or a hydrolase gene in the 1-alkene synthesis pathway into a plasmid. The plasmid can express one or more genes, optionally an operon including one or more genes, preferably one or more genes involved in the synthesis of 1-alkenes, or more preferably one or more genes of a related metabolic pathway that feeds into the biosynthetic pathway for 1-alkenes.

Yet another embodiment provides a method of integrating one or more 1-alkene synthase genes into an expression vector including, but not limited to, pJB5 (see, e.g., WO 2009/111513, published Sep. 11, 2009) or pCDFDuet-1 (Novagen).

Antibodies

In another aspect, provided herein are isolated antibodies, including fragments and derivatives thereof that bind specifically to the isolated polypeptides and polypeptide fragments or to one or more of the polypeptides encoded by the isolated nucleic acids. The antibodies may be specific for linear epitopes, discontinuous epitopes or conformational epitopes of such polypeptides or polypeptide fragments, either as present on the polypeptide in its native conformation or, in some cases, as present on the polypeptides as denatured, as, e.g., by solubilization in SDS. Among the useful antibody fragments are Fab, Fab', Fv, F(ab')$_2$, and single chain Fv fragments.

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

As is well known in the art, the degree to which an antibody can discriminate as among molecular species in a mixture will depend, in part, upon the conformational relatedness of the species in the mixture; typically, the antibodies will discriminate over adventitious binding to unrelated polypeptides by at least two-fold, more typically by at least 5-fold, typically by more than 10-fold, 25-fold, 50-fold, 75-fold, and often by more than 100-fold, and on occasion by more than 500-fold or 1000-fold.

Typically, the affinity or avidity of an antibody (or antibody multimer, as in the case of an IgM pentamer) for a polypeptide or polypeptide fragment will be at least about $1\times10^{-6}$ M, typically at least about $5\times10^{-7}$ M, usefully at least about $1\times10^{-7}$ M, with affinities and avidities of $1\times10^{-8}$ M, $5\times10^{-9}$ M, $1\times10^{-10}$ M and even stronger proving especially useful.

The isolated antibodies may be naturally-occurring forms, such as IgG, IgM, IgD, IgE, and IgA, from any mammalian species. For example, antibodies are usefully obtained from species including rodents-typically mouse, but also rat, guinea pig, and hamster-lagomorphs, typically rabbits, and also larger mammals, such as sheep, goats, cows, and horses. The animal is typically affirmatively immunized, according to standard immunization protocols, with the polypeptide or polypeptide fragment.

Virtually all fragments of 8 or more contiguous amino acids of the polypeptides may be used effectively as immunogens when conjugated to a carrier, typically a protein such as bovine thyroglobulin, keyhole limpet hemocyanin, or bovine serum albumin, conveniently using a bifunctional linker. Immunogenicity may also be conferred by fusion of the polypeptide and polypeptide fragments to other moieties. For example, peptides can be produced by solid phase synthesis on a branched polylysine core matrix; these multiple antigenic peptides (MAPs) provide high purity, increased avidity, accurate chemical definition and improved safety in vaccine development. See, e.g., Tam et al., *Proc. Natl. Acad. Sci.* USA 85:5409-5413 (1988); Posnett et al., *J. Biol. Chem.* 263, 1719-1725 (1988).

Protocols for immunization are well-established in the art. Such protocols often include multiple immunizations, either with or without adjuvants such as Freund's complete adjuvant and Freund's incomplete adjuvant. Antibodies may be polyclonal or monoclonal, with polyclonal antibodies having certain advantages in immunohistochemical detection of the proteins and monoclonal antibodies having advantages in identifying and distinguishing particular epitopes of the proteins. Following immunization, the antibodies may be produced using any art-accepted technique. Host cells for recombinant antibody production—either whole antibodies, antibody fragments, or antibody derivatives—can be prokaryotic or eukaryotic. Prokaryotic hosts are particularly useful for producing phage displayed antibodies, as is well known in the art. Eukaryotic cells, including mammalian, insect, plant and fungal cells are also useful for expression of the antibodies, antibody fragments, and antibody derivatives. Antibodies can also be prepared by cell free translation.

The isolated antibodies, including fragments and derivatives thereof, can usefully be labeled. It is, therefore, another aspect to provide labeled antibodies that bind specifically to one or more of the polypeptides and polypeptide fragments. The choice of label depends, in part, upon the desired use. In some cases, the antibodies may usefully be labeled with an enzyme. Alternatively, the antibodies may be labeled with colloidal gold or with a fluorophore. For secondary detection using labeled avidin, streptavidin, captavidin or neutravidin, the antibodies may usefully be labeled with biotin. When the antibodies are used, e.g., for Western blotting applications, they may usefully be labeled with radioisotopes, such as $^{33}$P, $^{32}$P, $^{35}$S, $^{3}$H and $^{125}$I. As would be understood, use of the labels described above is not restricted to any particular application.

Methods for Designing Protein Variants

Increased 1-alkene production can be achieved through the expression and optimization of the 1-alkene synthase and the 1-alkene synthesis pathway in organisms well suited for modern genetic engineering techniques, i.e., those that rapidly grow, are capable of thriving on inexpensive food resources and from which isolation of a desired product is easily and inexpensively achieved. To increase the rate of production of 1-alkenes it would be advantageous to design and select variants of the enzymes, including but not limited to, variants optimized for substrate affinity, substrate specificity, substrate catalytic conversion rate, improved thermostability, activity at a different pH and/or optimized codon usage for improved expression in a host cell. See, for example, amino acid changes correlated to alterations in the catalytic rate while maintaining similar affinities (R L Zheng and R G Kemp, *J. Biol. Chem.* (1994) Vol. 269:18475-18479) or amino acid changes correlated with changes in the stability of the transition state that affect catalytic turnover (M A Phillips, et al., *J. Biol. Chem.*, (1990) Vol. 265:20692-20698). It would be another advantage to design and select for enzymes altered to have substantially decreased reverse reaction activity in which enzyme-substrate products would be the result of energetically unfavorable bond formation or molecular re-configuration of the substrate, and have improved forward reaction activity in which enzyme-substrate products would be the result of energetically favorable molecular bond reduction or molecular re-configuration.

Accordingly, one method for the design of improved polyketide synthase proteins for synthesizing 1-nonadecene utilizes computational and bioinformatic analysis to design and select for advantageous changes in primary amino acid sequences encoding ethanologenic enzyme activity. Computational methods and bioinformatics provide tractable alternatives for rational design of protein structure and function. Recently, algorithms analyzing protein structure for biophysical character (for example, motional dynamics and total energy or Gibb's Free Energy evaluations) have become a commercially feasible methodology supplementing protein sequence analysis data that assess homology, identity and/or degree of sequence and domain conservation to improve upon or design the desirable qualities of a protein (Rosetta++, University of Washington). For example, an in silico redesign of the endonuclease I-MsoI was based on computational evaluation of biophysical parameters of rationally selected changes to the primary amino acid sequence. Researchers were able to maintain wild-type binding selectivity and affinity yet improve the catalytic turnover by four orders of magnitude (Ashworth, et al., *Nature* (2006) vol. 441:656-659).

In one embodiment, polypeptide sequences or related homologues in a complex with a substrate are obtained from the Protein Data Bank (PDB; H M Berman, et al., *Nucleic Acids Research* (2000) vol. 28:235-242) for computational analysis on steady state and/or changes in Gibb's free energy relative to the wild type protein. Substitutions of one amino acid residue for another are accomplished in silico interactively as a means for identifying specific residue substitutions that optimize structural or catalytic contacts between the protein and substrate using standard software programs for viewing molecules as is well known to those skilled in the art. To the extent that in silico structures for the polypeptides (and homologues) described herein are available through the PDB, those structures can be used to rationally design modified proteins with desired (typically, improved) activities. Specific amino acid substitutions are rationally chosen based on substituted residue characteristics that optimize, for example, Van der Waal's interactions, hydrophobicity, hydrophilicity, steric non-interferences, pH-dependent electrostatics and related chemical interactions. The overall energetic change of the substitution protein model when unbound and bound to its substrate is calculated and assessed by one having skill in the art to be evaluated for the change in free energy for correlations to overall structural stability (e.g., Meiler, J. and D. Baker, *Proteins* (2006) 65:538-548). In addition, such computational methods provide a means for accurately predicting quaternary protein structure interactions such that in silico modifications are predictive or determinative of overall multimeric structural stability (Wollacott, A M, et al., *Protein Science* (2007) 16:165-175; Joachimiak, L A, et al., *J. Mol. Biol.* (2006) 361:195-208).

Preferably, a rational design change to the primary structure of 1-alkene synthase protein sequences minimally alters the Gibb's free energy state of the unbound polypeptide and maintain a folded, functional and similar wild-type enzyme structure. More preferably a lower computational total free energy change of the protein sequence is achieved to indicate the potential for optimized enzyme structural stability.

Although lower free energy of a protein structure relative to the wild type structure is an indicator of thermodynamic stability, the positive correlation of increased thermal stability to optimized function does not always exist. Therefore, preferably, optimal catalytic contacts between the modified 1-alkene synthase protein structure and the substrate are achieved with a concomitant predicted favorable change in total free energy of the catabolic reaction, for example by rationally designing 1-alkene synthase protein/substrate interactions that stabilize the transition state of the enzymatic reaction while maintaining a similar or favorable change in free energy of the unbound 1-alkene synthase protein for a desired environment in which a host cell expresses the mutant 1-alkene synthase protein. Even more preferably, rationally selected amino acid changes result in a substantially decreased 1-alkene synthase enzyme's anabolic protein/substrate reaction or increase the 1-alkene synthase's catabolic protein/substrate reaction. In a further embodiment any and/or all 1-alkene synthase sequences are expression optimized for the specific expression host cell.

Methods for Generating Protein Variants

Several methods well known to those with skill in the art are available to generate random nucleotide sequence variants for a corresponding polypeptide sequence using the Polymerase Chain Reaction ("PCR") (U.S. Pat. No. 4,683,202). One embodiment is the generation of 1-alkene synthase gene variants using the method of error prone PCR. (R. Cadwell and G. Joyce, *PCR Meth. Appl.* (1991) Vol. 2:28-33; Leung, et al., *Technique* (1989) Vol. 1:11-15). Error prone PCR is achieved by the establishment of a chemical environment during the PCR experiment that causes an increase in unfaithful replication of a parent copy of DNA sought to be replicated. For example, increasing the manganese or magnesium ion content of the chemical admixture used in the PCR experiment, very low annealing temperatures, varying the balance among di-deoxy nucleotides added, starting with a low population of parent DNA templates or using polymerases designed to have increased inefficiencies in accurate DNA replication all result in nucleotide changes in progeny DNA sequences during the PCR replication process. The resultant mutant DNA sequences are genetically engineered into an appropriate vector to be expressed in a host cell and analyzed to screen and select for the desired effect on whole cell production of a product or process of interest. In one embodiment, random mutagenesis of the 1-alkene synthase-encoding nucleotide sequences is generated through error prone PCR using techniques well known to one skilled in the art. Resultant nucleotide sequences are analyzed for structural and functional attributes through clonal screening assays and other methods as described herein.

Another embodiment is generating a specifically desired protein mutant using site-directed mutagenesis. For example, with overlap extension (An, et al., *Appl. Microbiol. Biotech.* (2005) vol. 68(6):774-778) or mega-primer PCR (E. Burke and S. Barik, *Methods Mol. Bio.* (2003) vol 226:525-532) one can use nucleotide primers that have been altered at corresponding codon positions in the parent nucleotide to yield DNA progeny sequences containing the desired mutation. Alternatively, one can use cassette mutagenesis (Kegler-Ebo, et al., *Nucleic Acids Res.* (1994) vol. 22(9):1593-1599) as is commonly known by one skilled in the art.

In one aspect, using site-directed mutagenesis and cassette mutagenesis, all possible positions in SEQ ID NO:2 are changed to a proline, transformed into a suitable high expression vector and expressed at high levels in a suitable expression host cell. Purified aliquots at concentrations necessary for the appropriate biophysical analytical technique are obtained by methods as known to those with skill in the art (P. Rellos and R. K. Scopes, *Prot. Exp. Purific.* (1994) Vol. 5:270-277) and evaluated for increased thermostability.

Another embodiment is to select for a polypeptide variant for expression in a recipient host cell by comparing a first nucleic acid sequence encoding the polypeptide with the nucleic acid sequence of a second, related nucleic acid sequence encoding a polypeptide having more desirable qualities, and altering at least one codon of the first nucleic acid sequence to have identity with the corresponding codon of the second nucleic acid sequence, such that improved polypeptide activity, substrate specificity, substrate affinity, substrate catalytic conversion rate, improved thermostability, activity at a different pH and/or optimized codon usage for expression and/or structure of the altered polypeptide is achieved in the host cell.

In yet another embodiment, all amino acid residue variations are encoded at any desired, specified nucleotide codon position using such methods as site saturation mutagenesis (Meyers, et al., *Science* (1985) Vol. 229:242-247; Derbyshire, et al., *Gene* (1986) Vol. 46:145-152; U.S. Pat. No. 6,171,820). Whole gene site saturation mutagenesis (K. Kretz, et al., *Meth. Enzym.* (2004) Vol. 388:3-11) is preferred wherein all amino acid residue variations are encoded at every nucleotide codon position. Both methods yield a population of protein variants differing from the parent polypeptide by one amino acid, with each amino acid substitution being correlated to structural/functional attributes at any position in the polypeptide. Saturation mutagenesis uses PCR and primers homologous to the parent sequence wherein one or more codon encoding nucleotide triplets is randomized. Randomization results in the incorporation of codons corresponding to all amino acid replacements in the final, translated polypeptide. Each PCR product is genetically engineered into an expression vector to be introduced into an expression host and screened for structural and functional attributes through clonal screening assays and other methods as described herein.

In one aspect of saturation mutagenesis, correlated saturation mutagenesis ("CSM") is used wherein two or more amino acids at rationally designated positions are changed concomitantly to different amino acid residues to engineer improved enzyme function and structure. Correlated saturation mutagenesis allows for the identification of complimentary amino acid changes having, e.g., positive, synergistic effects on 1-alkene synthase enzyme structure and function. Such synergistic effects include, but are not limited to, significantly altered enzyme stability, substrate affinity, substrate specificity or catalytic turnover rate, independently or concomitantly increasing advantageously the production of 1-alkenes.

In yet another embodiment, amino acid substitution combinations of CSM derived protein variants being optimized for a particular function are combined with one or more CSM derived protein variants being optimized for another particular function to derive a 1-alkene synthase and/or A1174 hydrolase protein variant exhibiting multiple optimized structural and functional characteristics. For example, amino acid changes in combinatorial mutants showing optimized protomer interactions are combined with amino acid changes in combinatorial mutants showing optimized catalytic turnover.

In one embodiment, mutational variants derived from the methods described herein are cloned. DNA sequences produced by saturation mutagenesis are designed to have restriction sites at the ends of the gene sequences to allow for excision and transformation into a host cell plasmid. Generated plasmid stocks are transformed into a host cell and incubated at optimal growth conditions to identify successfully transformed colonies.

Another embodiment utilizes gene shuffling (P. Stemmer, *Nature* (1994) Vol. 370:389-391) or gene reassembly (U.S. Pat. No. 5,958,672) to develop improved protein structure/function through the generation of chimeric proteins. With gene shuffling, two or more homologous 1-alkene synthases encoding nucleotide sequences are treated with endonucleases at random positions, mixed together, heated until sufficiently melted and reannealed. Nucleotide sequences from homologues will anneal to develop a population of chimeric genes that are repaired to fill in any gaps resulting from the re-annealing process, expressed and screened for improved structure/function 1-alkene synthase chimeras. Gene reassembly is similar to gene shuffling; however, nucleotide sequences for specific, homologous 1-alkene synthase protein domains are targeted and swapped with other homologous domains for reassembly into a chimeric gene. The genes are expressed and screened for improved structure/function 1-alkene synthase chimeras.

In a further embodiment any and/or all sequences additionally are expression optimized for the specific expression host cell.

Methods for Measuring Protein Variant Efficacy

Variations in expressed polypeptide sequences may result in measurable differences in the whole-cell rate of substrate conversion. It is desirable to determine differences in the rate of substrate conversion by assessing productivity in a host cell having a particular protein variant relative to other whole cells having a different protein variant. Additionally, it would be desirable to determine the efficacies of whole-cell substrate conversion as a function of environmental factors including, but not limited to, pH, temperature nutrient concentration and salinity.

Therefore, in one embodiment, the biophysical analyses described herein on protein variants are performed to measure structural/functional attributes. Standard analyses of polypeptide activity are well known to one of ordinary skill in the art. Such analysis can require the expression and high purification of large quantities of polypeptide, followed by various physical methods (including, but not limited to, calorimetry, fluorescence, spectrophotometric, spectrometric, liquid chromatography (LC), mass spectrometry (MS), LC-MS, affinity chromatography, light scattering, nuclear magnetic resonance and the like) to assay function in a specific environment or functional differences among homologues.

In another embodiment, the polypeptides are expressed, purified and subject to the aforementioned analytical techniques to assess the functional difference among polypeptide sequence homologues, for example, the rate of substrate conversion and/or 1-alkene synthesis.

Batch culture (or closed system culture) analysis is well known in the art and can provide information on host cell population effects for host cells expressing genetically engineered genes. In batch cultures a host cell population will grow until available nutrients are depleted from the culture media.

In one embodiment, the polypeptides are expressed in a batch culture and analyzed for approximate doubling times, expression efficacy of the engineered polypeptide and end-point net product formation and net biomass production.

Turbidostats are well known in the art as one form of a continuous culture within which media and nutrients are provided on an uninterrupted basis and allow for non-stop propagation of host cell populations. Turbidostats allow the user to determine information on whole cell propagation and steady-state productivity for a particular biologically produced end product such as host cell doubling time, temporally delimited biomass production rates for a particular host cell population density, temporally delimited host cell population density effects on substrate conversion and net productivity of a host cell substrate conversion. Turbidostats can be designed to monitor the partitioning of substrate conversion products to the liquid or gaseous state. Additionally, quantitative evaluation of net productivity of a carbon-based product of interest can be accurately performed due to the exacting level of control that one skilled in the art has over the operation of the turbidostat. These types of information are useful to assess the parsed and net efficacies of a host cell genetically engineered to produce a specific carbon-based product of interest.

In one embodiment, identical host cell lines differing only in the nucleic acid and expressed polypeptide sequence of a homologous enzyme are cultured in a uniform-environment turbidostat to determine highest whole cell efficacy for the desired carbon-based product of interest.

In another embodiment, identical host cell lines differing only in the nucleic acid and expressed polypeptide sequence of a homologous enzyme are cultured in a batch culture or a turbidostat in varying environments (e.g. temperature, pH, salinity, nutrient exposure) to determine highest whole cell efficacy for the desired carbon-based product of interest.

In one embodiment, mutational variants derived from the methods described herein are cloned. DNA sequences produced by saturation mutagenesis are designed to have restriction sites at the ends of the gene sequences to allow for cleavage and transformation into a host cell plasmid. Generated plasmid stocks are transformed into a host cell and incubated at optimal growth conditions to identify successfully transformed colonies.

Methods for Producing 1-nonadecene

It is desirable to engineer into an organism better suited for industrial use a genetic system from which 1-nonadecene can be produced efficiently and cleanly.

Accordingly, the invention includes the conversion of water, carbon dioxide and light into 1-alkenes using the 1-alkene synthase enzyme described herein. In one embodiment, the invention includes producing 1-alkenes, including 1-nonadecene and 1-octadecene, using genetically engineered host cells expressing a 1-alkene synthase gene.

In another preferred embodiment, the genetically engineered host cells expresses a 1-alkene synthase and one or more genes in a 1-alkene biosynthetic pathway enabling the host cell to convert water, light and carbon dioxide and/or stearic acid into 1-nonadecene.

In another embodiment of the invention, the genetically engineered host cell is processed into an enzymatic lysate for performing the above conversion reaction. In yet another embodiment, the 1-alkene synthase gene product is purified, as described herein, for carrying out the conversion reaction.

The host cells and/or enzymes, for example in the lysate, partially purified, or purified, used in the conversion reactions are in a form allowing them to perform their intended function, producing a desired compound, for example, 1-nonadecene. The microorganisms used can be whole cells, or can be only those portions of the cells necessary to obtain the desired end result. The microorganisms can be suspended (e.g., in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeabilized (e.g., have permeabilized membranes and/or walls such that compounds, for example, substrates, intermediates or products can more easily pass through said membrane or wall).

In yet another embodiment, a purified or unpurified 1-alkene synthesizing enzyme (e.g., a 1-alkene synthase) is used in the conversion reactions. The enzyme is in a form that allows it to perform its intended function. For example, the enzyme can be immobilized, conjugated or floating freely.

In yet another embodiment the 1-alkene synthase enzymes are chimeric wherein a polypeptide linker is encoded between the polyketide synthase enzyme and another enzyme. Upon translation into a polypeptide, two enzymes of a metabolic pathway are tethered together by a polypeptide linker. Such arrangement of two or more functionally related proteins tethered together in a host cell increases the local effective concentration of metabolically related enzymes that can increase the efficiency of substrate conversion.

The following examples are for illustrative purposes and are not intended to limit the scope of the invention.

Example 1

Increase Yields of a 1-alkene Via a Gene Knockout in a Cyanobacterium

Three vectors were constructed so that gene knockout strains of *Synechococcus* sp. PCC7002 could be prepared for nonA (SYNPCC7002_A1173), an upstream putative hydrolase gene (SYNPCC7002_A1174) and an unrelated gene to use as a marker control strain (SYNPCC7002_A1189). These plasmids contain approximately 750 bp of upstream and downstream sequence for the respective gene flanking a gentamycin resistance marker. The DNA sequences of these plasmids are given in SEQ ID NO: 5, SEQ ID NO: 6 and SEQ ID NO: 7, respectively.

Strain Construction:

The knockout strains of *Synechococcus* sp. PCC 7002 were prepared using the following procedure. A 5 ml culture of in A+ medium containing 200 mg/L spectinomycin was incubated in an Infors shaking incubator at 150 rpm at 37° C. under 2% $CO_2$/air and continuous light (70-130 µE m2/s PAR, measured with a LI-250A light meter (LI-COR)) until it reached an $OD_{730}$ of 1. A+ medium comprises 18.0 g/L sodium chloride, 5.0 g/L magnesium sulfate heptahydrate, 1.0 g/L sodium nitrate, 1.0 g/L Tris, 0.6 g/L potassium chloride, 0.3 g/L calcium chloride (anhydrous), 50 mg/L potassium phosphate monobasic, 34.3 mg/L boric acid, 29.4 mg/L EDTA (disodium salt dihydrate), 3.9 mg/L iron (III) chloride hexahydrate, 4.3 mg/L manganese chloride tetrahydrate, 315.0 µg/L zinc chloride, 30.0 µg/L molybdenum (VI) oxide, 12.2 µg/L cobalt (II) chloride hexahydrate, 10.0 µg/L vitamin $B_{12}$, and 3.0 µg/L copper (II) sulfate pentahydrate. For each plasmid, 500 µl of culture and 5 µg of plasmid DNA were added into a microcentrifuge tube. The tubes were then incubated at 37° C. in New Brunswick shaking incubator at 250 rpm in the dark for 4 h. 250 µl for each transformation was then plated on A+ agar plates. The plates were incubated overnight in a Percival lighted incubator under constant illumination (40-60 µE/m2/s PAR, measured with a LI-250A light meter (LI-COR)) at 37° C. for about 24 hours. On the following day, a gentamycin solution was added underneath the agar of the plates to a final estimated concentration of 25 mg/L gentamycin (assuming 40 ml A+ agar in the plate). These plates were placed back into the incubator until tiny colonies became visible. The plates were moved to another Percival incubator under the same conditions except that 1% $CO_2$ was maintained in the air (allows for faster growth). Two colonies from each transformation plate were streaked onto A+ plates containing 50 mg/L gentamycin and incubated in a Percival incubator (ambient $CO_2$ concentration) until colonies were present. This plating step was repeated, and segregated strains with the respective genes removed (Table 1) were identified by PCR screening with primers designed to probe for the presence of the respective genes.

TABLE 1

Strains investigated for the production of 1-alkenes.

| JCC # | Parent strain | Genotype | Marker |
|---|---|---|---|
| JCC138 | NA | *Synechococcus* sp. PCC 7002 | NA |
| JCC1129 | JCC138 | ΔA1189 (type II site-specific deoxyribonuclease) | gentamycin |
| JCC1218 | JCC138 | ΔA1173 (nonA) | gentamycin |
| JCC1219 | JCC138 | ΔA1174 (hydrolase domain-containing protein) | gentamycin |

Culturing Conditions

One 30-ml culture of each strain listed in Table 1 was prepared in JB 2.1 medium (see, e.g., PCT US2009/006516, published Jun. 17, 2010) at an $OD_{730}$=0.2 in 125 ml flasks (inocula were from five ml A+ cultures containing 200 mg/L spectinomycin started from colonies incubated for 3 days in a Multitron II Infors shaking photoincubator under continuous light of ~100 µE $m^{-2}s^{-1}$ photosynthetically active radiation (PAR) at 37° C. at 150 rpm in 2% $CO_2$-enriched air). The cultures were incubated for four days in the Infors incubators under continuous light of ~100 µE $m^{-2}s^{-1}$ photosynthetically active radiation (PAR) at 37° C. at 150 rpm in 2% $CO_2$-enriched air. Water loss was compensated by adding back milli-Q water (based on weight loss of flasks). Optical density measurements at 730 nm ($OD_{730}$) were taken (Table 2). 2.5 ml of each culture was removed and the cells were pelleted using a Sorvall RC6 Plus superspeed centrifuge (Thermo Electron Corp) and a F13S-14X50CY rotor (5000 rpm for 10 min). The media supernatant was removed and the cells were resuspended in 1 ml of Milli-Q water. The cells were pelleted again using a benchtop centrifuge, the supernatant discarded and the cell pellets were stored at −80° C. until analyzed for the presence of 1-nonadecene.

Detection and Quantification of 1-nonadecene in Strains

Cell pellets were thawed and 1 ml aliquots of acetone (Acros Organics 326570010) containing 100 mg/L butylated hydroxytoluene (Sigma-Aldrich B1378) and 50 mg/L ethyl arachidate (Sigma A9010) were added. The cell pellets were vortexed twice for 15 seconds (total extraction time of 1-2 min). The suspensions were centrifuged for 2 min to pellet debris, and the supernatants analyzed with a gas chromatograph using flame ionization detection (GC/FID) or a mass spectral detection (GC/MS).

An Agilent 7890A GC/5975C EI-MS equipped with a 7683 series autosampler was used to confirm the identification of 1-nonadecene. One µL of each sample was injected into the GC inlet using pulsed splitless injection (pressure: 20 psi, pulse time: 0.3 min, purge time: 0.2 min, purge flow: 15 mL/min) and an inlet temperature of 280° C. The column was a HP-5MS (Agilent, 30 m×0.25 mm×0.25 µm) and the carrier gas was helium at a flow of 1.0 mL/min. The GC oven temperature program was 50° C., hold one minute; 10°/min increase to 280° C.; hold ten minutes. The GC/MS interface was 290° C., and the MS range monitored was 25 to 600 amu. A peak was present in the extract of JCC138 which had the same retention time (17.5 min) and mass spectrum (FIG. 4) as a commercially available standard of 1-nonadecene (Fluka 74320) confirming the production of the 1-alkene by this strain.

An Agilent 7890A GC/FID equipped with a 7683 series autosampler was used to quantify 1-nonadecene. One microliter of each sample was injected into the GC inlet (split 5:1, pressure: 20 psi, pulse time: 0.3 min, purge time: 0.2 min, purge flow: 15 mL/min), which was at a temperature of 280° C. The column was an HP-5MS (Agilent, 30 m×0.25 mm×0.25 µm), and the carrier gas was helium at a flow of 1.0 mL/min. The GC oven temperature program was 50° C., hold one minute; 10°/min increase to 280° C.; hold ten minutes. A calibration curve was constructed using the 1-nonadecene standard (rt 18.8), and the concentrations in the extracts were determined and normalized to the concentration of ethyl arachidate (internal standard).

Deletion of nonA in *Synechococcus* sp. PCC7002 abolishes production of 1-nonadecene, confirming that the gene is essential for the production of the alkene (FIG. 5). JCC1219 (Δhydrolase) produced approximately 3× more 1-nonadecene than JCC138 and JCC1129 strains (FIG. 5; Table 2). This demonstrates that JCC138 can be engineered to overproduce 1-alkenes.

TABLE 2

The $OD_{730}$ and % dry cell weights (DCWs) of 1-nonadecene in various cultures

| Strain | Genotype | $OD_{730}$ | 1-nonadecene (% DCW*) |
|---|---|---|---|
| JCC138 | Wild type | 11.8 | 0.25 |
| JCC1129 | Δ ribonuclease | 11.4 | 0.26 |
| JCC1218 | Δ nonA | 9.1 | None detected |
| JCC1219 | Δ hydrolase | 11.5 | 0.75 |

*The DCWs were estimated based on the OD measurement using an experimentally determined average of 300 mg $L^{-1}$ $OD_{730}^{-1}$.

Example 2

Production of Shorter Olefins by NonA

Three 30-ml cultures of JCC138 was prepared in JB 2.1 at an $OD_{730}$=0.07 in 125 ml flasks (inocula were from five ml A+ cultures containing 200 mg/L spectinomyin started from colonies incubated for 3 days in a Multitron II Infors shaking photoincubator under continuous light of ~100 µE $m^{-2}s^{-1}$ photosynthetically active radiation (PAR) at 37° C. at 150 rpm in 2% $CO_2$-enriched air). The cultures were incubated for three days in the Infors incubators under continuous light of ~100 µE $m^{-2}s^{-1}$ photosynthetically active radiation (PAR) at 37° C. at 150 rpm in 2% $CO_2$-enriched air. All three cultures had an $OD_{730}$=6.2. 2.8 mg of tridecanoic acid (Fluka 91988) in 75 µl of ethanol was added to one flask and 11.2 mg of the fatty acid was added to another flask in the same volume of ethanol. 75 µl of ethanol was added to the third flask as a control. The cultures were placed back in the Infors and incubated for a total of 231.8 h. Optical density measurements at 730 nm ($OD_{730}$) were taken (Table 3), and cell pellet samples were taken for dry cell weight determination and for 1-alkene extraction. The acetone extraction and GC analysis was performed as described in Example 1.

Examination of the GC/FID chromatograms revealed the presence of several new peaks in the tridecanoic acid-fed cultures (FIG. 6). Analysis of the extracts by GC/MS allowed the identification of one of these peaks as 1-octadecene (r.t. 17.8 in FIG. 6). This was done by matching the experimentally determined mass spectrum associated with the peak with mass spectral matches found by searching in a NIST 08 MS database (FIG. 7). Quantification of the 1-octadecene was carried out by estimating a response factor from the experimentally-determined response factor for 1-nonadecene. After identification of 1-octadecene from the cultures incubated with the tridecanoic acid, examination of the JCC138 spectral data revealed that low amounts of 1-octadecene are produced by JCC138. The ratio of 1-octadecene to 1-nonadecene and % DCWs found in the JCC138 cultures are given in Table 3.

TABLE 3

$OD_{730}$ and % DCWs of 1-octadecene and 1-nonadecene following tridecanoic acid (FA) feeding

| Culture | $OD_{730}$ | 1-octadecene:1-nonadecene* | % DCW 1-octadecene | % DCW 1-nonadecene |
|---|---|---|---|---|
| JCC138 | 23.6 | 1:140.9 | 0.0018 | 0.27 |
| JCC138 + 2.8 mg FA | 22.3 | 1:7.48 | 0.023 | 0.18 |
| JCC138 + 11.2 mg FA | 20.1 | 1:1.87 | 0.039 | 0.077 |

*The molar ratio of 1-octadecene to 1-nonadecene is indicated.

Example 3

Cloning of nonA and Expression of 1-alkene Synthase

Cloning of nonA (SYNPCC7002_A1173)

A preferred cloning method is to synthesize nonA and/or the A1174 hydrolase based on nucleotide sequences retrieved from BLAST searches, and optionally including changes to the sequence that reflect desired optimization of expression, enzyme structure or enzyme function. Synthesized 1-alkene synthase and/or A1174 hydrolase genes can be acquired from, for example, DNA2.0 (Menlo Park, Calif.). Alternatively, PCR can be used to amplify the genes using, e.g., JCC1138 or a cyanobacteria comprising a homologous gene as a source. Several other strategies may be used for cloning the genes into a suitable host as described in Ausubel, et al., Current Protocols in Molecular Biology (Green Pub. Assoc. and Wiley Intersciences, N.Y. 1993) and Sambrook, et al., Molecular Cloning: A Laboratory Manual (Cold Spring Harbor, N.Y. 2nd ed. 1989).

Plasmid pJB5 was designed as an empty expression vector for recombination into *Synechococcus* sp. PCC 7002. Two regions of homology, the Upstream Homology Region (UHR) and the Downstream Homology Region (DHR) were designed to flank the construct. These 500 bp regions of homology correspond to positions 3301-3800 and 3801-4300 (Genbank Accession NC_005025) for the UHR and DHR, respectively. The aadA promoter, gene sequence, and terminator were designed to confer spectinomycin and streptomycin resistance to the integrated construct. For expression, pJB5 was designed with the aph2 kanamycin resistance cassette promoter and ribosome binding site (RBS). Downstream of this promoter and RBS, restriction endonuclease recognition sites are designed and inserted for NdeI and EcoRI, as well as the sites for XhoI, BamHI, SpeI and PacI. Following the EcoRI site, the natural terminator from the pyruvate decarboxylase gene from *Zymomonas mobilis* (pdc) terminator is included. Convenient XbaI restriction sites flank the UHR and DHR, allowing cleavage of the DNA intended for recombination from the rest of the vector. pJB5 was constructed by DNA2.0 (Menlo Park, Calif.).

Construction of pJB5-NonA Vector

The 1-alkene synthase from JCC138 is cloned into the pJB5 plasmid using standard procedures. Constructs are transformed into high efficiency NEB 5-α F'Iq competent *E. coli* cells (New England BioLabs, Ipswitch, Mass.). The genes are expressed in *E. coli* and 1-nonadecene is produced.

Genetically Modified *Synechococcus* sp. PCC 7002

The pJB5-NonA construct is cloned into *Synechococcus* sp. PCC 7002 using the following protocol. *Synechococcus* 7002 is grown for 48 hours from colonies in an incubated shaker flask at 30° C. at 1% $CO_2$ to an $OD_{730}$ of 1 in $A^+$ medium described in Frigaard N U et al. (2004) "Gene inactivation in the cyanobacterium *Synechococcus* sp. PCC 7002 and the green sulfur bacterium *Chlorobium tepidum* using in vitro-made DNA constructs and natural transformation" Methods Mol Biol 274:325-340. 500 µL of culture is added to a test-tube with 30 µL of 1-5 µg of DNA prepped from a Qiagen Qiaprep Spin Miniprep Kit (Valencia, Calif.) for each construct. Cells are incubated bubbling in 1% $CO_2$ at approximately 1 bubble every 2 seconds for 4 hours. 200 µL of cells are plated on $A^+$ medium plates with 1.5% agarose and grown at 30° C. for two days in low light. 10 µg/mL of spectinomycin is underplayed on the plates. Resistant colonies are visible in 7-10 days.

In another embodiment, stronger promoters and/or constitutive and/or inducible promoters are placed in front of nonA and higher production of 1-nonadecene (and/or other 1-alkenes) is observed relative to that in otherwise identical strains lacking the stronger, constitutive and/or inducible promoters. In another embodiment, the copy number of nonA in the cell is increased by at least duplicating the gene in the chromosome, and higher production of 1-nonadecene (and/or other 1-alkenes) is observed relative to that in otherwise identical strains lacking the duplicated gene.

Complete cites to various articles referred to herein are provided below:

Goodloe, R. S. and Light, R. J. 1982. Structure and composition of hydrocarbons and fatty acids from a marine blue-green alga, *Synechococcus* sp. Biochimica et Biophysica Acta 710: 485-492.

Gu, L., Wang, B., Kulkarni, A., Gehret, J. J., Lloyd, K. R., Gerwick, L., Gerwick, W. H., Wipf, P., Håkannson, K., Smith, J. L. and Sherman, D. H. 2009. Polyketide decarboxylative chain termination preceded by O-sulfonation in curacin A biosynthesis. Journal of the American Chemical Society 131: 16033-16035.

Higashi, S. and Murata, N. 1993. An in vivo study of substrate specificities of acyl-lipid desaturases and acyltransferases in lipid synthesis in *Synechocystis* PCC6803. Plant Physiology 102:1275-1278.

Kaczmarzyk, D. and Fulda, M. 2010. Fatty acid activation in cyanobacteria mediated by acyl-acyl carrier protein synthetase enables fatty acid recycling. Plant Physiology 152: 1598-1610.

Lin, J.-W., Chao, Y-.F. and Weng, S.-F. 1996. Nucleotide sequence and functional analysis of the luxE gene encoding acyl-protein synthetase of the lux operon from *Photobacterium leiognathi. Biochemical and Biophysical Research Communications 228: 764-773.

Williams, J. P., Maissan, E., Mitchell, K. and Khan, J. P. 1990. The manipulation of the fatty acid composition of glycerolipids in cyanobacteria using exogenous fatty acids. Plant Cell Physiology 31:495-503.

Winters, K., Parker, P. L. and Van Baalen, C. 1969. Hydrocarbons of Blue-Green Algae: Geochemical Significance. Science 163: 467-468.

All publications, patents and other references mentioned herein are hereby incorporated by reference in their entireties and for all purposes.

```
INFORMAL SEQUENCE LISTING
>SYNPCC7002_A1173 1-alkene synthase (PKS) [Synechococcus sp. PCC 7002]
                                                           SEQ ID NO. 1
ATGGTTGGTCAATTTGCAAATTTCGTCGATCTGCTCCAGTACAGAGCTAAACTTCAGGCGCGGAAAACCG

TGTTTAGTTTTCTGGCTGATGGCGAAGCGGAATCTGCGGCCCTGACCTACGGAGAATTAGACCAAAAAGC

CCAGGCGATCGCCGCTTTTTTGCAAGCTAACCAGGCTCAAGGGCAACGGGCATTATTACTTTATCCACCG

GGTTTAGAGTTTATCGGTGCCTTTTTGGGATGTTTGTATGCTGGTGTTGTTGCGGTGCCAGCTTACCCAC

CACGGCCGAATAAATCCTTTGACCGCCTCCATAGCATTATCCAAGATGCCCAGGCAAAATTTGCCCTCAC

CACAACAGAACTTAAAGATAAAATTGCCGATCGCCTCGAAGCTTTAGAAGGTACGGATTTTCATTGTTTG

GCTACAGATCAAGTTGAATTAATTTCAGGAAAAAATTGGCAAAAACCGAACATTTCCGGCACAGATCTCG

CTTTTTTGCAATACACCAGTGGCTCCACGGGCGATCCTAAAGGAGTGATGGTTTCCCACCACAATTTGAT

CCACAACTCCGGCTTGATTAACCAAGGATTCCAGGATACAGAGGCGAGTATGGGCGTTTCCTGGTTGCCG

CCCTACCATGATATGGGCTTGATCGGTGGATTTTACAGCCCATCTATGTGGGAGCAACGCAAATTTTAA

TGCCTCCCGTGGCCTTTTTGCAGCGACCTTTTCGGTGGCTAAAGGCGATCAACGATTATCGGGTTTCCAC

CAGCGGTGCGCCGAATTTTGCCTATGATCTCTGTGCCAGCCAAATTACCCCGGAACAAATCAGAGAACTC

GATTTGAGCTGTTGGCGACTGGCTTTTTCCGGGGCCGAACCGATCCGCGCTGTGACCCTCGAAAATTTTG

CGAAAACCTTCGCTACAGCAGGCTTTCAAAAATCAGCATTTTATCCCTGTTATGGTATGGCTGAAACCAC

CCTGATCGTTTCCGGTGGTAATGGTCGTGCCCAGCTTCCCCAGGAAATTATCGTCAGCAAACAGGGCATC

GAAGCAAACCAAGTTCGCCCTGCCCAAGGGACAGAAACAACGGTGACCTTGGTCGGCAGTGGTGAAGTGA

TTGGCGACCAAATTGTCAAAATTGTTGACCCCCAGGCTTTAACAGAATGTACCGTCGGTGAAATTGGCGA

AGTATGGGTTAAGGGCGAAAGTGTTGCCCAGGGCTATTGGCAAAAGCCAGACCTCACCCAGCAACAATTC

CAGGGAAACGTCGGTGCAGAAACGGGCTTTTTACGCACGGGCGATCTGGGTTTTTTGCAAGGTGGCGAAC

TGTATATTACGGGTCGTTTAAAGGATCTCCTGATTATCCGGGGGCGCAACCACTATCCCCAGGACATTGA

ATTAACCGTCGAAGTGGCCCATCCCGCTTTACGACAGGGGGCCGGAGCCGCTGTATCAGTAGACGTTAAC

GGGGAAGAACAGTTAGTCATTGTCCAGGAAGTTGAGCGTAAATATGCCCGCAAATTAAATGTCGCGGCAG

TAGCCCAAGCTATTCGTGGGCGATCGCCGCCGAACATCAACTGCAACCCCAGGCCATTTGTTTTATTAA

ACCCGGTAGCATTCCCAAAACATCCAGCGGGAAGATTCGTCGCCATGCCTGCAAAGCTGGTTTTCTAGAC

GGAAGCTTGGCTGTGGTTGGGGAGTGGCAACCCAGCCACCAAAAAGAAGGAAAAGGAATTGGGACACAAG

CCGTTACCCCTTCTACGACAACATCAACGAATTTTCCCCTGCCTGACCAGCACCAACAGCAAATTGAAGC

CTGGCTTAAGGATAATATTGCCCATCGCCTCGGCATTACGCCCCAACAATTAGACGAAACGGAACCCTTT

GCAAGTTATGGGCTGGATTCAGTGCAAGCAGTACAGGTCACAGCCGACTTAGAGGATTGGCTAGGTCGAA

AATTAGACCCCACTCTGGCCTACGATTATCCGACCATTCGCACCCTGGCTCAGTTTTTGGTCCAGGGTAA

TCAAGCGCTAGAGAAAATACCACAGGTGCCGAAAATTCAGGGCAAAGAAATTGCCGTGGTGGGTCTCAGT

TGTCGTTTTCCCCAAGCTGACAACCCCGAAGCTTTTTGGGAATTATTACGTAATGGTAAAGATGGAGTTC

GCCCCCTTAAAACTCGCTGGGCCACGGGAGAATGGGGTGGTTTTTTAGAAGATATTGACCAGTTTGAGCC

GCAATTTTTTGGCATTTCCCCCGGGAAGCGGAACAAATGGATCCCCAGCAACGCTTACTGTTAGAAGTA

ACCTGGGAAGCCTTGGAACGGGCAAATATTCCGGCAGAAAGTTTACGCCATTCCCAAACGGGGGTTTTG

TCGGCATTAGTAATAGTGATTATGCCCAGTTGCAGGTGCGGGAAAACAATCCGATCAATCCCTACATGGG
```

-continued

```
GACGGGCAACGCCCACAGTATTGCTGCGAATCGTCTGTCTTATTTCCTCGATCTCCGGGCGTTTCTCTG

AGCATCGATACGGCCTGTTCCTCTTCTCTGGTGGCGGTACATCTGGCCTGTCAAAGTTTAATCAACGGCG

AATCGGAGTTGGCGATCGCCGCCGGGGTGAATTTGATTTTGACCCCCGATGTGACCCAGACTTTTACCCA

GGCGGGCATGATGAGTAAGACGGGCCGTTGCCAGACCTTTGATGCCGAGGCTGATGGCTATGTGCGGGGC

GAAGGTTGTGGGGTCGTTCTCCTCAAACCCCTGGCCCAGGCAGAACGGGACGGGGATAATATTCTCGCGG

TGATCCACGGTTCGGCGGTGAATCAAGATGGACGCAGTAACGGTTTGACGGCTCCCAACGGGCGATCGCA

ACAGGCCGTTATTCGCCAAGCCCTGGCCCAAGCCGGCATTACCGCCGCCGATTTAGCTTACCTAGAGGCC

CACGGCACCGGCACGCCCCTGGGTGATCCCATTGAAATTAATTCCCTGAAGGCGGTTTTACAAACGGCGC

AGCGGGAACAGCCCTGTGTGGTGGGTTCTGTGAAAACAAACATTGGTCACCTCGAGGCAGCGGCGGGCAT

CGCGGGCTTAATCAAGGTGATTTTGTCCCTAGAGCATGGAATGATTCCCCAACATTTGCATTTTAAGCAG

CTCAATCCCCGCATTGATCTAGACGGTTTAGTGACCATTGCGAGCAAAGATCAGCCTTGGTCAGGCGGGT

CACAAAAACGGTTTGCTGGGGTAAGTTCCTTTGGGTTTGGTGGCACCAATGCCCACGTGATTGTCGGGGA

CTATGCTCAACAAAAATCTCCCCTTGCTCCTCCGGCTACCCAAGACCGCCCTTGGCATTTGCTGACCCTT

TCTGCTAAAAATGCCCAGGCCTTAAATGCCCTGCAAAAAAGCTATGGAGACTATCTGGCCCAACATCCCA

GCGTTGACCCACGCGATCTCTGTTTGTCTGCCAATACCGGGCGATCGCCCCTCAAGAACGTCGTTTTTTT

GTCTTTAACAAGTCGCCGATTTACAACAACTCTCAATCAAGATTTTCTGGCCCAACCACGCCTCAGTTCC

CCCGCAATTGCCTTTTTGTTTACGGGGCAAGGTTCCCAATACTACGGCATGGGGCAACAACTGTACCAAC

CAGCCCAGTATTTCGGCAAGTGCTGGATGAGTGCGATCGCCTCTGGCAGACCTATTCCCCGAAGCCCCT

GCCCTCACCGACCTGCTGTACGGTAACCATAACCCTGACCTCGTCCACGAACTGTCTATACCCAGCCCCT

CCTCTTTGCTGTTGAATATGCGATCGCCCAACTATGGTTAAGCTGGGGCGTGACGCCAGACTTTTGCATG

GGCCATAGCGTCGGCGAATATGTCGCGGCTTGTCTGGCGGGGTATTTTCCCTGGCAGACGGCATGAATT

AATTACGGCCCGGGGCAACTGATGCACGCCCTACCCAGCAATGGCAGTATGGCGGCGGTCTTTGCCGATA

ACGGTCATCAACCCTACCTATCGGAGCATTTGACCGTCGGAGCCGAACGGTTCCCATTTGGTGCTATCAG

GAAGACCCCCTGCCTCGAAGCCAGTATTCACAACTCCAAGCCAAGGGATCAAAACCAACCCCTCAAGGTT

TCCCATGCTTTCCACTCCCCTTTGATGGCTCCCATGCTGGCAGAGTTTCGGGAATTGCTGAACAATTACT

TTCCACCCGCCGCGTATCCCGCTCATTTCCAATGTCACGGGCGGCCAGATTGAAGCGGAATTGCCCAGGC

CGACTATTGGGTTAAGCACGTTTCGCAACCCGTCAATTTGTCCAGAGCATCCAAACCCTGGCCCAAGCGG

GTGTCAATGTTTATCTCGAAATCGGCGTAAAACCAGTGCTCCTGAGTATGGGACGCCATTGCTTAGCTGA

ACAAGAAGCGGTTTGGTTGCCCAGTTTACGTCCCCATAGTGAGCCTTGGCCGGAATTTTGACCAGTCTCG

GCAACTGTATGAGCAAGGGCTAACATTGACTGGCAGACCGTGGAAGCTGGCGATCGCCGCCGGAACTGAT

TCTGCCCACCTATCCCTTCCAACGGCAACGATATTGGTTTAATCAAGGCTCTTGGCAACTGTTGAGACCG

AATCTGTGAACCCAGGCCCTGACGATCTCAATGATTGGTTGTATCAGGTGGCGTGGACGCCCCTGGACAC

TTTGCCCCCGGCCCCTGAACCGTCGGCTAAGCTGTGGTTAATCTTGGGCGATCGCCATGATCACCAGCCC

ATTGAAGCCCAATTTAACGCCCAGCGGGTGTATCTCGGCCAAGCAATCATTTTCCGACGAATGCCCCCTG

GGAAGTATCTGCCGATGCGTTGGATAATTTATTTACTCACGTCGGCTCCCAATTTAGCAGGCATCCTTTA

CCTGTGTCCCCAGGGGAAGACCCAGAAGACCTAGAGTTCCCTGCTGGTTTGTGACCCACCAGAGCCAAC

GGGTGCTTGAACCGATGCTGTCACCGGATTTGCCCAAGGGGGATTATGGGGACTCGCCCAGGCGATCGCC

CTCGAACATCCAGAGTTGTGGGGGGGAATTATTGATGTCGATGACAGCCTGCCAATTTTGCCCAGATTTG

CCAACAAGACAGGTGCAGCAGTTGGCCGTGCGGCACCAACTCTACGGGGCACAGCTCAAGCAACCGTCAC

TGCCCCAGAATCTCCAGATTCAACCCCAACAGACCTATCTAGTGACAGGGGGACTGGGGCCATTGGCCG

TAATTGCCCAATGGCTAGCCGCAGCAGGAGCAGAAGTAATTCTCGTCAGCCGGCGCGCTCCGGCAGCGGA
```

-continued

```
TCAGCAGACGTTACCGACCAATGCGGTGGTTTATCCTTGCGATTTAGCCGACGCAGCCCAGGTGGCAAGC
TGTTTCAACCTATCCCCACATCAAGGAATTTTCCATGCGGCGGGTACCTTAGCTGATGGTTTGCTGCAAC
AACAACTTGGCAAGTTCCAGACCGTCGCCGCCGCCAATGAAGGGACATGGCATCTGCACCGCCATAGTCA
AGCTCGATCTGGATTTTTTTGTGTTGTTTTCCTCTGTGGCAGGGGTGCTCGGTTCACCGGGACAGGGGAA
TTATGCCGCCGCAACCGGGGCATGGCGGCGATCGCCCAATATCGACAAGCCCAAGGTTTACCCGCCCTGG
CGATCCATTGGGGGCCTTGGGCCGAAGGGGGAATGGCCAACTCCCTCAGCAACCAATTTAGCGTGGCTGC
CGCCCCCCCAGGGACTAACAATCCTCGAAGTCTTGGGCGCCCAGGGGGAATGGGGGTCTTTAACCGGACT
GGCAACCTGGCCAACAGTTCCCCGAATTTGCCAACCCATTACTTTGCAGCCGTTATTCCCTCTGCTGAGG
CTGTGCCCCAACGGCTTCAATTTTTGACAATTAATCAACCTAGAAGCTTCTCAGCGGGCTGACTATCTA
CTGGATTATCTGCGGCGGTCTGTGGCGCAATCCTCAAGTTAGAATTGAGCAATTCAAGCCACGATAGCCT
GTTGGATCTGGGCATGGATTCGTTGATGATCATGGAGGCGATCGCCAGCCTCAAGCAGGATTTACAACTG
ATGTTGTACCCCAGGGAATCTACGAACGGCCCAGACTTGATGTGTTGACGGCCTATCTAGCGGCGGAATT
CACCAAGGCCCATGATTCTGAAGCAGCAACGGCGGCAGCAGCGATTCCCTCCCAAGCCTTTCGGTCAACA
ACAGTGGCAACCTGACCACAACCCGAATCCCATTGCCTTTATCCTCTCTAGCCCCCGGTCGGTTCGACG
TTGCTGCGGGTGATGTTAGCCGGACATCCGGGGTTATATTCGCCGCCAGAGCTGCATTTGCTCCCCTTTG
AGACTATGGGCGATCGCCACCAGGAATTGGGTCTATCCCACCTCGGCGAAGGGTTACAACGGGCCTTAAT
GGATCTAGAACCTCACCCCAGAGGCAAGCCAGGCGAAGGTCAACCAATGGGTCAAGCGAATACACCCATT
GCAGACATCTATGCCTATCTCCAACGGCAGGCGGAACAACGTTTACTCATCGACAATCTCCCAGCTACGG
CAGCGATCGCCATATTCTAGACCACAGCGAATCCTCTTTGACCAGGCCAATATATCCATCTGGTACGCCA
TCCCTACGCGGTGATTGAATCCTTTACCCGACTGCGGATGGATAACTGCTGGGGGCCGAGCAGCAGAACC
CCTACGCCCTCGCGGAGTCCATTTGGCGCACCAGCAACCGCAATATTTTAGACCTGGGTCGCACGGTTGG
TGCGGATCGATATCTCCAGGTGATTTACGAAGATCTCGTCCGTGACCCCCGCAAGTTTTGACAATATTTG
TGATTTCCTGGGGGTGGACTTTGACGAAGCGCTCCTCAATCCCTACAGCGGCGATCGCCTTACCGATGGC
CTCCACCAACAGTCCATGGGCGTCGGGGATCCCAATTTCCTCCAGCACAAACCATTGATCCGGCCCTCGC
CGACAATGGCGCTCAATTACCCTGCCCGCTGCTCTCCAGCTGGATACGATCCAGTTGGCCGAACGTTTGC
TTACGATCTCCCCCAGGAACCCCAGCTAACACCCCAGACCCAATCCTTGCCCTCGATGGTGGAGCGGTTC
GTGACAGTGCGCGGTTTAGAACCTGTCTCTGTGAGTGGGGCGATCGCCACCAACCATTGGTGCTACTTCT
CCACGGCATCCTCGAACAGGGGGCCTCCTGGCAACTCATCGCGCCCCAGTTGGCGGCCCAGGGCTATTGG
GTTGTGGCCCCAGACCTGCGTGGTCACGGCAAATCCGCCCATGCCCAGTCCTACAGCATGCTTGATTTTT
TGGCTGACGTAGATGCCCTTGCCAAACAATTAGGCGATCGCCCCTTTACCTTGGTGGGCCACTCCATGGG
TTCCATCATCGGTGCCATGTATGCAGGAATTCGCCAAACCCAGGTAGAAAAGTTGATCCTCGTTGAAACC
ATTGTCCCCAACGACATCGACGACGCTGAAACCGGTAATCACCTGACGACCCATCTCGATTACCTCGCCG
CGCCCCCCCAACACCCGATCTTCCCCAGCCTAGAAGTGGCCGCCCGTCGCCTCCGCCAAGCCACGCCCCA
ACTACCCAAAGACCTCTCGGCGTTCCTCACCCAGCGCAGCACCAAATCCGTCGAAAAGGGGTGCAGTGG
CGTTGGGATGCTTTCCTCCGTACCCGGGCGGGCATTGAATTCAATGGCATTAGCAGACGACGTTACCTGG
CCCTGCTCAAAGATATCCAAGCGCCGATCACCCTCATCTATGGCGATCAGAGTGAATTTAACCGCCCTGC
TGATCTCCAGGCGATCCAAGCGGCTCTCCCCCAGGCCCAACGTTTAACGGTTGCTGGCGGCCATAACCTC
CATTTTGAGAATCCCCAGGCGATCGCCCAAATTGTTTATCAACAACTCCAGACCCCTGTACCCAAAACAC
AATAA
```

-continued

>gi|70077790|ref|YP_001734428.1|1-alkene synthase[*Synechococcus* sp. PCC 7002]

SEQ ID NO. 2

MVGQFANFVDLLQYRAKLQARKTVFSFLADGEAESAALTYGELDQKAQAIAAFLQANQAQGQRALLLYPP
GLEFIGAFLGCLYAGVVAVPAYPPRPNKSFDRLHSIIQDAQAKFALTTTELKDKIADRLEALEGTDFHCL
ATDQVELISGKNWQKPNISGTDLAFLQYTSGSTGDPKGVMVSHHNLIHNSGLINQGFQDTEASMGVSWLP
PYHDMGLIGGILQPIYVGATQILMPPVAFLQRPFRWLKAINDYRVSTSGAPNFAYDLCASQITPEQIREL
DLSCWRLAFSGAEPIRAVTLENFAKTFATAGFQKSAFYPCYGMAETTLIVSGGNGRAQLPQEIIVSKQGI
EANQVRPAQGTETTVTLVGSGEVIGDQIVKIVDPQALTECTVGEIGEVWVKGESVAQGYWQKPDLTQQQF
QGNVGAETGFLRTGDLGFLQGGELYITGRLKDLLIIRGRNHYPQDIELTVEVAHPALRQGAGAAVSVDVN
GEEQLVIVQEVERKYARKLNVAAVAQAIRGAIAAEHQLQPQAICFIKPGSIPKTSSGKIRRHACKAGFLD
GSLAVVGEWQPSHQKEGKGIGTQAVTPSTTTSTNFPLPDQHQQQIEAWLKDNIAHRLGITPQQLDETEPF
ASYGLDSVQAVQVTADLEDWLGRKLDPTLAYDYPTIRTLAQFLVQGNQALEKIPQVPKIQGKEIAVVGLS
CRFPQADNPEAFWELLRNGKDGVRPLKTRWATGEWGGFLEDIDQFEPQFFGISPREAEQMDPQQRLLLEV
TWEALERANIPAESLRHSQTGVFVGISNSDYAQLQVRENNPINPYMGTGNAHSIAANRLSYFLDLRGVSL
SIDTACSSSLVAVHLACQSLINGESELAIAAGVNLILTPDVTQTFTQAGMMSKTGRCQTFDAEADGYVRG
EGCGVVLLKPLAQAERDGDNILAVIHGSAVNQDGRSNGLTAPNGRSQQAVIRQALAQAGITAADLAYLEA
HGTGTPLGDPIEINSLKAVLQTAQREQPCVVGSVKTNIGHLEAAAGIAGLIKVILSLEHGMIPQHLHFKQ
LNPRIDLDGLVTIASKDQPWSGGSQKRFAGVSSFGFGGTNAHVIVGDYAQQKSPLAPPATQDRPWHLLTL
SAKNAQALNALQKSYGDYLAQHPSVDPRDLCLSANTGRSPLKERRFFVFKQVADLQQTLNQDFLAQPRLS
SPAKIAFLFTGQGSQYYGMGQQLYQTSPVFRQVLDECDRLWQTYSPEAPALTDLLYGNHNPDLVHETVYT
QPLLFAVEYAIAQLWLSWGVTPDFCMGHSVGEYVAACLAGVFSLADGMKLITARGKLMHALPSNGSMAAV
FADKTVIKPYLSEHLTVGAENGSHLVLSGKTPCLEASIHKLQSQGIKTKPLKVSHAFHSPLMAPMLAEFR
EIAEQITFHPPRIPLISNVTGGQIEAEIAQADYWVKHVSQPVKFVQSIQTLAQAGVNVYLEIGVKPVLLS
MGRHCLAEQEAVWLPSLRPHSEPWPEILTSLGKLYEQGLNIDWQTVEAGDRRRKLILPTYPFQRQRYWFN
QGSWQTVETESVNPGPDDLNDWLYQVAWTPLDTLPPAPEPSAKLWLILGDRHDHQPIEAQFKNAQRVYLG
QSNHFPTNAPWEVSADALDNLFTHVGSQNLAGILYLCPPGEDPEDLDEIQKQTSGFALQLIQTLYQQKIA
VPCWFVTHQSQRVLETDAVTGFAQGGLWGLAQAIALEHPELWGGIIDVDDSLPNFAQICQQRQVQQLAVR
HQKLYGAQLKKQPSLPQKNLQIQPQQTYLVTGGLGAIGRKIAQWLAAAGAEKVILVSRRAPAADQQTLPT
NAVVYPCDLADAAQVAKLFQTYPHIKGIFHAAGTLADGLLQQQTWQKFQTVAAAKMKGTWHLHRHSQKLD
LDFFVLFSSVAGVLGSPGQGNYAAANRGMAAIAQYRQAQGLPALAIHWGPWAEGGMANSLSNQNLAWLPP
PQGLTILEKVLGAQGEMGVFKPDWQNLAKQFPEFAKTHYFAAVIPSAEAVPPTASIFDKLINLEASQRAD
YLLDYLRRSVAQILKLEIEQIQSHDSLLDLGMDSLMIMEAIASLKQDLQLMLYPREIYERPRLDVLTAYL
AAEFTKAHDSEAATAAAAIPSQSLSVKTKKQWQKPDHKNPNPIAFILSSPRSGSTLLRVMLAGHPGLYSP
PELHLLPFETMGDRHQELGLSHLGEGLQRALMDLENLTPEASQAKVNQWVKANTPIADIYAYLQRQAEQR
LLIDKSPSYGSDRHILDHSEILFDQAKYIHLVRHPYAVIESFTRLRMDKLLGAEQQNPYALAESIWRTSN
RNILDLGRTVGADRYLQVIYEDLVRDPRKVLTNICDFLGVDFDEALLNPYSGDRLTDGLHQQSMGVGDPN
FLQHKTIDPALADKWRSITLPAALQLDTIQLAETFAYDLPQEPQLTPQTQSLPSMVERFVTVRGLETCLC
EWGDRHQPLVLLLHGILEQGASWQLIAPQLAAQGYWVVAPDLRGHGKSAHAQSYSMLDFLADVDALAKQL
GDRPFTLVGHSMGSIIGAMYAGIRQTQVEKLILVETIVPNDIDDAETGNHLTTHLDYLAAPPQHPIFPSL
EVAARRLRQATPQLPKDLSAFLTQRSTKSVEKGVQWRWDAFLRTRAGIEFNGISRRRYLALLKDIQAPIT
LIYGDQSEFNRPADLQAIQAALPQAQRLTVAGGHNLHFENPQAIAQIVYQQLQTPVPKTQ

SYNPCC7002_A1174 hydrolase alpha/beta fold domain-containing protein
>gi|170076636:c1215155-1214256 Synechococcus sp. PCC 7002
SEQ ID NO. 3
ATGACCATTACTTCCCCCGCTCATCCCCATACCGATTACAGCTGGCAATGGCACGGCTTCAATATTAACT

ATCGTCAGTGGGGCACCCAGGGGCTGCCCGTTCTTTTCGTCCATGGCTTTGGGGCCTCGGCCGGTCATTG

GCGCAAAAATCTTCCGGTTTTAGGGGAACATTACCGCTGCTATGCCATCGACTTACTGGGCTTTGGGAAA

TCGGCAAAACCCCAACCGGAGGTTGAAGCGGACTACACTTTTGAAACTTGGGCCACCCAGATTAAGGCGT

TCTGTGCTGAAATCATTGGTGAACCGGCTTTTCTAGTTGGTAATTCCATTGGTTGTGTCGTTGTCATGCA

GGCGGCTGTGTCCTATCCCCACTGGGTGCGGGGGGTTGTGGCACTCAATTTTTCCCTGCGGCTGTTCCAT

GAGCGCAATCTTTTAAAAGCACCTTTTTATCAACGCTGGGGCGTTCCCCTCTTCCAAAAACTCTTGACCC

AAACCCCCCTCGGTTCCTTGTTCTTTAAGCAATTGGCCCAGCCGAAAACAATCCGCAAAATTTTAGCCCA

GGCCTACCGAGACAAAACAGCGATTACCGATGAGTTGGTGGAGCTGATCCTGACCCCCGCCCAGGACCCA

GGGGCGGCAGCGGTTTTCCTGGCCTTTACGAGTTATTCCCAGGGGCCACTCCCGGACGACCTGCTGCCCC

AGTTGCATTGCCCCACGGCAGTTTTGTGGGGAACAGCGGATCCGTGGGAACCAGTTGATCTGGGCCGTGC

CCTTGTCGCCCAATATCCTCAGATTGAGTTTATTCCCCTCGATAATGTCGGCCATTGTCCCCAGGATGAA

GCTCCGGCATTAGTCAACGGCTATTTACTCGATTGGTTAGGGCGACAACAGTCAGCGTAG

>gi|170077791| ref| YP_001734429.1| hydrolase alpha/beta fold
domain-containing protein [Synechococcus sp. PCC 7002]
SEQ ID NO. 4
MTITSPAHPHTDYSWQWHGFNINYRQWGTQGLPVLFVHGFGASAGHWRKNLPVLGEHYRCYAIDLLGFGK

SAKPQPEVEADYTFETWATQIKAFCAEIIGEPAFLVGNSIGCVVVMQAAVSYPHWVRGVVALNFSLRLFH

ERNLLKAPFYQRWGVPLFQKLLTQTPLGSLFFKQLAQPKTIRKILAQAYRDKTAITDELVELILTPAQDP

GAAAVFLAFTSYSQGPLPDDLLPQLHCPTAVLWGTADPWEPVDLGRALVAQYPQIEFIPLDNVGHCPQDE

APALVNGYLLDWLGRQQSA

The sequence of pJB844, a knockout vector for SYNPCC7002_A1173
(UHR and DHR in italics; aacC1 gentamycin marker is underlined)
SEQ ID NO 5
TTAGAAAAACTCATCGAGCATCAAATGAAACTGCAATTTATTCATATCAGGATTATCAATACCA

TATTTTTGAAAAAGCCGTTTCTGTAATGAAGGAGAAAACTCACCGAGGCAGTTCCATAGGATGG

CAAGATCCTGGTATCGGTCTGCGATTCCGACTCGTCCAACATCAATACAACCTATTAATTTCCC

CTCGTCAAAAATAAGGTTATCAAGTGAGAAATCACCATGAGTGACGACTGAATCCGGTGAGAAT

GGCAAAAGTTTATGCATTTCTTTCCAGACTTGTTCAACAGGCCAGCCATTACGCTCGTCATCAA

AATCACTCGCATCAACCAAACCGTTATTCATTCGTGATTGCGCCTGAGCGAGGCGAAATACGCG

ATCGCTGTTAAAAGGACAATTACAAACAGGAATCGAGTGCAACCGGCGCAGGAACACTGCCAGC

GCATCAACAATATTTTCACCTGAATCAGGATATTCTTCTAATACCTGGAACGCTGTTTTTCCGG

GGATCGCAGTGGTGAGTAACCATGCATCATCAGGAGTACGGATAAAATGCTTGATGGTCGGAAG

TGGCATAAATTCCGTCAGCCAGTTTAGTCTGACCATCTCATCTGTAACATCATTGGCAACGCTA

CCTTTGCCATGTTTCAGAAACAACTCTGGCGCATCGGGCTTCCCATACAAGCGATAGATTGTCG

CACCTGATTGCCCGACATTATCGCGAGCCCATTTATACCCATATAAATCAGCATCCATGTTGGA

ATTTAATCGCGGCCTCGACGTTTCCCGTTGAATATGGCTCATATTCTTCCTTTTTCAATATTAT

TGAAGCATTTATCAGGGTTATTGTCTCATGAGCGGATACATATTTGAATGTATTTAGAAAAATA

AACAAATAGGGGTCAGTGTTACAACCAATTAACCAATTCTGAACATTATCGCGAGCCCATTTAT

ACCTGAATATGGCTCATAACACCCCTTGTTTGCCTGGCGGCAGTAGCGCGGTGGTCCCACCTGA

CCCCATGCCGAACTCAGAAGTGAAACGCCGTAGCGCCGATGGTAGTGTGGGGACTCCCCATGCG

AGAGTAGGGAACTGCCAGGCATCAAATAAAACGAAAGGCTCAGTCGAAAGACTGGGCCTTTCGC

CCGGGCTAATTAGGGGGTGTCGCCCTTCTGAAGTGGGGCCTGCAGG*ttattgaggtatcgcgag*
*atggctcccacattcggggaaatagacatttcattgtcattgagaaccaccattaaattcgtat*
*cgggtaaatgacccgcatggttgatggcttcgagggccatgccgccggtcaaggcaccatcacc*
*aatgactgccacacatttaaactcttctcccttggcatcccgtgccaatgccatccctagcgct*
*gcggaaatactggtcgaggcatggccagcaccaaaatgatcaaacacattttcactgcgcttaa*
*ggtagccagctaccccatccttttgccggagggtgtggaattcgttgtagcgtccggtaatcaa*
*tttatggggataagcctgatgaccgacatcccacaccaccttgtcgcgatcgagatcaagggtt*
*tggtagagggcgagggttagttcaaccaccctaaaccagggccgaggtggccaccacttgcgg*
*caatcgtctggaggtgttttcgcgaatttgccgggcaatctcttccaactgacggacggtcaa*
*gccgtggagttggttcggatgggtaatttcactcaggtgcatgggtgtttctagagagcgatct*
*tataaaggggtctagttctcaggatatcaggtctaacaatttaatcagaagatcccggttagt*
*ccggatgatcccatgggttgtgtgggaatcttggtcaaggttccacagatgtttaggatctaa*
*tatttacgggttttcggactgcactttgcaatattttt*GCGGCCGCTCATATGTAACAGGAATTC
GGTTACTAGTTTTTAATTAAcgaatccatgtgggagtttattcttgacacagatatttatgata
taataactgagtaagcttaacataaggaggaaaaactaatgttacgcagcagcaacgatgttac
gcagcagggcagtcgccctaaaacaaagttaggtggctcaagtatgggcatcattcgcacatgt
aggctcggccctgaccaagtcaaatccatgcgggctgctcttgatcttttcggtcgtgagttcg
gagacgtagccacctactcccaacatcagccggactccgattacctcgggaacttgctccgtag
taagacattcatcgcgcttgctgccttcgaccaagaagcggttgttggcgctctcgcggcttac
gttctgcccaagtttgagcagccgcgtagtgagatctatatctatgatctcgcagtctccggcg
agcaccggaggcagggcattgccaccgcgctcatcaatctcctcaagcatgaggccaacgcgct
tggtgcttatgtgatctacgtgcaagcagattacggtgacgatcccgcagtggctctctataca
aagttgggcatacgggaagaagtgatgcactttgatatcgacccaagtaccgccaccta GGcgc
gccgtatgccttagcaactcctgtgaatggaaattctggactccgtatcctagcaattttacg
aatacccacgggctatagcctagttaaccatataaaccgtgagttccctccccacggtaaatc
ctcccaaaatccgccgttccttcgattatggagggcctggttcaactgatttgagtgtaaaag
ccctaggctacgctgactgttgtcgccctaacaatcgagtaaatagccgttgactaatgccgg
agcttcatcctggggacaatggccgacattatcgaggggaataaactcaatctgaggatattgg
gcgacaagggcacggcccagatcaactggttccacggatccgctgttccccacaaaactgccg
tggggcaatgcaactggggcagcaggtcgtccggagtggcccctgggaataactcgtaaaggc
caggaaaaccgctgccgcccctgggtcctgggcgggggtcaggatcagctccaccaactcatcg
gtaatcgctgttttgtctcggtaggcctgggctaaaattttgcggattgttttcggctgggcca
attgcttaaagaacaaggaaccgagggggttggtcaagagttttggaagagggaacgcc
ccagcgttgataaaaaggtgctttaaaagattgcgctcatggaacagccgcagggaaaaattg
agtgccacaacccccgcacccagtgggataggacacagccgcctgcatgacaacgacacaac
caatggaattaccaactagaaaagccggttcggccggCCAACGTCAAAAGGGCGACACAAAATT
TATTCTAAATGCATAATAAATACTGATAACATCTTATAGTTTGTATTATATTTTGTATTATCGT
TGACATGTATAATTTTGATATCAAAAACTGATTTTCCCTTTATTATTTTCGAGATTTATTTTCT
TAATTCTCTTTAACAAACTAGAAATATTGTATATACAAAAAATCATAAATAATAGATGAATAGT
TTAATTATAGGTGTTCATCAATCGAAAAAGCAACGTATCTTATTTAAAGTGCGTTGCTTTTTC -continued

TCATTTATAAGGTTAAATAATTCTCATATATCAAGCAAAGTGACAGGCGCCCTTAAATATTCTG

ACAAATGCTCTTTCCCTAAACTCCCCCCATAAAAAAACCCGCCGAAGCGGGTTTTTACGTTATT

TGCGGATTAACGATTACTCGTTATCAGAACCGCCCAGGGGGCCCGAGCTTAAGACTGGCCGTCG

TTTTACAACACAGAAAGAGTTTGTAGAAACGCAAAAAGGCCATCCGTCAGGGGCCTTCTGCTTA

GTTTGATGCCTGGCAGTTCCCTACTCTCGCCTTCCGCTTCCTCGCTCACTGACTCGCTGCGCTC

GGTCGTTCGGCTGCGGCGAGCGGTATCAGCTCACTCAAAGGCGGTAATACGGTTATCCACAGAA

TCAGGGGATAACGCAGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCATCACAAAAATCGACG

CTCAAGTCAGAGGTGGCGAAACCCGACAGGACTATAAAGATACCAGGCGTTTCCCCCTGGAAGC

TCCCTCGTGCGCTCTCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCGGTGTAGGTCGTTCG

CTCCAAGCTGGGCTGTGTGCACGAACCCCCCGTTCAGCCCGACCGCTGCGCCTTATCCGGTAAC

TATCGTCTTGAGTCCAACCCGGTAAGACACGACTTATCGCCACTGGCAGCAGCCACTGGTAACA

GGATTAGCAGAGCGAGGTATGTAGGCGGTGCTACAGAGTTCTTGAAGTGGTGGGCTAACTACGG

CTACACTAGAAGAACAGTATTTGGTATCTGCGCTCTGCTGAAGCCAGTTACCTTCGGAAAAAGA

GTTGGTAGCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGGGGTCTGA

CGCTCAGTGGAACGACGCGCGCGTAACTCACGTTAAGGGATTTTGGTCATGAGCTTGCGCCGTC

CCGTCAAGTCAGCGTAATGCTCTGCTT

The sequence of pJB845, a knockout vector for SYNPCC7002_A1174
(UHR and DHR in italics; aacC1 gentamycin marker is underlined)
SEQ ID NO 6

TTAGAAAAACTCATCGAGCATCAAATGAAACTGCAATTTATTCATATCAGGATTATCAATACCA

TATTTTTGAAAAAGCCGTTTCTGTAATGAAGGAGAAAACTCACCGAGGCAGTTCCATAGGATGG

CAAGATCCTGGTATCGGTCTGCGATTCCGACTCGTCCAACATCAATACAACCTATTAATTTCCC

CTCGTCAAAAATAAGGTTATCAAGTGAGAAATCACCATGAGTGACGACTGAATCCGGTGAGAAT

GGCAAAAGTTTATGCATTTCTTTCCAGACTTGTTCAACAGGCCAGCCATTACGCTCGTCATCAA

AATCACTCGCATCAACCAAACCGTTATTCATTCGTGATTGCGCCTGAGCGAGGCGAAATACGCG

ATCGCTGTTAAAAGGACAATTACAAACAGGAATCGAGTGCAACCGGCGCAGGAACACTGCCAGC

GCATCAACAATATTTTCACCTGAATCAGGATATTCTTCTAATACCTGGAACGCTGTTTTTCCGG

GGATCGCAGTGGTGAGTAACCATGCATCATCAGGAGTACGGATAAAATGCTTGATGGTCGGAAG

TGGCATAAATTCCGTCAGCCAGTTTAGTCTGACCATCTCATCTGTAACATCATTGGCAACGCTA

CCTTTGCCATGTTTCAGAAACAACTCTGGCGCATCGGGCTTCCCATACAAGCGATAGATTGTCG

CACCTGATTGCCCGACATTATCGCGAGCCCATTTATACCCATATAAATCAGCATCCATGTTGGA

ATTTAATCGCGGCCTCGACGTTTCCCGTTGAATATGGCTCATATTCTTCCTTTTTCAATATTAT

TGAAGCATTTATCAGGGTTATTGTCTCATGAGCGGATACATATTTGAATGTATTTAGAAAAATA

AACAAATAGGGGTCAGTGTTACAACCAATTAACCAATTCTGAACATTATCGCGAGCCCATTTAT

ACCTGAATATGGCTCATAACACCCCTTGTTTGCCTGGCGGCAGTAGCGCGGTGGTCCCACCTGA

CCCCATGCCGAACTCAGAAGTGAAACGCCGTAGCGCCGATGGTAGTGTGGGGACTCCCCATGCG

AGAGTAGGGAACTGCCAGGCATCAAATAAAACGAAAGGCTCAGTCGAAAGACTGGGCCTTTCGC

CCGGGCTAATTAGGGGGTGTCGCCCTTCTGAAGTGGGGCCTGC*Aggattgtggtgggaaaccat*

*cactcctttaggatcgcccgtggagccactggtgtattgcaaaaaagcgagatctgtgccggaa* atgttcggttttttgccaattttttcctgaaattaattcaacttgatctgtagccaaacaatgaa
aatccgtaccttctaaagcttcgaggcgatcggcaattttatctttaagttctgttgtggtgag
ggcaaattttgcctgggcatcttggataatgctatggaggcggtcaaaggatttattcggccgt
ggtgggtaagctggcaccgcaacaacaccagcatacaaacatcccaaaaaggcaccgataaact
ctaaacccggtggataaagtaataatgcccgttgcccttgagcctggttagcttgcaaaaaagc
ggcgatcgcctgggcttttggtctaattctcgtaggtcagggccgcagattccgcttcgcca
tcagccagaaaactaaacacggttttccgcgcctgaagtttagctctgtactggagcagatcga
cgaaatttgcaaattgaccaaccatgtatgccttagcaactcctgtgaatggaaattctggact
ccgtatcctagcaattttacgaatacccacgggctatagcctagttaaccatattaaaccgtg
agttccctccccacggtaaatcctcccaaaatccgccgttccttcgattatggagggcctggtt
tcaactgatttgagtgtaaaagccctaggGCGGCCGCTCATATGTAACAGGAATTCGGTTACTA
GTTTTTAATTAAcgaatccatgtgggagtttattcttgacacagatatttatgatataataact
gagtaagcttaacataaggaggaaaaactaatgttacgcagcagcaacgatgttacgcagcagg
gcagtcgccctaaaacaaagttaggtggctcaagtatgggcatcattcgcacatgtaggctcgg
ccctgaccaagtcaaatccatgcgggctgctcttgatcttttcggtcgtgagttcggagacgta
gccacctactcccaacatcagccggactccgattacctcgggaacttgctccgtagtaagacat
tcatcgcgcttgctgccttcgaccaagaagcggttgttggcgctctcgcggcttacgttctgcc
caagtttgagcagccgcgtagtgagatctatatctatgatctcgcagtctccggcgagcaccgg
aggcagggcattgccaccgcgctcatcaatctcctcaagcatgaggccaacgcgcttggtgctt
atgtgatctacgtgcaagcagattacggtgacgatcccgcagtggctctctatacaaagttggg
catacgggaagaagtgatgcactttgatatcgacccaagtaccgccaccta GGcgcgcgggtga
gcgatggataaaaccgaaataaggaacaaatgtcctagggcgtgttgtctaaatcgtgatggca
aagatggggcaccggatcataaccccagggtgaaacgggtgacagcggccaaggcgctttagg
gcgagccaactgccccggagtacaccaaagcgttccacggcttcgagggcatatttgggaacagg
tgggctgaaagcgacaactgggggggaataggggggaaatccagcgacggtagccttgatgct
ccagaggattaagcttttcatggtatttaggcaacggaagcagtcttttggaggtcgatggttt
gaccaagggcttcgttgacgagacgactaaagtcttcgccttcgatggtttcttcttcgatgag
acgatccaccagacgatctacaagttgacgattgtcccgaataatttgcttggcagtttcgtag
cactcgttgataatttcgcgcaccttgaggtcaatgcgctgggcgatcgcctcggaatattcag
gccgctccccaaaccaatcatttctgaggaaaacttcaccccgattggtttctagggcaaagtg
acccagttctgacatcccaaattttgtcaccatttgacgggcaatgttcgtgagcatttggata
tcctgggaggccccagaagtgatttcatcgtagccaaagacaatatcctcggcggcgcgtcccc
ccagggccacggcgatttgggcgcggaattgggctttggttggccggCCAACGTCAAAAGGCGA
CACAAAATTTATTCTAAATGCATAATAAATACTGATAACATCTTATAGTTTGTATTATATTTTG
TATTATCGTTGACATGTATAATTTTGATATCAAAAACTGATTTTCCCTTTATTATTTTCGAGAT
TTATTTTCTTAATTCTCTTTAACAAACTAGAAATATTGTATATACAAAAAATCATAAATAATAG
ATGAATAGTTTAATTATAGGTGTTCATCAATCGAAAAAGCAACGTATCTTATTTAAAGTGCGTT
GCTTTTTTCTCATTTATAAGGTTAAATAATTCTCATATATCAAGCAAAGTGACAGGCGCCCTTA
AATATTCTGACAAATGCTCTTTCCCTAAACTCCCCCCATAAAAAAACCCGCCGAAGCGGGTTTT
TACGTTATTTGCGGATTAACGATTACTCGTTATCAGAACCGCCCAGGGGGCCCGAGCTTAAGAC
TGGCCGTCGTTTTACAACACAGAAAGAGTTTGTAGAAACGCAAAAAGGCCATCCGTCAGGGGCC

```
TTCTGCTTAGTTTGATGCCTGGCAGTTCCCTACTCTCGCCTTCCGCTTCCTCGCTCACTGACTC
GCTGCGCTCGGTCGTTCGGCTGCGGCGAGCGGTATCAGCTCACTCAAAGGCGGTAATACGGTTA
TCCACAGAATCAGGGGATAACGCAGGAAAGAACATGTGAGCAAAAGGCCAGCAAAAGGCCAGGA
ACCGTAAAAAGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAGTGGTGGGC
TAACTACGGCTACACTAGAAGAACAGTATTTGGTATCTGCGCTCTGCTGAAGCCAGTTACCTTC
GGAAAAAGAGTTGGTAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCTTTGATCTTTTCTAC
GGGGTCTGACGCTCAGTGGAACGACGCGCGCGTAACTCACGTTAAGGGATTTTGGTCATGAGCT
TGCGCCGTCCCGTCAAGTCAGCGTAATGCTCTGCTT
```

The sequence of pJB808, a knockout vector for SYNPCC7002_A1189
(UHR and DHR in italics; aacC1 gentamycin marker is underlined)

SEQ ID NO: 7

```
TAGAAAAACTCATCGAGCATCAAATGAAACTGCAATTTATTCATATCAGGATTATCAATACCAT
ATTTTTGAAAAAGCCGTTTCTGTAATGAAGGAGAAAACTCACCGAGGCAGTTCCATAGGATGGC
AAGATCCTGGTATCGGTCTGCGATTCCGACTCGTCCAACATCAATACAACCTATTAATTTCCCC
TCGTCAAAAATAAGGTTATCAAGTGAGAAATCACCATGAGTGACGACTGAATCCGGTGAGAATG
GCAAAAGTTTATGCATTTCTTTCCAGACTTGTTCAACAGGCCAGCCATTACGCTCGTCATCAAA
ATCACTCGCATCAACCAAACCGTTATTCATTCGTGATTGCGCCTGAGCGAGGCGAAATACGCGA
TCGCTGTTAAAAGGACAATTACAAACAGGAATCGAGTGCAACCGGCGCAGGAACACTGCCAGCG
CATCAACAATATTTTCACCTGAATCAGGATATTCTTCTAATACCTGGAACGCTGTTTTTCCGGG
GATCGCAGTGGTGAGTAACCATGCATCATCAGGAGTACGGATAAAATGCTTGATGGTCGGAAGT
GGCATAAATTCCGTCAGCCAGTTTAGTCTGACCATCTCATCTGTAACATCATTGGCAACGCTAC
CTTTGCCATGTTTCAGAAACAACTCTGGCGCATCGGGCTTCCCATACAAGCGATAGATTGTCGC
ACCTGATTGCCCGACATTATCGCGAGCCCATTTATACCCATATAAATCAGCATCCATGTTGGAA
TTTAATCGCGGCCTCGACGTTTCCCGTTGAATATGGCTCATATTCTTCCTTTTTCAATATTATT
GAAGCATTTATCAGGGTTATTGTCTCATGAGCGGATACATATTTGAATGTATTTAGAAAAATAA
ACAAATAGGGGTCAGTGTTACAACCAATTAACCAATTCTGAACATTATCGCGAGCCCATTTATA
CCTGAATATGGCTCATAACACCCCTTGTTTGCCTGGCGGCAGTAGCGCGGTGGTCCCACCTGAC
CCCATGCCGAACTCAGAAGTGAAACGCCGTAGCGCCGATGGTAGTGTGGGGACTCCCCATGCGA
GAGTAGGGAACTGCCAGGCATCAAATAAAACGAAAGGCTCAGTCGAAAGACTGGGCCTTTCGCC
CGGGCTAATTAGGGGGTGTCGCCCTTATTCGACTCTATAGTGAAGTTCCTATTCTCTAGAAAGT
ATAGGAACTTCTGAAGTGGGGAAGCTTAAGTATAGGAACTTCTGAAGTGGGGCCTGCA
```
*GGGAAA
GGCTCTTGAGGCTATCATGACAGAAGCATCGCAGCCTATAAAATACGCTGGAAAAGAATATAAA
TATGCTGTTTCGTATCATGTCCTAAATGCTGCTGATTTTGGTGTTCCGCAATTTAGAGAAAGAG
TATTCATCGTAGGTAATCGTTTGGGCAAAACATTCCAATTTCCTGAACCAACTCATGGGCCTAG
CAACCAAGCGAGACAGATAGATCTTTTTGGCAAGCAGCTAAAACCTTACAAAACTGTTCAAGAT*

```
GCAATTAGCACTCTCCCCCCTGCAACCCCTCCTTCAGCGATGGCACTAAGAGTTTCGCAGACCA
TAAAAGATAGGATAAAGAATCATGGATATTAAAAACGTTCATATCAAAAATCACGAACAAACAG
CTCATGCACCTTCCACTCTAGAAAAAATTCGTAAAGTCAAACAAGGGGGTAAACTCTCAGAACA
GACAAAGACATTTGGTTCAACCTACCGCAGGTTAGATCCGAACCAGCCATCTCCTACAGTGACC
CGTAGTGGTTATCGAGATTTTATTCATCCTTTTGAAGATCGAATGCTCACAGTTCGTGAACTGG
CTTGTTTGCAAACCTTTCCCCTTGATTGGGAGTTTACCGGAACTCGACTTGATTCTTATAGTAG
TAAACGTAAAGTGACGATGACTCAGTTTGGACAAGTGGGTAATGCAGTACCGCCGTTACTTGCT
GAAGCTGTTGCTAAAGCGGTTAGCGAACAGCTTCTGGATGTCGCGGCCGCGGTACCCATATGTA
ACAGGAATTCACTAGTTTTTAATTAAcgaatccatgtgggagtttattcttgacacagatattt
atgatataataactgagtaagcttaacataaggaggaaaaactaatgttacgcagcagcaacga
tgttacgcagcagggcagtcgccctaaaacaaagttaggtggctcaagtatgggcatcattcgc
acatgtaggctcggccctgaccaagtcaaatccatgcgggctgctcttgatcttttcggtcgtg
agttcggagacgtagccacctactcccaacatcagccggactccgattacctcgggaacttgct
ccgtagtaagacattcatcgcgcttgctgccttcgaccaagaagcggttgttggcgctctcgcg
gcttacgttctgcccaagtttgagcagccgcgtagtgagatctatatctatgatctcgcagtct
ccggcgagcaccggaggcagggcattgccaccgcgctcatcaatctcctcaagcatgaggccaa
cgcgcttggtgcttatgtgatctacgtgcaagcagattacggtgacgatcccgcagtggctctc
tatacaaagttgggcatacgggaagaagtgatgcactttgatatcgacccaagtaccgccacct
aGGCGCGCCCTTTACAAAATCAAACCCGATCGCCTCTCTATTTTGATAAATCTATGTCTACTCC
CTCTGTTACCCCTGTAGAATCTAGCACCCTAATCAAAACCCCTGAACTGCTGGCTCCGGCGGGA
AATTGGGACTGTGCGATCACCGCCGTGGAGAATGGGCTGATGCGATTTATTTTGGGCTGGATA
AATTTAATGCCCGGATGCGATCACAAAACTTTGTCGAGTCAGATTTGCCGGAGTTGATGGCATA
CTTACATCGGCGCGGCGTGAAGGGCTATGTGACGTTAAATACGCTGATTTTCACCTCGGAATTG
GCGGCAGTCGAACAATATTTGCGGTCGATTATTGCGGCGGGAGTCGATGCGGCGATCGTCCAGG
ATGTGGGGCTGTGCCAATTAATTTGGCAATTGTCGCCCGATTTTCCGATCCATGGTTCGACGCA
AATGACCGTCACCAGCGCCGCAGGGGTCGAGTTCGCGCAAAACTTGGGTTGTGATTTGGTGGTA
TTGGCGCGGGAATGTTCGATCAAGGAAATCAATAAAATCCAGCAGGAATTGGGTCAACAAAAGA
TCTCAATGCCGCTAGAAGTGTTTGTCCACGGGCGTTGTGCGTCGCCTATTCTGGGCAATGTTT
AACCAGTGAATCCCTCGGCGGACGGTCGGCCAATCGCGGAGAATGCGCCCAAGCCTGCCGGATG
CCCTACGAAATGATTGTCGATGGTAGGCCATTTGATCTGAGCGACAGACGTTACCGGCCGGCCA
AAATGAAGTGAAGTTCCTATACTTAAGCTTAAAATGAAGTGAAGTTCCTATACTTTCTAGAGAA
TAGGAACTTCTATAGTGAGTCGAATAAGGGCGACACAAAATTTATTCTAAATGCATAATAAATA
CTGATAACATCTTATAGTTTGTATTATATTTTGTATTATCGTTGACATGTATAATTTTGATATC
AAAAACTGATTTTCCCTTTATTATTTTCGAGATTTATTTTCTTAATTCTCTTTAACAAACTAGA
AATATTGTATATACAAAAAATCATAAATAATAGATGAATAGTTTAATTATAGGTGTTCATCAAT
CGAAAAAGCAACGTATCTTATTTAAAGTGCGTTGCTTTTTTCTCATTTATAAGGTTAAATAATT
CTCATATATCAAGCAAAGTGACAGGCGCCCTTAAATATTCTGACAAATGCTCTTTCCCTAAACT
CCCCCCATAAAAAAACCCGCCGAAGCGGGTTTTTACGTTATTTGCGGATTAACGATTACTCGTT
ATCAGAACCGCCCAGGGGGCCCGAGCTTAAGACTGGCCGTCGTTTTACAACACAGAAAGAGTTT
GTAGAAACGCAAAAAGGCCATCCGTCAGGGGCCTTCTGCTTAGTTTGATGCCTGGCAGTTCCCT
```

-continued

```
ACTCTCGCCTTCCGCTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCTGGCGTTTTT

CCATAGGCTCCGCCCCCCTGACGAGCATCACAAAAATCGACGCTCAAGTCAGAGGTGGCGAAAC

CCGACAGGACTATAAAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGTCCAACCCGG

TAAGACACGACTTATCGCCACTGGCAGCAGCCACTGGTAACAGGATTAGCAGAGCGAGGTATGT

AGGCGGTGCTACAGAGTTCTTGAAGTGGTGGGCTAACTACGGCTACACTAGAAGAACAGTATTT

GGTATCTGCGCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCGCAGAAAAAA

AGGATCTCAAGAAGATCCTTTGATCTTTTCTACGGGGTCTGACGCTCAGTGGAACGACGCGCGC

GTAACTCACGTTAAGGGATTTTGGTCATGAGCTTGCGCCGTCCCGTCAAGTCAGCGTAATGCTC

TGCTTT
```

NonA homolog from *Cyanothece* sp. PCC7424 YP_002377174.1

SEQ ID NO: 8

```
MKRNFSNFVDLLNHRAETQSDKILFTFLGDGETESLSLTYQQLDQQARAIAVQLQSLNATGERALLLYQP

GLEFISAFFGCLYGGVIPVPAYPPRANRSIERLQAIVSDAEAKFALTSESLVNSIEGKLTQSLSQEAIQC

VTTDNLELSLSQGWHKPKINPEQLAFLQYTSGSTGNPKGVMVSHSNLMHNAALINHYFQDTPESRGASWL

PPYHDMGLIGGILQPIYVGVYVVLMPPVTFLQRPLRWLEVISRYRITTSGAPNFAYELCATQITPEQREN

LDLSCWELAFSGAEPIRAHTLEQFAKAFAPCGFRPEAFYACYGMAETTLIVTGGKRSEKPFLKEFNSKGI

EKNQVIPASSCDQDRVSLVSCGQVAEAQKVIIVNPETLNQCADDEIGEIWVSSESVAQGYWNRPQLTEAI

FKAYTPDSPERPFLRTGDLGFLQDGELFVTGRLKDLIIIRGRNHYPQDIEMTAEKSHPALRESCGAAFSV

EVGEEERLVITYEVKRSYIRKLNVEEVTSAIRKAVTQTHELQPYAIVLLKTGSIPKTSSGKIQRHACKAE

FLEGSLNSVGQWSVTQLSEASSQQSKPKPRKNLKQHSPSNSQQQLIQDWLVDKIAQRLSISSAEIEITEP

FASYGLDSVQAVRITAELEDWLKVKLSPTLAYDYPSIESLAQYLTALLKGQEIPSTPVLKTVTQQQTKSE

LIAIIGMGCRFPGANNPDQFWQLLQQGKDQITQVKGRWEKETWGGFLDHIDQFDPQFFGISRREAQEIDP

QQRLLLEVSWEALENASIAVDQLAGSQTGVFIGISSSDYSQIRLKSQLDPSAYAGTGNAHSIAANRLSYF

YDFRGPSLTVDTACSSSLVAVHLAISSLQRGECQMAIAGGVNLLLSPELTETFTQAGMMATDGRCKTFDE

GADGYVRGEGCGVVILKSLENAIADGDPILGVIHGSAINQDGRSNGLTAPNGIAQKQVICQALINGNIQA

ADISYIETHGTGTPLGDPIEVNALKSVLMEGRSLDQPLWIGSLKTNIGHLEAAAGIAGLIKVILSLKHQQ

IPPHLHLNSLNPHINLNETPIAIPTQLTPWKIDSKPRLAGVSSFGFGGTNAHVIVGEYNSLSPSPENLSP

YPSPTRREELKPVERPLHILTLSAKREKDLSALIDSYKSYLTSQPTASLEDICFTANVGRSPLKHRVAII

ANSQDQLREKLGKGEVIKAENSAQLTPKIAFLFTGQGSQYVGMGYQLYQTQPTFKTALDTCADLLSPYLK

RPLLEILYPQDSTAISDELDQTAYTQPALFALEYALAQLWLSWGIEPSIVMGHSVGEYVAATLAGVFSLE

DGIKLIAHRGKLMQALPQNGQMVAVLSDEVTVKKAINSHHQKVVIAAINGEKSLVISGEHQAVIEVTEVL

KNQGIKTKPLTVSHAFHSPLMQPMLTEFERVAQEIEYSLPLIPIVSNVTGNIAGEEMATPHYWVNHVVDT

VQFASSMKCLEKQGYKVFLEIGAKPTLLGMGRSTLESDPLNSNSSPYLWLPSLRPEQEDWQQILSSLAQL

YVNGIWVDWAGFDQDYPRQRVIGLPTYPFDRQSYWLTQTPQLNSHGLYQVEWEVKQPINDNFSLINPSTW

LILADEQGLGELLGQELEKLGQTCLLIYPENGKGQKETFESLLAEVKQTQQTLGGIIHLWSLDEVTLTEA

QHRGCESILYLLQTLYEQEISSKVWIATRGTQRVTLQENSLSHLQGTLWGLSKVVALEYSQYWGGIIDLD
```

-continued

PEHDPQEAQFFLSEIFNSQKETYLAFRKGQRYVTRLKKATLTPQKLSLYQEGTYLITGGLGAVGLKVAQW

LVKEGAKHLVLMGRSQPSANAQEILNTLEEKGVNLSIVQGDVTELEDINRIFNQIKNSHPPLKGIIHAAG

LLKDGILQGLSWESFQQVLAPKVQGTWNLHQASLDLSLDFFVMFSSAASLLGSPGQGNYAAANGFLDAFA

HYRHSLGLPGLTINWGALSAGMATSTRLGVKGLEMIEIESALEMLSSLLTTSTPQVGVLSVKWDSLSEQF

PDLLKTPFFQEVISQDNKPSHEHSEIFTTLLTLSPPQRTEVLITYLQSSIARILHLSPADISPSDSLVDL

GMDSLMVMEAINTLKKDLQLMLYPREIYEHPKIEALATYLGTEFEGTHGQSPKSPQHNPQKQELVVSRFS

KTYQPLTITKKLPGIIFILSSPRAGSTLLRVMFAGHPDLISPPELHLLPFNTMGQRDQELALSYLGEGLQ

RAFMELGGLDSQTSQSLIEELIHQNTSIPDVYQRLQELAGNRLLVDKSPTYGMQREILDRGEAMFEGAKY

IHLVRHPYSVIDSFSRMRMDKLVGVSGDNPYSIAESVWLESNRNILDFSQTIDKERYYQLRYEDLVTQPS

QMMRSLCEFLDIPFNSALLDPYQGDRMTDGVYNQSISVGDPNFSQRRQIDPKLADAWKKIHLPQPLGDTT

LRLAASFNYELPHETVLPSPPRRGVGGEVISIPMQENYLTIRGLKLCLCSWGPEDGELILCIHGILEQGA

AWEEVATRLAQKGYRVIAPDLRGHGKSDHVGNGGSYNLIDFLGDLDAIATHLTDKPFTLVGHSLGSIIAA

MFTSIRPEKVKHLVLVETVLPTEVHEGDTVEQLATHLNYLSSPPKHPVFPDVETAAKRLQTATPAMSEQL

AMKLAKRITQAGEGGIQWRWDSLLRTRAGIEFNGINRSRYLSLLKQIQAKITLIYGDQSDFNRPEDLQLQ

QQTMSQANRIVVNGGHNLHLEAFEELANIING

NonA homolog from *Cyanothece* sp. PCC7822 ZP_03153601.1

SEQ ID NO: 9

MKRNFSNFVDLLNHQAEAQSDKTIFTFLGDGESETLSLTYQQLDQQARAIAVQLQSLQAAGERALLLYQP

GLEFISAFFGCLYGGVIPVPAYPPRANRSIERLQAIVSDAEAKFALTTQGIVSTIEGKLTQSQISTEAIQ

CVTTDNLELSLSNQWRRPNLKPDQLAFLQYTSGSTGNPKGVMVSHGNLMHNAALINGYFRDTPSSRGASW

LPPYHDMGLIGGILQPIYADVYVVLMPPVTFLQRPLRWLEVISRYRITTSGAPNFAYELCATQITPEQRE

NLDLSCWELAFSGAEPVRAQTLAQFAEAFAPCGFRKEAFYPCYGMAETTLIVSGGTRGVYPLLKDFDAKG

IEKNQVIPSSPLEPNNLTLVSCGKISGGQKVIIVNPDTLKQCDNYQIGEIWVNSESVAKGYWKRPQLTEA

IFNAYTADTQEGPFLRTGDLGFLEDGELFVTGRLKDLIIIRGRNHYPQDIEMTAEKSHPALRESCGAAFS

VEVGEEERLVITYEVKRSYIRKLNVEEVTSAIRKAVTQTHELQPYAIVLLKTGSIPKTSSGKIQRHACKA

EFLEGSLNSVGQWSAAQTLPKTSKQLLEVNSRKKRGHIIKSNPQQEIIENWLVTNIAQRLGLSPTEIEIT

EPPFASYGLDSVQAVRITAELEDWLKVKLSPTLAYDHPTVESLAKYLASGTVETTLATSKPLKTSSSVAII

GMSCRLPGANSPDEFWQLLRQGKDQITQVNARWDRDDWGGYLKGVDLFDAQFFGISPREAQEMDPQQRLL

LEVSWEALEKAALAANQLAGSNTGVFIGISSHDYSQIRLKNALEPSAYAGTGNAASIAANRLSYLYDFRG

PSLTVDTACSSSLVAIHLAIKSLQSGECQMALAGGVNILLSPELSETFTQAGMMAPDGRCKTFDESADGY

VRGEGCGVIVLKSLEDAIRDGDPILGVIHGSAINQDGRSNGLTAPNGIAQQGVIRQALMNAGMSAADISY

VETHGTGTALGDPIEVNSLKSVLMEGRSEKHPLWLGSVKTNIGHLEAAAGIAGLIKVLLCLQHQEIPPHL

HLYRLNSHINLDDSPISIPTQLTPWKPENRPRLAGVSSFGFGGTNAHIIVGEYQNLSPTKRGQVEELERP

LHILTLAAKREKDLSSLVKSYQHYLTAFPSASLEDICFTANNGRTQFKNRLAIIAQSREQLAEKLSRGEF

ITPQIAQKLNPKIAFLFTGQGSQYIGMGYQLYQTQPTFRAALNTCADLLEPYLEYPLLEVLYPQENSNLA

HYLDQTAYTQPALFALEYALAQLWLSWGIEPSVVMGHSVGEYVAATLAGVFSLEDGLKLIAHRGKLMQSL

PQNGQMVAVLSDEETVKKAINSHDEKVVIAAINGERNLVISGENQAIIEVTDRLTHQGIKTKPLQVSHAF

HSPLMQPMLEEFASIAREVEYSLPQIPLVSNVSGNLAAEAIATPEYWVNHVINPVHFSPSIKLMESKGYQ

IFLEIGAKPTLLGMGRSIIESDSSVNHQNAYLWLPSLRPGQSDWQQMLTSLAQLYVQGINIDWAGFEADY

QRQRMGGLPTYPFERQRYWLKPELEIHTGTKRLTTEQVSPPNQDWLYQVVWEAKPINPHQLSNQKTSTWL

IFGDQQGLAKTVAEQLEKLGKTSLLVQSDKGDKNGNHKTLNPTEKNDFQRLLTPFKTSGESLEGIIYLWS

-continued

LEEDEISKSNPQSILYLLQTLYEQNLSSRLWIATRGIQPVTTEDLAAPHIPLQGMLWGLGKVIALEYSDY

WGGLIDIGTQPHTDEAKLLLSAIINPDGEQYLAFRDGQRYVARIDKAEIKPKKFSIDENGSYLITGGLGA

VGLKVAQWLAKAGAKHLILMGRSHPTANAQETIKHLEKQGIEIIAQADVTRQEDIDRVFNQIKTPLKGI

IHAAGLLDDGILQGLSWEKFKKVLAPKVEGTWNLHKASLNHPLDFFVMFSSAASLFGSPGQGNYAAANGF

LDGMAYYRQSQGLPALTVNWGALSGGMAKATRLAVKGLDLIDIEPALDILSHLLADKIAQIGVVSVDWET

LAQQFPQLRQSPYFQRVITQLSPEQVKPDHSQSQILANLLALSPEQRTEALTAYLQSAMAQIMQLSPSQI

SGEDSLLDIGMDSLMIMEAINQLKRDLQLMLYPREIYQHPKIEALANYLAAEFERTHGKGQIPVTSKQEL

VVSRLTIANQPLTITKKLPGILFILSSPRAGSTLLRVMLAGHPDLASPPELHLLPFNSMGQRNQELALSY

LGEGLQRAFMDLQGLDSATSQQLIERLIAEDISIPDVYEMLQQSAGKRLLVDKSPTYGMQREILDRAEAI

FEGAKYIHLVRHPYPVIDSFCRMRMDKLVGSEGDNPYQLAESIWWESNRNIIEFSKTISSDRYYQLRYED

LVTQPSQAMQALCEFLDIPFDSALLDPYQGQRMTDGVYNQSMSVGDPNFSKRKQIDPKLADAWKDIQLPH

PLGDNTRQLAISLNYPLPHQNIPPLLRGEGGITEEVHLEEEYINIRGLNLCLCSWGPKQGELILCVHGIL

EQGAAWGQMATRLAGLGYRVVAPDLRGQGKSDHVGKGGSYNLIDFLADLDAIANSLTDQPFTLVGHSLGS

IIAAMFTSIRPEKVKNLVLVETVLPTEVSQTDAVEQLATHLNYLASPPEHPVFPDVETAAKRLQTATPAM

SEALAISLAKRITEPCEGGIRWRWDSLLRTRAGIEFNGINRSRYISLLEQIQAPITLIYGDNSDFNRPED

LQAQQKAMSAAKRIILKGGHNLHLDAYEQLANIIKQILGKTGQSF

---

What is claimed is:

1. A method for the biosynthetic production of 1-alkenes, comprising:

culturing an engineered microorganism in a culture medium, wherein said engineered microorganism comprises a recombinant 1-alkene synthase, wherein said 1-alkene synthase is at least 95% identical to SEQ ID NO: 2, and wherein the amount of said 1-alkenes produced by said engineered microorganism is greater than the amount that would be produced by an otherwise identical microorganism, cultured under identical conditions, but lacking said recombinant 1-alkene synthase.

2. The method of claim 1, wherein said recombinant 1-alkene synthase is an endogenous 1-alkene synthase expressed, at least in part, from a promoter other than its native promoter.

3. The method of claim 1, wherein said recombinant 1-alkene synthase is a heterologous 1-alkene synthase.

4. The method of claim 1, wherein said recombinant 1-alkene synthase is expressed from a heterologous promoter.

5. The method of claim 4, wherein said 1-alkene synthase is endogenous to said microorganism.

6. The method of claim 1, wherein said engineered microorganism is a photosynthetic microorganism, and wherein exposing said engineered microorganism to light and carbon dioxide results in the production of alkenes by said microorganism.

7. The method of claim 6, wherein said engineered microorganism is a cyanobacterium.

8. The method of claim 1 or 6, wherein said 1-alkenes are selected from the group consisting of 1-nonadecene and 1-octadecene.

9. The method of claim 1 or 6, further comprising isolating said 1-alkenes from said cyanobacterium or said culture medium.

10. A method for the biosynthetic production of an olefin, comprising
   (1) culturing a cyanobacterium in a culture medium, wherein said cyanobacterium comprises a 1-alkene synthase activity, wherein said 1-alkene synthase is at least 95% identical to SEQ ID NO: 2, and wherein said culture medium comprises an exogenous fatty acid;
   (2) exposing said engineered cyanobacterium to light and carbon dioxide, wherein said exposure results in the production of an olefin by said cyanobacterium, and wherein the amount of said olefin produced is greater than the amount that would be produced by an otherwise identical cyanobacterium, cultured under identical conditions but in the absence of said exogenous fatty acid.

11. The method of claim 10, wherein said concentration of said fatty acid in said culture medium is at least 1 µg/ml.

12. The method of claim 11, wherein said fatty acid is an odd-chain fatty acid.

13. The method of claim 12, wherein said odd-chain fatty acid is tridecanoic acid and said olefin is 1-octadecene.

14. The method of claim 13, wherein the amount of said 1-octadecene produced is at least 0.039% dry cell weight.

15. The method of claim 10, further comprising isolating said olefin from said cyanobacterium or said culture medium.

16. A method for the biosynthetic production of alkenes, comprising
   (1) culturing an engineered microorganism in a culture medium, wherein said engineered microorganism comprises a modification, wherein said modification reduces the activity of a hydrolase having an amino acid sequence that has at least 95% sequence identity to SEQ ID NO:4; and
   (2) exposing said engineered microorganism to light and carbon dioxide, wherein said exposure results in the production of alkenes by said engineered microorganisms, wherein said alkenes comprise 1-alkenes, and wherein the amount of 1-alkenes produced is greater than the amount that would be produced by an otherwise identical microorganism, cultured under identical conditions, but lacking said modification.

17. The method of claim 16, wherein said 1-alkenes include 1-nonadecene.

18. The method of claim 16, wherein said microorganism is a cyanobacteria.

* * * * *

SEQUENCE LISTING

<160> NUMBER OF SEQ ID NOS: 9

<210> SEQ ID NO 1
<211> LENGTH: 8163
<212> TYPE: DNA
<213> ORGANISM: Synechococcus sp.

<400> SEQUENCE: 1

| | | | | | |
|---|---|---|---|---|---|
| atggttggtc | aatttgcaaa | tttcgtcgat | ctgctccagt | acagagctaa | acttcaggcg | 60 |
| cggaaaaccg | tgtttagttt | tctggctgat | ggcgaagcgg | aatctgcggc | cctgacctac | 120 |
| ggagaattag | accaaaaagc | ccaggcgatc | gccgcttttt | tgcaagctaa | ccaggctcaa | 180 |
| gggcaacggg | cattattact | ttatccaccg | ggtttagagt | ttatcggtgc | cttttttggga | 240 |
| tgtttgtatg | ctggtgttgt | tgcggtgcca | gcttacccac | cacggccgaa | taaatccttt | 300 |
| gaccgcctcc | atagcattat | tcaagatgcc | caggcaaaat | tgccctcac | cacaacagaa | 360 |
| cttaaagata | aaattgccga | tcgcctcgaa | gctttagaag | gtacggattt | tcattgtttg | 420 |
| gctacagatc | aagttgaatt | aatttcagga | aaaaattggc | aaaaaccgaa | catttccggc | 480 |
| acagatctcg | cttttttgca | atacaccagt | ggctccacgg | gcgatcctaa | aggagtgatg | 540 |
| gtttcccacc | acaatttgat | ccacaactcc | ggcttgatta | ccaaggatt | ccaggataca | 600 |
| gaggcgagta | tgggcgtttc | ctggttgccg | ccctaccatg | atatgggctt | gatcggtggg | 660 |
| atttacagc | ccatctatgt | gggagcaacg | caaattttaa | tgcctcccgt | ggccttttg | 720 |
| cagcgacctt | ttcggtggct | aaaggcgatc | aacgattatc | gggtttccac | cagcggtgcg | 780 |
| ccgaattttg | cctatgatct | ctgtgccagc | caaattaccc | cggaacaaat | cagagaactc | 840 |
| gatttgagct | gttggcgact | ggcttttttcc | ggggccgaac | cgatccgcgc | tgtgaccctc | 900 |
| gaaaattttg | cgaaaccctt | cgctacagca | ggctttcaaa | aatcagcatt | ttatccctgt | 960 |
| tatggtatgg | ctgaaaccac | cctgatcgtt | tccggtggta | atggtcgtgc | ccagcttccc | 1020 |

```
caggaaatta tcgtcagcaa acagggcatc gaagcaaacc aagttcgccc tgcccaaggg    1080
acagaaacaa cggtgacctt ggtcggcagt ggtgaagtga ttggcgacca aattgtcaaa    1140
attgttgacc cccaggcttt aacagaatgt accgtcggtg aaattggcga agtatgggtt    1200
aagggcgaaa gtgttgccca gggctattgg caaaagccag acctcaccca gcaacaattc    1260
cagggaaacg tcggtgcaga aacgggcttt ttacgcacgg gcgatctggg ttttttgcaa    1320
ggtggcgaac tgtatattac gggtcgttta aaggatctcc tgattatccg ggggcgcaac    1380
cactatcccc aggacattga attaaccgtc gaagtggccc atcccgcttt acgacagggg    1440
gccggagccg ctgtatcagt agacgttaac ggggaagaac agttagtcat tgtccaggaa    1500
gttgagcgta aatatgcccg caaattaaat gtcgcggcag tagcccaagc tattcgtggg    1560
gcgatcgccg ccgaacatca actgcaaccc caggccattt gttttattaa acccggtagc    1620
attcccaaaa catccagcgg gaagattcgt cgccatgcct gcaaagctgg ttttctagac    1680
ggaagcttgg ctgtggttgg ggagtggcaa cccagccacc aaaaagaagg aaaaggaatt    1740
gggacacaag ccgttacccc ttctacgaca acatcaacga attttcccct gcctgaccag    1800
caccaacagc aaaattgaagc ctggcttaag gataatattg cccatcgcct cggcattacg    1860
ccccaacaat tagacgaaac ggaaccctttt gcaagttatg ggctggattc agtgcaagca    1920
gtacaggtca cagccgactt agaggattgg ctaggtcgaa aattagaccc cactctggcc    1980
tacgattatc cgaccattcg caccctggct cagttttttgg tccagggtaa tcaagcgcta    2040
gagaaaatac cacaggtgcc gaaaattcag ggcaaagaaa ttgccgtggt gggtctcagt    2100
tgtcgttttc cccaagctga caaccccgaa gcttttttggg aattattacg taatggtaaa    2160
gatggagttc gcccccttaa aactcgctgg gccacgggag aatggggtgg ttttttagaa    2220
gatattgacc agtttgagcc gcaattttttt ggcatttccc cccggaagc ggaacaaatg    2280
gatccccagc aacgcttact gttagaagta acctgggaag ccttggaacg ggcaaatatt    2340
ccggcagaaa gttacgcca ttcccaaacg gggggttttg tcggcattag taatagtgat    2400
tatgcccagt tgcaggtgcg ggaaaacaat ccgatcaatc cctacatggg gacgggcaac    2460
gcccacagta ttgctgcgaa tcgtctgtct tatttcctcg atctccgggg cgtttctctg    2520
agcatcgata cggcctgttc ctcttctctg gtggcggtac atctggcctg tcaaagtttta    2580
atcaacggcg aatcggagtt ggcgatcgcc gccggggtga atttgatttt gacccccgat    2640
gtgacccaga cttttaccca ggcgggcatg atgagtaaga cgggccgttg ccagaccttt    2700
gatgccgagc tgatggctga tgtgcggggc gaaggttgtg gggtcgttct cctcaaaccc    2760
ctggcccagg cagaacggga cggggataat attctcgcgg tgatccacgg ttcggcggtg    2820
aatcaagatg gacgcagtaa cggttttgacg gctcccaacg ggcgatcgca acaggccgtt    2880
attcgccaag ccctggccca agccggcatt accgccgccg atttagctta cctagaggcc    2940
cacggcaccg gcacgcccct gggtgatccc attgaaatta attccctgaa ggcggttttta    3000
caaacggcgc agcgggaaca gccctgtgtg gtgggttctg tgaaaacaaa cattggtcac    3060
ctcgaggcag cggcgggcat cgcgggctta atcaaggtga ttttgtccct agagcatgga    3120
atgattcccc aacatttgca ttttaagcag ctcaatcccc gcattgatct agacggttta    3180
gtgaccattg cgagcaaaga tcagccttgg tcaggcgggt cacaaaaacg gtttgctggg    3240
gtaagttcct ttgggtttgg tggcaccaat gcccacgtga ttgtcgggga ctatgctcaa    3300
caaaaatctc cccttgctcc tccggctacc caagaccgcc cttggcattt gctgacccttt    3360
tctgctaaaa atgcccaggc cttaaatgcc ctgcaaaaaa gctatggaga ctatctggcc    3420
```

```
caacatccca gcgttgaccc acgcgatctc tgtttgtctg ccaataccgg gcgatcgccc      3480
ctcaaagaac gtcgtttttt tgtctttaaa caagtcgccg atttacaaca aactctcaat      3540
caagattttc tggcccaacc acgcctcagt tcccccgcaa aaattgcctt tttgtttacg      3600
gggcaaggtt cccaatacta cggcatgggg caacaactgt accaaaccag cccagtattt      3660
cggcaagtgc tggatgagtg cgatcgcctc tggcagacct attccccga agcccctgcc      3720 ctcaccgacc tgctgtacgg taaccataac cctgacctcg tccacgaaac tgtctatacc      3780
cagcccctcc tctttgctgt tgaatatgcg atcgcccaac tatggttaag ctggggcgtg      3840
acgccagact tttgcatggg ccatagcgtc ggcgaatatg tcgcggcttg tctggcgggg      3900
gtattttccc tggcagacgg catgaaatta attacggccc ggggcaaact gatgcacgcc      3960
ctacccagca atggcagtat ggcggcggtc tttgccgata aaacggtcat caaaccctac      4020
ctatcggagc atttgaccgt cggagccgaa aacggttccc atttggtgct atcaggaaag      4080
accccctgcc tcgaagccag tattcacaaa ctccaaagcc aagggatcaa aaccaaaccc      4140
ctcaaggttt cccatgcttt ccactcccct ttgatggctc ccatgctggc agagtttcgg      4200
gaaattgctg aacaaattac tttccacccg ccgcgtatcc cgctcatttc caatgtcacg      4260
ggcggccaga ttgaagcgga aattgcccag gccgactatt gggttaagca cgtttcgcaa      4320
cccgtcaaat ttgtccagag catccaaacc ctggcccaag cgggtgtcaa tgtttatctc      4380
gaaatcggcg taaaaccagt gctcctgagt atgggacgcc attgcttagc tgaacaagaa      4440
gcggtttggt tgcccagttt acgtccccat agtgagcctt ggccggaaat tttgaccagt      4500
ctcggcaaac tgtatgagca agggctaaac attgactggc agaccgtgga agctggcgat      4560
cgccgccgga aactgattct gcccaccttat cccttccaac ggcaacgata ttggttttaat      4620 caaggctctt ggcaaactgt tgagaccgaa tctgtgaacc caggccctga cgatctcaat      4680
gattggttgt atcaggtggc gtggacgccc tggacacctt tgcccccggc ccctgaaccg      4740
tcggctaagc tgtggttaat cttgggcgat cgccatgatc accagcccat tgaagcccaa      4800
tttaaaaacg cccagcgggt gtatctcggc caaagcaatc atttccgac gaatgccccc      4860 tgggaagtat ctgccgatgc gttggataat ttatttactc acgtcggctc ccaaaattta      4920
gcaggcatcc tttacctgtg tccccaggg gaagacccag aagacctaga tgaaattcaa      4980
aagcaaacca gtggcttcgc cctccaactg atccaaaccc tgtatcaaca aaagatcgcg      5040
gttccctgct ggtttgtgac ccaccagagc caacgggtgc ttgaaaaccga tgctgtcacc      5100 ggatttgccc aaggggggatt atggggactc gcccaggcga tcgccctcga acatccagag      5160
ttgtgggggg gaattattga tgtcgatgac agcctgccaa attttgccca gatttgccaa      5220
caaagacagg tgcagcagtt ggccgtgcgg caccaaaaac tctacggggc acagctcaaa      5280
aagcaaccgt cactgcccca gaaaaatctc cagattcaac cccaacagac ctatctagtg      5340 acaggggac tgggggccat tggccgtaaa attgcccaat ggctagccgc agcaggagca      5400
gaaaaagtaa ttctcgtcag ccggcgcgct ccggcagcgg atcagcagac gttaccgacc      5460
aatgcggtgg tttatccttg cgatttagcc gacgcagccc aggtggcaaa gctgtttcaa      5520
acctatcccc acatcaaagg aatttttccat gcggcgggta ccttagctga tggtttgctg      5580
caacaacaaa cttggcaaaa gttccagacc gtcgccgccg ccaaaatgaa agggacatgg      5640
catctgcacc gccatagtca aaagctcgat ctggattttt ttgtgttgtt ttcctctgtg      5700
gcaggggtgc tcggttcacc gggacagggg aattatgccg ccgcaaaccg gggcatggcg      5760
```

| | |
|---|---|
| gcgatcgccc aatatcgaca agcccaaggt ttacccgccc tggcgatcca ttgggggcct | 5820 |
| tgggccgaag ggggaatggc caactccctc agcaaccaaa atttagcgtg gctgccgccc | 5880 |
| ccccagggac taacaatcct cgaaaaagtc ttgggcgccc agggggaaat ggggtctttt | 5940 |
| aaaccggact ggcaaaacct ggccaaacag ttccccgaat tgccaaaac ccattacttt | 6000 |
| gcagccgtta ttccctctgc tgaggctgtg cccccaacgg cttcaatttt tgacaaatta | 6060 |
| atcaacctag aagcttctca gcgggctgac tatctactgg attatctgcg gcggtctgtg | 6120 |
| gcgcaaatcc tcaagttaga aattgagcaa attcaaagcc acgatagcct gttggatctg | 6180 |
| ggcatggatt cgttgatgat catggaggcg atcgccagcc tcaagcagga tttacaactg | 6240 |
| atgttgtacc ccagggaaat ctacgaacgg cccagacttg atgtgttgac ggcctatcta | 6300 |
| gcggcggaat tcaccaaggc ccatgattct gaagcagcaa cggcggcagc agcgattccc | 6360 |
| tcccaaagcc tttcggtcaa acaaaaaaaa cagtggcaaa aacctgacca caaaaacccg | 6420 |
| aatcccattg cctttatcct ctctagcccc cggtcgggtt cgacgttgct gcgggtgatg | 6480 |
| ttagccggac atccggggtt atattcgccg ccagagctgc atttgctccc ctttgagact | 6540 |
| atgggcgatc gccaccagga attgggtcta tcccacctcg gcgaagggtt acaacgggcc | 6600 |
| ttaatggatc tagaaaacct caccccagag gcaagccagg cgaaggtcaa ccaatgggtc | 6660 |
| aaagcgaata cacccattgc agacatctat gcctatctcc aacggcaggc ggaacaacgt | 6720 |
| ttactcatcg acaaatctcc cagctacggc agcgatcgcc atattctaga ccacagcgaa | 6780 |
| atcctctttg accaggccaa atatatccat ctggtacgcc atccctacgc ggtgattgaa | 6840 |
| tcctttaccc gactgcggat ggataaactg ctggggccg agcagcagaa cccctacgcc | 6900 |
| ctcgcggagt ccatttggcg caccagcaac cgcaatattt tagacctggg tcgcacggtt | 6960 |
| ggtgcggatc gatatctcca ggtgatttac gaagatctcg tccgtgaccc ccgcaaagtt | 7020 |
| ttgacaaata tttgtgattt cctggggtg gactttgacg aagcgctcct caatccctac | 7080 |
| agcggcgatc gccttaccga tggcctccac caacagtcca tgggcgtcgg ggatcccaat | 7140 |
| ttcctccagc acaaaaccat tgatccggcc ctcgccgaca aatggcgctc aattaccctg | 7200 |
| cccgctgctc tccagctgga tacgatccag ttggccgaaa cgtttgctta cgatctcccc | 7260 |
| caggaacccc agctaacacc ccagacccaa tccttgccct cgatggtgga gcggttcgtg | 7320 |
| acagtgcgcg gtttagaaac ctgtctctgt gagtggggcg atcgccacca accattggtg | 7380 |
| ctacttctcc acggcatcct cgaacagggg gcctcctggc aactcatcgc gccccagttg | 7440 |
| gcggcccagg gctattgggt tgtggcccca gacctgcgtg gtcacggcaa atccgcccat | 7500 |
| gcccagtcct acagcatgct tgattttttg gctgacgtag atgcccttgc caaacaatta | 7560 |
| ggcgatcgcc cctttacctt ggtgggccac tccatgggtt ccatcatcgg tgccatgtat | 7620 |
| gcaggaattc gccaaaccca ggtagaaaag ttgatcctcg ttgaaaccat tgtccccaac | 7680 |
| gacatcgacg acgctgaaac cggtaatcac ctgacgaccc atctcgatta cctgccgcg | 7740 |
| ccccccaac acccgatctt ccccagccta gaagtggccg cccgtcgcct ccgccaagcc | 7800 |
| acgcccaac tacccaaaga cctctcggcg ttcctcaccc agcgcagcac caaatccgtc | 7860 |
| gaaaagggg tgcagtggcg ttgggatgct tcctccgta cccggcggg cattgaattc | 7920 |
| aatggcatta gcagacgacg ttacctggcc ctgctcaaag atatccaagc gccgatcacc | 7980 |
| ctcatctatg gcgatcagag tgaatttaac cgccctgctg atctccaggc gatccaagcg | 8040 |
| gctctccccc aggcccaacg tttaacggtt gctggcggcc ataacctcca ttttgagaat | 8100 |
| ccccaggcga tcgcccaaat tgtttatcaa caactccaga cccctgtacc caaaacacaa | 8160 |

```
                                                                        taa                              8163

<210> SEQ ID NO 2
<211> LENGTH: 2720
<212> TYPE: PRT
<213> ORGANISM: Synechococcus sp.

<400> SEQUENCE: 2

Met Val Gly Gln Phe Ala Asn Phe Val Asp Leu Leu Gln Tyr Arg Ala
1               5                   10                  15

Lys Leu Gln Ala Arg Lys Thr Val Phe Ser Phe Leu Ala Asp Gly Glu
            20                  25                  30

Ala Glu Ser Ala Ala Leu Thr Tyr Gly Glu Leu Asp Gln Lys Ala Gln
        35                  40                  45

Ala Ile Ala Ala Phe Leu Gln Ala Asn Gln Ala Gln Gly Gln Arg Ala
    50                  55                  60

Leu Leu Leu Tyr Pro Pro Gly Leu Glu Phe Ile Gly Ala Phe Leu Gly
65                  70                  75                  80

Cys Leu Tyr Ala Gly Val Val Ala Val Pro Ala Tyr Pro Pro Arg Pro
                85                  90                  95

Asn Lys Ser Phe Asp Arg Leu His Ser Ile Ile Gln Asp Ala Gln Ala
            100                 105                 110

Lys Phe Ala Leu Thr Thr Thr Glu Leu Lys Asp Lys Ile Ala Asp Arg
        115                 120                 125

Leu Glu Ala Leu Glu Gly Thr Asp Phe His Cys Leu Ala Thr Asp Gln
    130                 135                 140

Val Glu Leu Ile Ser Gly Lys Asn Trp Gln Lys Pro Asn Ile Ser Gly
145                 150                 155                 160

Thr Asp Leu Ala Phe Leu Gln Tyr Thr Ser Gly Ser Thr Gly Asp Pro
                165                 170                 175

Lys Gly Val Met Val Ser His His Asn Leu Ile His Asn Ser Gly Leu
            180                 185                 190

Ile Asn Gln Gly Phe Gln Asp Thr Glu Ala Ser Met Gly Val Ser Trp
        195                 200                 205

Leu Pro Pro Tyr His Asp Met Gly Leu Ile Gly Ile Leu Gln Pro
    210                 215                 220

Ile Tyr Val Gly Ala Thr Gln Ile Leu Met Pro Pro Val Ala Phe Leu
225                 230                 235                 240

Gln Arg Pro Phe Arg Trp Leu Lys Ala Ile Asn Asp Tyr Arg Val Ser
                245                 250                 255

Thr Ser Gly Ala Pro Asn Phe Ala Tyr Asp Leu Cys Ala Ser Gln Ile
            260                 265                 270

Thr Pro Glu Gln Ile Arg Glu Leu Asp Leu Ser Cys Trp Arg Leu Ala
        275                 280                 285

Phe Ser Gly Ala Glu Pro Ile Arg Ala Val Thr Leu Glu Asn Phe Ala
    290                 295                 300

Lys Thr Phe Ala Thr Ala Gly Phe Gln Lys Ser Ala Phe Tyr Pro Cys
305                 310                 315                 320

Tyr Gly Met Ala Glu Thr Thr Leu Ile Val Ser Gly Gly Asn Gly Arg
                325                 330                 335

Ala Gln Leu Pro Gln Glu Ile Ile Val Ser Lys Gln Gly Ile Glu Ala
            340                 345                 350

Asn Gln Val Arg Pro Ala Gln Gly Thr Glu Thr Thr Val Thr Leu Val
        355                 360                 365
```

```
Gly Ser Gly Glu Val Ile Gly Asp Gln Ile Val Lys Ile Val Asp Pro
    370                 375                 380

Gln Ala Leu Thr Glu Cys Thr Val Gly Glu Ile Gly Glu Val Trp Val
385                 390                 395                 400

Lys Gly Glu Ser Val Ala Gln Gly Tyr Trp Gln Lys Pro Asp Leu Thr
                405                 410                 415

Gln Gln Gln Phe Gln Gly Asn Val Gly Ala Glu Thr Gly Phe Leu Arg
            420                 425                 430

Thr Gly Asp Leu Gly Phe Leu Gln Gly Gly Glu Leu Tyr Ile Thr Gly
        435                 440                 445

Arg Leu Lys Asp Leu Leu Ile Ile Arg Gly Arg Asn His Tyr Pro Gln
    450                 455                 460

Asp Ile Glu Leu Thr Val Glu Val Ala His Pro Ala Leu Arg Gln Gly
465                 470                 475                 480

Ala Gly Ala Ala Val Ser Val Asp Val Asn Gly Glu Glu Gln Leu Val
                485                 490                 495

Ile Val Gln Glu Val Glu Arg Lys Tyr Ala Arg Lys Leu Asn Val Ala
            500                 505                 510

Ala Val Ala Gln Ala Ile Arg Gly Ala Ile Ala Ala Glu His Gln Leu
        515                 520                 525

Gln Pro Gln Ala Ile Cys Phe Ile Lys Pro Gly Ser Ile Pro Lys Thr
    530                 535                 540

Ser Ser Gly Lys Ile Arg Arg His Ala Cys Lys Ala Gly Phe Leu Asp
545                 550                 555                 560

Gly Ser Leu Ala Val Val Gly Glu Trp Gln Pro Ser His Gln Lys Glu
                565                 570                 575

Gly Lys Gly Ile Gly Thr Gln Ala Val Thr Pro Ser Thr Thr Thr Ser
            580                 585                 590

Thr Asn Phe Pro Leu Pro Asp Gln His Gln Gln Ile Glu Ala Trp
        595                 600                 605

Leu Lys Asp Asn Ile Ala His Arg Leu Gly Ile Thr Pro Gln Gln Leu
    610                 615                 620

Asp Glu Thr Glu Pro Phe Ala Ser Tyr Gly Leu Asp Ser Val Gln Ala
625                 630                 635                 640

Val Gln Val Thr Ala Asp Leu Glu Asp Trp Leu Gly Arg Lys Leu Asp
                645                 650                 655

Pro Thr Leu Ala Tyr Asp Tyr Pro Thr Ile Arg Thr Leu Ala Gln Phe
            660                 665                 670

Leu Val Gln Gly Asn Gln Ala Leu Glu Lys Ile Pro Gln Val Pro Lys
        675                 680                 685

Ile Gln Gly Lys Glu Ile Ala Val Val Gly Leu Ser Cys Arg Phe Pro
    690                 695                 700

Gln Ala Asp Asn Pro Glu Ala Phe Trp Glu Leu Leu Arg Asn Gly Lys
705                 710                 715                 720

Asp Gly Val Arg Pro Leu Lys Thr Arg Trp Ala Thr Gly Glu Trp Gly
                725                 730                 735

Gly Phe Leu Glu Asp Ile Asp Gln Phe Glu Pro Gln Phe Phe Gly Ile
            740                 745                 750

Ser Pro Arg Glu Ala Glu Gln Met Asp Pro Gln Gln Arg Leu Leu Leu
        755                 760                 765

Glu Val Thr Trp Glu Ala Leu Glu Arg Ala Asn Ile Pro Ala Glu Ser
    770                 775                 780
```

```
Leu Arg His Ser Gln Thr Gly Val Phe Val Gly Ile Ser Asn Ser Asp
785                 790                 795                 800

Tyr Ala Gln Leu Gln Val Arg Glu Asn Asn Pro Ile Asn Pro Tyr Met
                805                 810                 815

Gly Thr Gly Asn Ala His Ser Ile Ala Ala Asn Arg Leu Ser Tyr Phe
                820                 825                 830

Leu Asp Leu Arg Gly Val Ser Leu Ser Ile Asp Thr Ala Cys Ser Ser
                835                 840                 845

Ser Leu Val Ala Val His Leu Ala Cys Gln Ser Leu Ile Asn Gly Glu
            850                 855                 860

Ser Glu Leu Ala Ile Ala Ala Gly Val Asn Leu Ile Leu Thr Pro Asp
865                 870                 875                 880

Val Thr Gln Thr Phe Thr Gln Ala Gly Met Met Ser Lys Thr Gly Arg
                885                 890                 895

Cys Gln Thr Phe Asp Ala Glu Ala Asp Gly Tyr Val Arg Gly Glu Gly
                900                 905                 910

Cys Gly Val Val Leu Leu Lys Pro Leu Ala Gln Ala Glu Arg Asp Gly
                915                 920                 925

Asp Asn Ile Leu Ala Val Ile His Gly Ser Ala Val Asn Gln Asp Gly
                930                 935                 940

Arg Ser Asn Gly Leu Thr Ala Pro Asn Gly Arg Ser Gln Gln Ala Val
945                 950                 955                 960

Ile Arg Gln Ala Leu Ala Gln Ala Gly Ile Thr Ala Ala Asp Leu Ala
                965                 970                 975

Tyr Leu Glu Ala His Gly Thr Gly Thr Pro Leu Gly Asp Pro Ile Glu
                980                 985                 990

Ile Asn Ser Leu Lys Ala Val Leu  Gln Thr Ala Gln  Arg Glu Gln Pro
                995                 1000                1005

Cys Val  Val Gly Ser Val Lys  Thr Asn Ile Gly His  Leu Glu Ala
     1010                1015                 1020

Ala Ala  Gly Ile Ala Gly Leu  Ile Lys Val Ile Leu  Ser Leu Glu
     1025                1030                 1035

His Gly  Met Ile Pro Gln His  Leu His Phe Lys Gln  Leu Asn Pro
     1040                1045                 1050

Arg Ile  Asp Leu Asp Gly Leu  Val Thr Ile Ala Ser  Lys Asp Gln
     1055                1060                 1065

Pro Trp  Ser Gly Gly Ser Gln  Lys Arg Phe Ala Gly  Val Ser Ser
     1070                1075                 1080

Phe Gly  Phe Gly Gly Thr Asn  Ala His Val Ile Val  Gly Asp Tyr
     1085                1090                 1095

Ala Gln  Gln Lys Ser Pro Leu  Ala Pro Pro Ala Thr  Gln Asp Arg
     1100                1105                 1110

Pro Trp  His Leu Leu Thr Leu  Ser Ala Lys Asn Ala  Gln Ala Leu
     1115                1120                 1125

Asn Ala  Leu Gln Lys Ser Tyr  Gly Asp Tyr Leu Ala  Gln His Pro
     1130                1135                 1140

Ser Val  Asp Pro Arg Asp Leu  Cys Leu Ser Ala Asn  Thr Gly Arg
     1145                1150                 1155

Ser Pro  Leu Lys Glu Arg Arg  Phe Phe Val Phe Lys  Gln Val Ala
     1160                1165                 1170

Asp Leu  Gln Gln Thr Leu Asn  Gln Asp Phe Leu Ala  Gln Pro Arg
     1175                1180                 1185

Leu Ser  Ser Pro Ala Lys Ile  Ala Phe Leu Phe Thr  Gly Gln Gly
```

1190                1195               1200

Ser Gln Tyr Tyr Gly Met Gly Gln Gln Leu Tyr Gln Thr Ser Pro
    1205                1210                1215

Val Phe Arg Gln Val Leu Asp Glu Cys Asp Arg Leu Trp Gln Thr
    1220                1225                1230

Tyr Ser Pro Glu Ala Pro Ala Leu Thr Asp Leu Leu Tyr Gly Asn
    1235                1240                1245

His Asn Pro Asp Leu Val His Glu Thr Val Tyr Thr Gln Pro Leu
    1250                1255                1260

Leu Phe Ala Val Glu Tyr Ala Ile Ala Gln Leu Trp Leu Ser Trp
    1265                1270                1275

Gly Val Thr Pro Asp Phe Cys Met Gly His Ser Val Gly Glu Tyr
    1280                1285                1290

Val Ala Ala Cys Leu Ala Gly Val Phe Ser Leu Ala Asp Gly Met
    1295                1300                1305

Lys Leu Ile Thr Ala Arg Gly Lys Leu Met His Ala Leu Pro Ser
    1310                1315                1320

Asn Gly Ser Met Ala Ala Val Phe Ala Asp Lys Thr Val Ile Lys
    1325                1330                1335

Pro Tyr Leu Ser Glu His Leu Thr Val Gly Ala Glu Asn Gly Ser
    1340                1345                1350

His Leu Val Leu Ser Gly Lys Thr Pro Cys Leu Glu Ala Ser Ile
    1355                1360                1365

His Lys Leu Gln Ser Gln Gly Ile Lys Thr Lys Pro Leu Lys Val
    1370                1375                1380

Ser His Ala Phe His Ser Pro Leu Met Ala Pro Met Leu Ala Glu
    1385                1390                1395

Phe Arg Glu Ile Ala Glu Gln Ile Thr Phe His Pro Pro Arg Ile
    1400                1405                1410

Pro Leu Ile Ser Asn Val Thr Gly Gly Gln Ile Glu Ala Glu Ile
    1415                1420                1425

Ala Gln Ala Asp Tyr Trp Val Lys His Val Ser Gln Pro Val Lys
    1430                1435                1440

Phe Val Gln Ser Ile Gln Thr Leu Ala Gln Ala Gly Val Asn Val
    1445                1450                1455

Tyr Leu Glu Ile Gly Val Lys Pro Val Leu Leu Ser Met Gly Arg
    1460                1465                1470

His Cys Leu Ala Glu Gln Glu Ala Val Trp Leu Pro Ser Leu Arg
    1475                1480                1485

Pro His Ser Glu Pro Trp Pro Glu Ile Leu Thr Ser Leu Gly Lys
    1490                1495                1500

Leu Tyr Glu Gln Gly Leu Asn Ile Asp Trp Gln Thr Val Glu Ala
    1505                1510                1515

Gly Asp Arg Arg Arg Lys Leu Ile Leu Pro Thr Tyr Pro Phe Gln
    1520                1525                1530

Arg Gln Arg Tyr Trp Phe Asn Gln Gly Ser Trp Gln Thr Val Glu
    1535                1540                1545

Thr Glu Ser Val Asn Pro Gly Pro Asp Asp Leu Asn Asp Trp Leu
    1550                1555                1560

Tyr Gln Val Ala Trp Thr Pro Leu Asp Thr Leu Pro Pro Ala Pro
    1565                1570                1575

Glu Pro Ser Ala Lys Leu Trp Leu Ile Leu Gly Asp Arg His Asp
    1580                1585                1590

His Gln Pro Ile Glu Ala Gln Phe Lys Asn Ala Gln Arg Val Tyr
1595                1600                1605

Leu Gly Gln Ser Asn His Phe Pro Thr Asn Ala Pro Trp Glu Val
1610                1615                1620

Ser Ala Asp Ala Leu Asp Asn Leu Phe Thr His Val Gly Ser Gln
1625                1630                1635

Asn Leu Ala Gly Ile Leu Tyr Leu Cys Pro Pro Gly Glu Asp Pro
1640                1645                1650

Glu Asp Leu Asp Glu Ile Gln Lys Gln Thr Ser Gly Phe Ala Leu
1655                1660                1665

Gln Leu Ile Gln Thr Leu Tyr Gln Gln Lys Ile Ala Val Pro Cys
1670                1675                1680

Trp Phe Val Thr His Gln Ser Gln Arg Val Leu Glu Thr Asp Ala
1685                1690                1695

Val Thr Gly Phe Ala Gln Gly Gly Leu Trp Gly Leu Ala Gln Ala
1700                1705                1710

Ile Ala Leu Glu His Pro Glu Leu Trp Gly Gly Ile Ile Asp Val
1715                1720                1725

Asp Asp Ser Leu Pro Asn Phe Ala Gln Ile Cys Gln Gln Arg Gln
1730                1735                1740

Val Gln Gln Leu Ala Val Arg His Gln Lys Leu Tyr Gly Ala Gln
1745                1750                1755

Leu Lys Lys Gln Pro Ser Leu Pro Gln Lys Asn Leu Gln Ile Gln
1760                1765                1770

Pro Gln Gln Thr Tyr Leu Val Thr Gly Gly Leu Gly Ala Ile Gly
1775                1780                1785

Arg Lys Ile Ala Gln Trp Leu Ala Ala Ala Gly Ala Glu Lys Val
1790                1795                1800

Ile Leu Val Ser Arg Arg Ala Pro Ala Ala Asp Gln Gln Thr Leu
1805                1810                1815

Pro Thr Asn Ala Val Val Tyr Pro Cys Asp Leu Ala Asp Ala Ala
1820                1825                1830

Gln Val Ala Lys Leu Phe Gln Thr Tyr Pro His Ile Lys Gly Ile
1835                1840                1845

Phe His Ala Ala Gly Thr Leu Ala Asp Gly Leu Leu Gln Gln Gln
1850                1855                1860

Thr Trp Gln Lys Phe Gln Thr Val Ala Ala Ala Lys Met Lys Gly
1865                1870                1875

Thr Trp His Leu His Arg His Ser Gln Lys Leu Asp Leu Asp Phe
1880                1885                1890

Phe Val Leu Phe Ser Ser Val Ala Gly Val Leu Gly Ser Pro Gly
1895                1900                1905

Gln Gly Asn Tyr Ala Ala Ala Asn Arg Gly Met Ala Ala Ile Ala
1910                1915                1920

Gln Tyr Arg Gln Ala Gln Gly Leu Pro Ala Leu Ala Ile His Trp
1925                1930                1935

Gly Pro Trp Ala Glu Gly Gly Met Ala Asn Ser Leu Ser Asn Gln
1940                1945                1950

Asn Leu Ala Trp Leu Pro Pro Pro Gln Gly Leu Thr Ile Leu Glu
1955                1960                1965

Lys Val Leu Gly Ala Gln Gly Glu Met Gly Val Phe Lys Pro Asp
1970                1975                1980

-continued

Trp Gln Asn Leu Ala Lys Gln Phe Pro Glu Phe Ala Lys Thr His
1985              1990                1995

Tyr Phe Ala Ala Val Ile Pro Ser Ala Glu Ala Val Pro Pro Thr
2000              2005                2010

Ala Ser Ile Phe Asp Lys Leu Ile Asn Leu Glu Ala Ser Gln Arg
2015              2020                2025

Ala Asp Tyr Leu Leu Asp Tyr Leu Arg Arg Ser Val Ala Gln Ile
2030              2035                2040

Leu Lys Leu Glu Ile Glu Gln Ile Gln Ser His Asp Ser Leu Leu
2045              2050                2055

Asp Leu Gly Met Asp Ser Leu Met Ile Met Glu Ala Ile Ala Ser
2060              2065                2070

Leu Lys Gln Asp Leu Gln Leu Met Leu Tyr Pro Arg Glu Ile Tyr
2075              2080                2085

Glu Arg Pro Arg Leu Asp Val Leu Thr Ala Tyr Leu Ala Ala Glu
2090              2095                2100

Phe Thr Lys Ala His Asp Ser Glu Ala Thr Ala Ala Ala Ala
2105              2110                2115

Ile Pro Ser Gln Ser Leu Ser Val Lys Thr Lys Lys Gln Trp Gln
2120              2125                2130

Lys Pro Asp His Lys Asn Pro Asn Pro Ile Ala Phe Ile Leu Ser
2135              2140                2145

Ser Pro Arg Ser Gly Ser Thr Leu Leu Arg Val Met Leu Ala Gly
2150              2155                2160

His Pro Gly Leu Tyr Ser Pro Pro Glu Leu His Leu Leu Pro Phe
2165              2170                2175

Glu Thr Met Gly Asp Arg His Gln Glu Leu Gly Leu Ser His Leu
2180              2185                2190

Gly Glu Gly Leu Gln Arg Ala Leu Met Asp Leu Glu Asn Leu Thr
2195              2200                2205

Pro Glu Ala Ser Gln Ala Lys Val Asn Gln Trp Val Lys Ala Asn
2210              2215                2220

Thr Pro Ile Ala Asp Ile Tyr Ala Tyr Leu Gln Arg Gln Ala Glu
2225              2230                2235

Gln Arg Leu Leu Ile Asp Lys Ser Pro Ser Tyr Gly Ser Asp Arg
2240              2245                2250

His Ile Leu Asp His Ser Glu Ile Leu Phe Asp Gln Ala Lys Tyr
2255              2260                2265

Ile His Leu Val Arg His Pro Tyr Ala Val Ile Glu Ser Phe Thr
2270              2275                2280

Arg Leu Arg Met Asp Lys Leu Leu Gly Ala Glu Gln Gln Asn Pro
2285              2290                2295

Tyr Ala Leu Ala Glu Ser Ile Trp Arg Thr Ser Asn Arg Asn Ile
2300              2305                2310

Leu Asp Leu Gly Arg Thr Val Gly Ala Asp Arg Tyr Leu Gln Val
2315              2320                2325

Ile Tyr Glu Asp Leu Val Arg Asp Pro Arg Lys Val Leu Thr Asn
2330              2335                2340

Ile Cys Asp Phe Leu Gly Val Asp Phe Asp Glu Ala Leu Leu Asn
2345              2350                2355

Pro Tyr Ser Gly Asp Arg Leu Thr Asp Gly Leu His Gln Gln Ser
2360              2365                2370

Met Gly Val Gly Asp Pro Asn Phe Leu Gln His Lys Thr Ile Asp 2375                2380                2385

Pro Ala Leu Ala Asp Lys Trp Arg Ser Ile Thr Leu Pro Ala Ala
        2390                2395                2400

Leu Gln Leu Asp Thr Ile Gln Leu Ala Glu Thr Phe Ala Tyr Asp
    2405                2410                2415

Leu Pro Gln Glu Pro Gln Leu Thr Pro Gln Thr Gln Ser Leu Pro
2420                2425                2430

Ser Met Val Glu Arg Phe Val Thr Val Arg Gly Leu Glu Thr Cys
    2435                2440                2445

Leu Cys Glu Trp Gly Asp Arg His Gln Pro Leu Val Leu Leu Leu
2450                2455                2460

His Gly Ile Leu Glu Gln Gly Ala Ser Trp Gln Leu Ile Ala Pro
    2465                2470                2475

Gln Leu Ala Ala Gln Gly Tyr Trp Val Val Ala Pro Asp Leu Arg
    2480                2485                2490

Gly His Gly Lys Ser Ala His Ala Gln Ser Tyr Ser Met Leu Asp
2495                2500                2505

Phe Leu Ala Asp Val Asp Ala Leu Ala Lys Gln Leu Gly Asp Arg
    2510                2515                2520

Pro Phe Thr Leu Val Gly His Ser Met Gly Ser Ile Ile Gly Ala
    2525                2530                2535

Met Tyr Ala Gly Ile Arg Gln Thr Gln Val Glu Lys Leu Ile Leu
    2540                2545                2550

Val Glu Thr Ile Val Pro Asn Asp Ile Asp Ala Glu Thr Gly
2555                2560                2565

Asn His Leu Thr Thr His Leu Asp Tyr Leu Ala Ala Pro Pro Gln
    2570                2575                2580

His Pro Ile Phe Pro Ser Leu Glu Val Ala Ala Arg Arg Leu Arg
    2585                2590                2595

Gln Ala Thr Pro Gln Leu Pro Lys Asp Leu Ser Ala Phe Leu Thr
    2600                2605                2610

Gln Arg Ser Thr Lys Ser Val Glu Lys Gly Val Gln Trp Arg Trp
    2615                2620                2625

Asp Ala Phe Leu Arg Thr Arg Ala Gly Ile Glu Phe Asn Gly Ile
    2630                2635                2640

Ser Arg Arg Arg Tyr Leu Ala Leu Leu Lys Asp Ile Gln Ala Pro
    2645                2650                2655

Ile Thr Leu Ile Tyr Gly Asp Gln Ser Glu Phe Asn Arg Pro Ala
    2660                2665                2670

Asp Leu Gln Ala Ile Gln Ala Ala Leu Pro Gln Ala Gln Arg Leu
    2675                2680                2685

Thr Val Ala Gly Gly His Asn Leu His Phe Glu Asn Pro Gln Ala
    2690                2695                2700

Ile Ala Gln Ile Val Tyr Gln Gln Leu Gln Thr Pro Val Pro Lys
    2705                2710                2715

Thr Gln
    2720

<210> SEQ ID NO 3
<211> LENGTH: 900
<212> TYPE: DNA
<213> ORGANISM: Synechococcus sp.

<400> SEQUENCE: 3

```
atgaccatta cttcccccgc tcatccccat accgattaca gctggcaatg gcacggcttc    60
aatattaact atcgtcagtg gggcacccag gggctgcccg ttcttttcgt ccatggcttt   120
ggggcctcgg ccggtcattg gcgcaaaaat cttccggttt taggggaaca ttaccgctgc   180
tatgccatcg acttactggg ctttgggaaa tcggcaaaac cccaaccgga ggttgaagcg   240
gactacactt ttgaaacttg gccacccag attaaggcgt tctgtgctga atcattggt    300 gaaccggctt ttctagttgg taattccatt ggttgtgtcg ttgtcatgca ggcggctgtg   360
tcctatcccc actgggtgcg gggggttgtg cactcaatt tttccctgcg gctgttccat    420
gagcgcaatc ttttaaaagc accttttat caacgctggg gcgttcccct cttccaaaaa    480
ctcttgaccc aaaccccct cggttccttg ttctttaagc aattggccca gccgaaaaca    540
atccgcaaaa ttttagccca ggcctaccga gacaaaacag cgattaccga tgagttggtg   600
gagctgatcc tgaccccgc ccaggaccca ggggcggcag cggttttcct ggcctttacg    660
agttattccc aggggccact cccggacgac ctgctgcccc agttgcattg ccccacggca   720
gttttgtggg gaacagcgga tccgtgggaa ccagttgatc tgggccgtgc ccttgtcgcc   780
caatatcctc agattgagtt tattccctc gataatgtcg gccattgtcc ccaggatgaa    840
gctccggcat tagtcaacgg ctatttactc gattggttag ggcgacaaca gtcagcgtag   900
```

<210> SEQ ID NO 4
<211> LENGTH: 299
<212> TYPE: PRT
<213> ORGANISM: Synechococcus sp.

<400> SEQUENCE: 4

```
Met Thr Ile Thr Ser Pro Ala His Pro His Thr Asp Tyr Ser Trp Gln
1               5                   10                  15

Trp His Gly Phe Asn Ile Asn Tyr Arg Gln Trp Gly Thr Gln Gly Leu
            20                  25                  30

Pro Val Leu Phe Val His Gly Phe Gly Ala Ser Ala Gly His Trp Arg
        35                  40                  45

Lys Asn Leu Pro Val Leu Gly Glu His Tyr Arg Cys Tyr Ala Ile Asp
    50                  55                  60

Leu Leu Gly Phe Gly Lys Ser Ala Lys Pro Gln Pro Glu Val Glu Ala
65                  70                  75                  80

Asp Tyr Thr Phe Glu Thr Trp Ala Thr Gln Ile Lys Ala Phe Cys Ala
                85                  90                  95

Glu Ile Ile Gly Glu Pro Ala Phe Leu Val Gly Asn Ser Ile Gly Cys
            100                 105                 110

Val Val Met Gln Ala Ala Val Ser Tyr Pro His Trp Val Arg Gly
        115                 120                 125

Val Val Ala Leu Asn Phe Ser Leu Arg Leu Phe His Glu Arg Asn Leu
    130                 135                 140

Leu Lys Ala Pro Phe Tyr Gln Arg Trp Gly Val Pro Leu Phe Gln Lys
145                 150                 155                 160

Leu Leu Thr Gln Thr Pro Leu Gly Ser Leu Phe Phe Lys Gln Leu Ala
                165                 170                 175

Gln Pro Lys Thr Ile Arg Lys Ile Leu Ala Gln Ala Tyr Arg Asp Lys
            180                 185                 190

Thr Ala Ile Thr Asp Glu Leu Val Glu Leu Ile Leu Thr Pro Ala Gln
        195                 200                 205

Asp Pro Gly Ala Ala Ala Val Phe Leu Ala Phe Thr Ser Tyr Ser Gln
    210                 215                 220
```

```
Gly Pro Leu Pro Asp Asp Leu Leu Pro Gln Leu His Cys Pro Thr Ala
225                 230                 235                 240

Val Leu Trp Gly Thr Ala Asp Pro Trp Glu Pro Val Asp Leu Gly Arg
            245                 250                 255

Ala Leu Val Ala Gln Tyr Pro Gln Ile Glu Phe Ile Pro Leu Asp Asn
        260                 265                 270

Val Gly His Cys Pro Gln Asp Glu Ala Pro Ala Leu Val Asn Gly Tyr
    275                 280                 285

Leu Leu Asp Trp Leu Gly Arg Gln Gln Ser Ala
    290                 295
```

<210> SEQ ID NO 5
<211> LENGTH: 4891
<212> TYPE: DNA
<213> ORGANISM: Artificial Sequence
<220> FEATURE:
<223> OTHER INFORMATION: Description of Artificial Sequence: Synthetic pJB844 polynucleotide

<400> SEQUENCE: 5

| | | |
|---|---|---|
| ttagaaaaac tcatcgagca tcaaatgaaa ctgcaattta ttcatatcag gattatcaat | 60 |
| accatatttt tgaaaagcc gtttctgtaa tgaaggagaa aactcaccga ggcagttcca | 120 |
| taggatggca agatcctggt atcggtctgc gattccgact cgtccaacat caatacaacc | 180 |
| tattaatttc ccctcgtcaa aaataaggtt atcaagtgag aaatcaccat gagtgacgac | 240 |
| tgaatccggt gagaatggca aaagtttatg catttctttc cagacttgtt caacaggcca | 300 |
| gccattacgc tcgtcatcaa atcactcgc atcaaccaaa ccgttattca ttcgtgattg | 360 |
| cgcctgagcg aggcgaaata cgcgatcgct gttaaaagga caattacaaa caggaatcga | 420 |
| gtgcaaccgg cgcaggaaca ctgccagcgc atcaacaata ttttcacctg aatcaggata | 480 |
| ttcttctaat acctggaacg ctgttttttcc ggggatcgca gtggtgagta accatgcatc | 540 |
| atcaggagta cggataaaat gcttgatggt cggaagtggc ataaattccg tcagccagtt | 600 |
| tagtctgacc atctcatctg taacatcatt ggcaacgcta cctttgccat gtttcagaaa | 660 |
| caactctggc gcatcgggct tcccatacaa gcgatagatt gtcgcacctg attgcccgac | 720 |
| attatcgcga gcccatttat acccatataa atcagcatcc atgttggaat ttaatcgcgg | 780 |
| cctcgacgtt tcccgttgaa tatggctcat attcttcctt tttcaatatt attgaagcat | 840 |
| ttatcagggt tattgtctca tgagcggata catatttgaa tgtatttaga aaaataaaca | 900 |
| aatagggtc agtgttacaa ccaattaacc aattctgaac attatcgcga gcccatttat | 960 |
| acctgaatat ggctcataac accccttgtt tgcctggcgg cagtagcgcg gtggtcccac | 1020 |
| ctgaccccat gccgaactca gaagtgaaac gccgtagcgc cgatggtagt gtgggactc | 1080 |
| cccatgcgag agtagggaac tgccaggcat caaataaaac gaaaggctca gtcgaaagac | 1140 |
| tgggcctttc gccgggcta attagggggt gtcgccttc tgaagtgggg cctgcaggtt | 1200 |
| attgaggtat cgcgagatgg ctcccacatt cggggaaata gacatttcat tgtcattgag | 1260 |
| aaccaccatt aaattcgtat cgggtaaatg acccgcatgg ttgatggctt cgagggccat | 1320 |
| gccgccggtc aaggcaccat caccaatgac tgccacacat ttaaactctt ctcccttggc | 1380 |
| atcccgtgcc aatgccatcc ctagcgctgc ggaaatactg gtcgaggcat ggccagcacc | 1440 |
| aaaatgatca aacacatttt cactgcgctt aaggtagcca gctacccat cctttttgccg | 1500 |
| gagggtgtgg aattcgttgt agcgtccggt aatcaattta tggggataag cctgatgacc | 1560 |

```
gacatcccac accaccttgt cgcgatcgag atcaagggtt tggtagaggg cgagggttag    1620
ttcaaccacc cctaaaccag ggccgaggtg gccaccactt gcggcaatcg tctggaggtg    1680
tttttcgcga atttgccggg caatctcttc caactgacgg acggtcaagc cgtggagttg    1740
gttcggatgg gtaatttcac tcaggtgcat gggtgtttct agagagcgat cttataaagg    1800
ggtctagttc tcaggatatc aggtctaaca attttaatca gaagatcccg gttagtccgg    1860
atgatcccat ggggttgtgt gggaatcttg gtcaaggttc cacagatgtt taggatctaa    1920
tatttacggg ttttcggact gcactttgca atattttgcg gccgctcata tgtaacagga    1980
attcggttac tagttttaa ttaacgaatc catgtgggag tttattcttg acacagatat    2040
ttatgatata ataactgagt aagcttaaca taaggaggaa aaactaatgt tacgcagcag    2100
caacgatgtt acgcagcagg gcagtcgccc taaaacaaag ttaggtggct caagtatggg    2160
catcattcgc acatgtaggc tcggccctga ccaagtcaaa tccatgcggg ctgctcttga    2220
tcttttcggt cgtgagttcg gagacgtagc cacctactcc caacatcagc cggactccga    2280
ttacctcggg aacttgctcc gtagtaagac attcatcgcg cttgctgcct tcgaccaaga    2340
agcggttgtt ggcgctctcg cggcttacgt tctgcccaag tttgagcagc cgcgtagtga    2400
gatctatatc tatgatctcg cagtctccgg cgagcaccgg aggcagggca ttgccaccgc    2460
gctcatcaat ctcctcaagc atgaggccaa cgcgcttggt gcttatgtga tctacgtgca    2520
agcagattac ggtgacgatc ccgcagtggc tctctataca aagttgggca tacgggaaga    2580
agtgatgcac tttgatatcg acccaagtac cgccacctag gcgcgccgta tgccttagca    2640
actcctgtga atggaaattc tggactccgt atcctagcaa ttttacgaa tacccacggg    2700
ctatagccta gttaaccata ttaaaccgtg agttccctcc ccacggtaaa tcctcccaaa    2760
atccgccgtt ccttcgatta tggagggcct ggtttcaact gatttgagtg taaaagccct    2820
aggctacgct gactgttgtc gccctaacca atcgagtaaa tagccgttga ctaatgccgg    2880
agcttcatcc tggggacaat ggccgacatt atcgagggga ataaactcaa tctgaggata    2940
ttgggcgaca agggcacggc ccagatcaac tggttcccac ggatccgctg ttccccacaa    3000
aactgccgtg gggcaatgca actggggcag caggtcgtcc gggagtggcc cctgggaata    3060
actcgtaaag gccaggaaaa ccgctgccgc ccctgggtcc tgggcggggg tcaggatcag    3120
ctccaccaac tcatcggtaa tcgctgtttt gtctcggtag gcctgggcta aaattttgcg    3180
gattgttttc ggctgggcca attgcttaaa gaacaaggaa ccgagggggg tttgggtcaa    3240
gagtttttgg aagaggggaa cgccccagcg ttgataaaaa ggtgcttta aaagattgcg    3300
ctcatggaac agccgcaggg aaaaattgag tgccacaacc ccccgcaccc agtggggata    3360
ggacacagcc gcctgcatga caacgacaca accaatggaa ttaccaacta gaaaagccgg    3420
ttcggccggc caacgtcaaa agggcgacac aaaatttatt ctaaatgcat aataaatact    3480
gataacatct tatagtttgt attatatttt gtattatcgt tgacatgtat aattttgata    3540
tcaaaaactg attttccctt tattattttc gagatttatt ttcttaattc tctttaacaa    3600
actagaaata ttgtatatac aaaaaatcat aaataataga tgaatagttt aattataggt    3660
gttcatcaat cgaaaagca acgtatctta tttaaagtgc gttgcttttt tctcatttat    3720
aaggttaaat aattctcata tatcaagcaa agtgacaggc gcccttaaat attctgacaa    3780
atgctctttc cctaaactcc ccccataaaa aaacccgccg aagcgggttt ttacgttatt    3840
tgcggattaa cgattactcg ttatcagaac cgcccagggg gccgagcttt aagactggcc    3900
gtcgttttac aacacagaaa gagtttgtag aaacgcaaaa aggccatccg tcaggggcct    3960
```

```
tctgcttagt ttgatgcctg gcagttccct actctcgcct tccgcttcct cgctcactga    4020
ctcgctgcgc tcggtcgttc ggctgcggcg agcggtatca gctcactcaa aggcggtaat    4080
acggttatcc acagaatcag gggataacgc aggaaagaac atgtgagcaa aaggccagca    4140
aaaggccagg aaccgtaaaa aggccgcgtt gctggcgttt ttccataggc tccgcccccc    4200
tgacgagcat cacaaaaatc gacgctcaag tcagaggtgg cgaaacccga caggactata    4260
aagataccag gcgtttcccc ctggaagctc cctcgtgcgc tctcctgttc cgaccctgcc    4320
gcttaccgga tacctgtccg cctttctccc ttcgggaagc gtggcgcttt ctcatagctc    4380
acgctgtagg tatctcagtt cggtgtaggt cgttcgctcc aagctgggct gtgtgcacga    4440
accccccgtt cagcccgacc gctgcgcctt atccggtaac tatcgtcttg agtccaaccc    4500
ggtaagacac gacttatcgc cactggcagc agccactggt aacaggatta gcagagcgag    4560
gtatgtaggc ggtgctacag agttcttgaa gtggtgggct aactacggct acactagaag    4620
aacagtattt ggtatctgcg ctctgctgaa gccagttacc ttcggaaaaa gagttggtag    4680
ctcttgatcc ggcaaacaaa ccaccgctgg tagcggtggt ttttttgttt gcaagcagca    4740
gattacgcgc agaaaaaaag gatctcaaga agatcctttg atcttttcta cggggtctga    4800
cgctcagtgg aacgacgcgc gcgtaactca cgttaaggga ttttggtcat gagcttgcgc    4860
cgtcccgtca gtcagcgta atgctctgct t                                    4891

<210> SEQ ID NO 6
<211> LENGTH: 4836
<212> TYPE: DNA
<213> ORGANISM: Artificial Sequence
<220> FEATURE:
<223> OTHER INFORMATION: Description of Artificial Sequence: Synthetic
      pJB845 polynucleotide

<400> SEQUENCE: 6
ttagaaaaac tcatcgagca tcaaatgaaa ctgcaattta ttcatatcag gattatcaat      60
accatatttt tgaaaaagcc gtttctgtaa tgaaggagaa aactcaccga ggcagttcca     120
taggatggca agatcctggt atcggtctgc gattccgact cgtccaacat caatacaacc     180
tattaatttc ccctcgtcaa aaataaggtt atcaagtgag aaatcaccat gagtgacgac     240
tgaatccggt gagaatggca aaagtttatg catttctttc cagacttgtt caacaggcca     300
gccattacgc tcgtcatcaa aatcactcgc atcaaccaaa ccgttattca ttcgtgattg     360
cgcctgagcg aggcgaaata cgcgatcgct gttaaaagga cattacaaa caggaatcga     420 gtgcaaccgg cgcaggaaca ctgccagcgc atcaacaata ttttcacctg aatcaggata     480
ttcttctaat acctggaacg ctgtttttcc gggatcgca gtggtgagta accatgcatc     540
atcaggagta cggataaaat gcttgatggt cggaagtggc ataaattccg tcagccagtt     600
tagtctgacc atctcatctg taacatcatt ggcaacgcta cctttgccat gtttcagaaa     660
caactctggc gcatcgggct tcccatacaa gcgatagatt gtcgcacctg attgcccgac     720
attatcgcga gcccatttat acccatataa atcagcatcc atgttggaat ttaatcgcgg     780
cctcgacgtt tcccgttgaa tatggctcat attcttcctt tttcaatatt attgaagcat     840
ttatcagggt tattgtctca tgagcggata catatttgaa tgtatttaga aaaataaaca     900
aataggggtc agtgttacaa ccaattaacc aattctgaac attatcgcga gcccatttat     960
acctgaatat ggctcataac acccccttgtt tgcctggcgg cagtagcgcg gtggtcccac    1020
ctgaccccat gccgaactca gaagtgaaac gccgtagcgc cgatggtagt gtggggactc    1080
```

```
cccatgcgag agtagggaac tgccaggcat caaataaaac gaaaggctca gtcgaaagac    1140
tgggcctttc gcccgggcta attaggggagt gtcgcccttc tgaagtgggg cctgcaggat    1200
tgtggtggga aaccatcact cctttaggat cgcccgtgga gccactggtg tattgcaaaa    1260
aagcgagatc tgtgccggaa atgttcggtt tttgccaatt ttttcctgaa attaattcaa    1320
cttgatctgt agccaaacaa tgaaaatccg taccttctaa agcttcgagg cgatcggcaa    1380
ttttatcttt aagttctgtt gtggtgaggg caaattttgc ctgggcatct tggataatgc    1440
tatggaggcg gtcaaaggat ttattcggcc gtggtgggta agctggcacc gcaacaacac    1500
cagcatacaa acatcccaaa aaggcaccga taaactctaa acccggtgga taaagtaata    1560
atgcccgttg cccttgagcc tggttagctt gcaaaaaagc ggcgatcgcc tgggcttttt    1620
ggtctaattc tccgtaggtc agggccgcag attccgcttc gccatcagcc agaaaactaa    1680
acacggtttt ccgcgcctga agtttagctc tgtactggag cagatcgacg aaatttgcaa    1740
attgaccaac catgtatgcc ttagcaactc ctgtgaatgg aaattctgga ctccgtatcc    1800
tagcaatttt tacgaatacc cacgggctat agcctagtta accatattaa accgtgagtt    1860
ccctccccac ggtaaatcct cccaaaatcc gccgttcctt cgattatgga gggcctggtt    1920
tcaactgatt tgagtgtaaa agccctaggg cggccgctca tatgtaacag gaattcggtt    1980
actagttttt aattaacgaa tccatgtggg agtttattct tgacacagat atttatgata    2040
taataactga gtaagcttaa cataaggagg aaaaactaat gttacgcagc agcaacgatg    2100
ttacgcagca gggcagtcgc cctaaaacaa agttaggtgg ctcaagtatg gcatcattc    2160 gcacatgtag gctcggccct gaccaagtca aatccatgcg ggctgctctt gatcttttcg    2220
gtcgtgagtt cggagacgta gccacctact cccaacatca gccggactcc gattacctcg    2280
ggaacttgct ccgtagtaag acattcatcg cgcttgctgc cttcgaccaa gaagcggttg    2340
ttggcgctct cgcggcttac gttctgccca agtttgagca gccgcgtagt gagatctata    2400
tctatgatct cgcagtctcc ggcgagcacc ggaggcaggg cattgccacc gcgctcatca    2460
atctcctcaa gcatgaggcc aacgcgcttg gtgcttatgt gatctacgtg caagcagatt    2520
acggtgacga tcccgcagtg gctctctata caaagttggg catacgggaa gaagtgatgc    2580
actttgatat cgacccaagt accgccacct aggcgcgccg gtgagcgatg gataaaaccg    2640
aaataaggaa caaatgtcct agggcgtgtt gtctaaatcg tgatggcaaa gatggggcac    2700
cggatcataa ccccccagggt gaaacgggtg acagcggcca aggcgcttta gggcgagcca    2760 actgccccg agtacaccaa agcgttccac ggcttcgagg gcatattggg aacaggtggg    2820
ctgaaagcga caactggggg ggaatagggg ggaaatccag cgacggtagc ctttgatgct    2880
ccagaggatt aagcttttca tggtatttag gcaacgaag cagtcttttg gaggtcgatg    2940
gtttgaccaa gggcttcgtt gacgagacga ctaaagtctt cgccttcgat ggtttcttct    3000
tcgatgagac gatccaccag acgatctaca agttgacgat tgtcccgaat aatttgcttg    3060
gcagtttcgt agcactcgtt gataatttcg cgcaccttga ggtcaatgcg ctgggcgatc    3120
gcctcggaat attcaggccg ctcccccaaac caatcatttc tgaggaaaac ttcaccccga    3180
ttggtttcta gggcaaagtg acccagttct gacatcccaa attttgtcac catttgacgg    3240
gcaatgttcg tgagcatttg gatatcctgg gaggcccag aagtgatttc atcgtagcca    3300
aagacaatat cctcggcggc gcgtccccc agggccacgg cgatttgggc gcggaattgg    3360
gctttggtgg ccggccaacg tcaaaagggc gacacaaaat ttattctaaa tgcataataa    3420
```

```
atactgataa catcttatag tttgtattat attttgtatt atcgttgaca tgtataattt    3480
tgatatcaaa aactgatttt ccctttatta ttttcgagat ttattttctt aattctcttt    3540
aacaaactag aaatattgta tatacaaaaa atcataaata atagatgaat agtttaatta    3600
taggtgttca tcaatcgaaa aagcaacgta tcttatttaa agtgcgttgc ttttttctca    3660
tttataaggt taaataattc tcatatatca agcaaagtga caggcgccct taaatattct    3720
gacaaatgct ctttccctaa actccccca taaaaaaacc cgccgaagcg gttttttacg    3780
ttatttgcgg attaacgatt actcgttatc agaaccgccc aggggcccg agcttaagac    3840 tggccgtcgt tttacaacac agaaagagtt tgtagaaacg caaaaaggcc atccgtcagg    3900
ggccttctgc ttagtttgat gcctggcagt tccctactct cgccttccgc ttcctcgctc    3960
actgactcgc tgcgctcggt cgttcggctg cggcgagcgg tatcagctca ctcaaaggcg    4020
gtaatacggt tatccacaga atcaggggat aacgcaggaa agaacatgtg agcaaaaggc    4080
cagcaaaagg ccaggaaccg taaaaaggcc gcgttgctgg cgttttcca taggctccgc    4140 cccctgacg agcatcacaa aaatcgacgc tcaagtcaga ggtggcgaaa cccgacagga    4200
ctataaagat accaggcgtt tcccctgga agctccctcg tgcgctctcc tgttccgacc    4260
ctgccgctta ccggatacct gtccgccttt ctcccttcgg gaagcgtggc gctttctcat    4320
agctcacgct gtaggtatct cagttcggtg taggtcgttc gctccaagct gggctgtgtg    4380
cacgaacccc ccgttcagcc cgaccgctgc gccttatccg gtaactatcg tcttgagtcc    4440
aacccggtaa gacacgactt atcgccactg gcagcagcca ctggtaacag gattagcaga    4500
gcgaggtatg taggcggtgc tacagagttc ttgaagtggt gggctaacta cggctacact    4560
agaagaacag tatttggtat ctgcgctctg ctgaagccag ttaccttcgg aaaaagagtt    4620
ggtagctctt gatccggcaa acaaaccacc gctggtagcg gtggtttttt tgtttgcaag    4680
cagcagatta cgcgcagaaa aaaggatct caagaagatc ctttgatctt ttctacgggg    4740
tctgacgctc agtggaacga cgcgcgcgta actcacgtta agggattttg gtcatgagct    4800
tgcgccgtcc cgtcaagtca gcgtaatgct ctgctt                              4836
```

<210> SEQ ID NO 7
<211> LENGTH: 4998
<212> TYPE: DNA
<213> ORGANISM: Artificial Sequence
<220> FEATURE:
<223> OTHER INFORMATION: Description of Artificial Sequence: Synthetic pJB808 polynucleotide

<400> SEQUENCE: 7

```
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga atcaccatg agtgacgact     240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
```

```
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020 tgacccatg ccgaactcag aagtgaaacg ccgtagcgcc gatggtagtg tggggactcc    1080
ccatgcgaga gtagggaact gccaggcatc aaataaaacg aaaggctcag tcgaaagact   1140
gggcctttcg cccgggctaa ttaggggtg tcgcccttat tcgactctat agtgaagttc    1200
ctattctcta gaaagtatag gaacttctga agtggggaag cttaagtata ggaacttctg   1260
aagtggggcc tgcagggaaa ggctcttgag gctatcatga cagaagcatc gcagcctata   1320
aaatacgctg gaaagaaata taaatatgct gtttcgtatc atgtcctaaa tgctgctgat   1380
tttggtgttc cgcaatttag agaaagagta ttcatcgtag gtaatcgttt gggcaaaaca   1440
ttccaatttc ctgaaccaac tcatgggcct agcaaccaag cgagacagat agatcttttt   1500
ggcaagcagc taaaaccta caaaactgtt caagatgcaa ttagcactct cccccctgca    1560
acccctcctt cagcgatggc actaagagtt tcgcagacca taaaagatag gataaagaat   1620
catggatatt aaaaacgttc atatcaaaaa tcacgaacaa acagctcatg caccttccac   1680
tctagaaaaa attcgtaaag tcaaacaagg gggtaaactc tcagaacaga caaagacatt   1740
tggttcaacc taccgcaggt tagatccgaa ccagccatct cctacagtga cccgtagtgg   1800
ttatcgagat tttattcatc cttttgaaga tcgaatgctc acagttcgtg aactggcttg   1860
tttgcaaacc tttccccttg attgggagtt taccggaact cgacttgatt cttatagtag   1920
taaacgtaaa gtgacgatga ctcagtttgg acaagtgggt aatgcagtac cgccgttact   1980
tgctgaagct gttgctaaag cggttagcga acagcttctg gatgtcgcgg ccgcggtacc   2040
catatgtaac aggaattcac tagttttaa ttaacgaatc catgtgggag tttattcttg    2100
acacagatat ttatgatata ataactgagt aagcttaaca taaggaggaa aaactaatgt   2160
tacgcagcag caacgatgtt acgcagcagg gcagtcgccc taaaacaaag ttaggtggct   2220
caagtatggg catcattcgc acatgtaggc tcggccctga ccaagtcaaa tccatgcggg   2280
ctgctcttga tctttcggt cgtgagttcg gagacgtagc cacctactcc caacatcagc    2340
cggactccga ttacctcggg aacttgctcc gtagtaagac attcatcgcg cttgctgcct   2400
tcgaccaaga agcggttgtt ggcgctctcg cggcttacgt tctgcccaag tttgagcagc   2460
cgcgtagtga gatctatatc tatgatctcg cagtctccgg cgagcaccgg aggcagggca   2520
ttgccaccgc gctcatcaat ctcctcaagc atgaggccaa cgcgcttggt gcttatgtga   2580
tctacgtgca agcagattac ggtgacgatc ccgcagtggc tctctataca agttgggca    2640 tacgggaaga agtgatgcac tttgatatcg acccaagtac cgccacctag gcgcgccctt   2700
tacaaaatca aacccgatcg cctctctatt ttgataaatc tatgtctact ccctctgtta   2760
cccctgtaga atctagcacc ctaatcaaaa ccctgaact gctggctccg gcgggaaatt    2820
gggactgtgc gatcaccgcc gtggagaatg gggctgatgc gatttatttt ggctggata    2880 aatttaatgc ccggatgcga tcacaaaact ttgtcgagtc agatttgccg gagttgatgg    2940
catacttaca tcggcgcggc gtgaagggct atgtgacgtt aaatacgctg attttcacct   3000
```

```
cggaattggc ggcagtcgaa caatatttgc ggtcgattat tgcggcggga gtcgatgcgg    3060
cgatcgtcca ggatgtgggg ctgtgccaat taatttggca attgtcgccc gattttccga    3120
tccatggttc gacgcaaatg accgtcacca gcgccgcagg ggtcgagttc gcgcaaaact    3180
tgggttgtga tttggtggta ttggcgcggg aatgttcgat caaggaaatc aataaaatcc    3240
agcaggaatt gggtcaacaa aagatctcaa tgccgctaga agtgtttgtc cacggggcgt    3300
tgtgcgtcgc ctattctggg caatgtttaa ccagtgaatc cctcggcgga cggtcggcca    3360
atcgcggaga atgcgcccaa gcctgccgga tgccctacga aatgattgtc gatggtaggc    3420
catttgatct gagcgacaga cgttaccggc cggccaaaat gaagtgaagt tcctatactt    3480
aagcttaaaa tgaagtgaag ttcctatact ttctagagaa taggaacttc tatagtgagt    3540
cgaataaggg cgacacaaaa tttattctaa atgcataata aatactgata acatcttata    3600
gtttgtatta tattttgtat tatcgttgac atgtataatt ttgatatcaa aaactgattt    3660 tcccttatt attttcgaga tttattttct taattctctt taacaaacta gaaatattgt     3720
atatacaaaa aatcataaat aatagatgaa tagtttaatt ataggtgttc atcaatcgaa    3780
aaagcaacgt atcttattta aagtgcgttg cttttttctc atttataagg ttaaataatt    3840
ctcatatatc aagcaaagtg acaggcgccc ttaaatattc tgacaaatgc tctttcccta    3900
aactcccccc ataaaaaaac ccgccgaagc gggtttttac gttatttgcg gattaacgat    3960
tactcgttat cagaaccgcc caggggccc gagcttaaga ctggccgtcg ttttacaaca     4020
cagaaagagt ttgtagaaac gcaaaaaggc catccgtcag gggccttctg cttagtttga    4080
tgcctggcag ttccctactc tcgccttccg cttcctcgct cactgactcg ctgcgctcgg    4140
tcgttcggct gcggcgagcg gtatcagctc actcaaaggc ggtaatacgg ttatccacag    4200
aatcagggga taacgcagga agaacatgt gagcaaaagg ccagcaaaag gccaggaacc     4260
gtaaaaaggc cgcgttgctg gcgttttttcc ataggctccg cccccctgac gagcatcaca    4320
aaaatcgacg ctcaagtcag aggtggcgaa acccgacagg actataaaga taccaggcgt    4380
ttccccctgg aagctccctc gtgcgctctc ctgttccgac cctgccgctt accggatacc    4440
tgtccgcctt tctcccttcg ggaagcgtgg cgctttctca tagctcacgc tgtaggtatc    4500
tcagttcggt gtaggtcgtt cgctccaagc tgggctgtgt gcacgaaccc cccgttcagc    4560
ccgaccgctg cgccttatcc ggtaactatc gtcttgagtc caacccggta agacacgact    4620
tatcgccact ggcagcagcc actggtaaca ggattagcag agcgaggtat gtaggcggtg    4680
ctacagagtt cttgaagtgg tgggctaact acggctacac tagaagaaca gtatttggta    4740
tctgcgctct gctgaagcca gttaccttcg gaaaagagt tggtagctct tgatccggca     4800
aacaaaccac cgctggtagc ggtggttttt tgtttgcaa gcagcagatt acgcgcagaa      4860
aaaaaggatc tcaagaagat cctttgatct tttctacggg gtctgacgct cagtggaacg    4920
acgcgcgcgt aactcacgtt aagggatttt ggtcatgagc ttgcgccgtc ccgtcaagtc    4980
agcgtaatgc tctgcttt                                                  4998
```

<210> SEQ ID NO 8
<211> LENGTH: 2762
<212> TYPE: PRT
<213> ORGANISM: Cyanothece sp.

<400> SEQUENCE: 8

Met Lys Arg Asn Phe Ser Asn Phe Val Asp Leu Leu Asn His Arg Ala
1               5                   10                  15

```
Glu Thr Gln Ser Asp Lys Ile Leu Phe Thr Phe Leu Gly Asp Gly Glu
             20                  25                  30

Thr Glu Ser Leu Ser Leu Thr Tyr Gln Gln Leu Asp Gln Gln Ala Arg
         35                  40                  45

Ala Ile Ala Val Gln Leu Gln Ser Leu Asn Ala Thr Gly Glu Arg Ala
    50                  55                  60

Leu Leu Leu Tyr Gln Pro Gly Leu Glu Phe Ile Ser Ala Phe Phe Gly
65                  70                  75                  80

Cys Leu Tyr Gly Gly Val Ile Pro Val Pro Ala Tyr Pro Pro Arg Ala
                85                  90                  95

Asn Arg Ser Ile Glu Arg Leu Gln Ala Ile Val Ser Asp Ala Glu Ala
            100                 105                 110

Lys Phe Ala Leu Thr Ser Glu Ser Leu Val Asn Ser Ile Glu Gly Lys
        115                 120                 125

Leu Thr Gln Ser Leu Ser Gln Glu Ala Ile Gln Cys Val Thr Thr Asp
130                 135                 140

Asn Leu Glu Leu Ser Leu Ser Gln Gly Trp His Lys Pro Lys Ile Asn
145                 150                 155                 160

Pro Glu Gln Leu Ala Phe Leu Gln Tyr Thr Ser Gly Ser Thr Gly Asn
                165                 170                 175

Pro Lys Gly Val Met Val Ser His Ser Asn Leu Met His Asn Ala Ala
            180                 185                 190

Leu Ile Asn His Tyr Phe Gln Asp Thr Pro Glu Ser Arg Gly Ala Ser
        195                 200                 205

Trp Leu Pro Pro Tyr His Asp Met Gly Leu Ile Gly Gly Ile Leu Gln
    210                 215                 220

Pro Ile Tyr Val Gly Val Tyr Val Val Leu Met Pro Pro Val Thr Phe
225                 230                 235                 240

Leu Gln Arg Pro Leu Arg Trp Leu Glu Val Ile Ser Arg Tyr Arg Ile
                245                 250                 255

Thr Thr Ser Gly Ala Pro Asn Phe Ala Tyr Glu Leu Cys Ala Thr Gln
            260                 265                 270

Ile Thr Pro Glu Gln Arg Glu Asn Leu Asp Leu Ser Cys Trp Glu Leu
        275                 280                 285

Ala Phe Ser Gly Ala Glu Pro Ile Arg Ala His Thr Leu Glu Gln Phe
290                 295                 300

Ala Lys Ala Phe Ala Pro Cys Gly Phe Arg Pro Glu Ala Phe Tyr Ala
305                 310                 315                 320

Cys Tyr Gly Met Ala Glu Thr Thr Leu Ile Val Thr Gly Gly Lys Arg
                325                 330                 335

Ser Glu Lys Pro Phe Leu Lys Glu Phe Asn Ser Lys Gly Ile Glu Lys
            340                 345                 350

Asn Gln Val Ile Pro Ala Ser Ser Cys Asp Gln Asp Arg Val Ser Leu
        355                 360                 365

Val Ser Cys Gly Gln Val Ala Glu Ala Gln Lys Val Ile Ile Val Asn
370                 375                 380

Pro Glu Thr Leu Asn Gln Cys Ala Asp Asp Glu Ile Gly Glu Ile Trp
385                 390                 395                 400

Val Ser Ser Glu Ser Val Ala Gln Gly Tyr Trp Asn Arg Pro Gln Leu
                405                 410                 415

Thr Glu Ala Ile Phe Lys Ala Tyr Thr Pro Asp Ser Pro Glu Arg Pro
            420                 425                 430
```

-continued

Phe Leu Arg Thr Gly Asp Leu Gly Phe Leu Gln Asp Gly Glu Leu Phe
        435                 440                 445

Val Thr Gly Arg Leu Lys Asp Leu Ile Ile Ile Arg Gly Arg Asn His
    450                 455                 460

Tyr Pro Gln Asp Ile Glu Met Thr Ala Glu Lys Ser His Pro Ala Leu
465                 470                 475                 480

Arg Glu Ser Cys Gly Ala Ala Phe Ser Val Glu Val Gly Glu Glu Glu
                485                 490                 495

Arg Leu Val Ile Thr Tyr Glu Val Lys Arg Ser Tyr Ile Arg Lys Leu
            500                 505                 510

Asn Val Glu Glu Val Thr Ser Ala Ile Arg Lys Ala Val Thr Gln Thr
        515                 520                 525

His Glu Leu Gln Pro Tyr Ala Ile Val Leu Leu Lys Thr Gly Ser Ile
    530                 535                 540

Pro Lys Thr Ser Ser Gly Lys Ile Gln Arg His Ala Cys Lys Ala Glu
545                 550                 555                 560

Phe Leu Glu Gly Ser Leu Asn Ser Val Gly Gln Trp Ser Val Thr Gln
                565                 570                 575

Leu Ser Glu Ala Ser Ser Gln Gln Ser Lys Pro Lys Pro Arg Lys Asn
            580                 585                 590

Leu Lys Gln His Ser Pro Ser Asn Ser Gln Gln Leu Ile Gln Asp
        595                 600                 605

Trp Leu Val Asp Lys Ile Ala Gln Arg Leu Ser Ile Ser Ser Ala Glu
    610                 615                 620

Ile Glu Ile Thr Glu Pro Phe Ala Ser Tyr Gly Leu Asp Ser Val Gln
625                 630                 635                 640

Ala Val Arg Ile Thr Ala Glu Leu Glu Asp Trp Leu Lys Val Lys Leu
                645                 650                 655

Ser Pro Thr Leu Ala Tyr Asp Tyr Pro Ser Ile Glu Ser Leu Ala Gln
            660                 665                 670

Tyr Leu Thr Ala Leu Leu Lys Gly Gln Glu Ile Pro Ser Thr Pro Val
        675                 680                 685

Leu Lys Thr Val Thr Gln Gln Thr Lys Ser Glu Leu Ile Ala Ile
    690                 695                 700

Ile Gly Met Gly Cys Arg Phe Pro Gly Ala Asn Asn Pro Asp Gln Phe
705                 710                 715                 720

Trp Gln Leu Leu Gln Gln Gly Lys Asp Gln Ile Thr Gln Val Lys Gly
                725                 730                 735

Arg Trp Glu Lys Glu Thr Trp Gly Gly Phe Leu Asp His Ile Asp Gln
            740                 745                 750

Phe Asp Pro Gln Phe Phe Gly Ile Ser Arg Arg Glu Ala Gln Glu Ile
        755                 760                 765

Asp Pro Gln Gln Arg Leu Leu Leu Glu Val Ser Trp Glu Ala Leu Glu
    770                 775                 780

Asn Ala Ser Ile Ala Val Asp Gln Leu Ala Gly Ser Gln Thr Gly Val
785                 790                 795                 800

Phe Ile Gly Ile Ser Ser Ser Asp Tyr Ser Gln Ile Arg Leu Lys Ser
                805                 810                 815

Gln Leu Asp Pro Ser Ala Tyr Ala Gly Thr Gly Asn Ala His Ser Ile
            820                 825                 830

Ala Ala Asn Arg Leu Ser Tyr Phe Tyr Asp Phe Arg Gly Pro Ser Leu
        835                 840                 845

Thr Val Asp Thr Ala Cys Ser Ser Ser Leu Val Ala Val His Leu Ala

-continued

```
            850                 855                 860
Ile Ser Ser Leu Gln Arg Gly Glu Cys Gln Met Ala Ile Ala Gly Gly
865                 870                 875                 880

Val Asn Leu Leu Leu Ser Pro Glu Leu Thr Glu Thr Phe Thr Gln Ala
                885                 890                 895

Gly Met Met Ala Thr Asp Gly Arg Cys Lys Thr Phe Asp Glu Gly Ala
            900                 905                 910

Asp Gly Tyr Val Arg Gly Glu Gly Cys Gly Val Val Ile Leu Lys Ser
        915                 920                 925

Leu Glu Asn Ala Ile Ala Asp Gly Asp Pro Ile Leu Gly Val Ile His
    930                 935                 940

Gly Ser Ala Ile Asn Gln Asp Gly Arg Ser Asn Gly Leu Thr Ala Pro
945                 950                 955                 960

Asn Gly Ile Ala Gln Lys Gln Val Ile Cys Gln Ala Leu Ile Asn Gly
                965                 970                 975

Asn Ile Gln Ala Ala Asp Ile Ser Tyr Ile Glu Thr His Gly Thr Gly
            980                 985                 990

Thr Pro Leu Gly Asp Pro Ile Glu Val Asn Ala Leu Lys Ser Val Leu
        995                 1000                1005

Met Glu Gly Arg Ser Leu Asp Gln Pro Leu Trp Ile Gly Ser Leu
    1010                1015                1020

Lys Thr Asn Ile Gly His Leu Glu Ala Ala Ala Gly Ile Ala Gly
    1025                1030                1035

Leu Ile Lys Val Ile Leu Ser Leu Lys His Gln Gln Ile Pro Pro
    1040                1045                1050

His Leu His Leu Asn Ser Leu Asn Pro His Ile Asn Leu Asn Glu
    1055                1060                1065

Thr Pro Ile Ala Ile Pro Thr Gln Leu Thr Pro Trp Lys Ile Asp
    1070                1075                1080

Ser Lys Pro Arg Leu Ala Gly Val Ser Ser Phe Gly Phe Gly Gly
    1085                1090                1095

Thr Asn Ala His Val Ile Val Gly Glu Tyr Asn Ser Leu Ser Pro
    1100                1105                1110

Ser Pro Glu Asn Leu Ser Pro Tyr Pro Ser Pro Thr Arg Arg Glu
    1115                1120                1125

Glu Leu Lys Pro Val Glu Arg Pro Leu His Ile Leu Thr Leu Ser
    1130                1135                1140

Ala Lys Arg Glu Lys Asp Leu Ser Ala Leu Ile Asp Ser Tyr Lys
    1145                1150                1155

Ser Tyr Leu Thr Ser Gln Pro Thr Ala Ser Leu Glu Asp Ile Cys
    1160                1165                1170

Phe Thr Ala Asn Val Gly Arg Ser Pro Leu Lys His Arg Val Ala
    1175                1180                1185

Ile Ile Ala Asn Ser Gln Asp Gln Leu Arg Glu Lys Leu Gly Lys
    1190                1195                1200

Gly Glu Val Ile Lys Ala Glu Asn Ser Ala Gln Leu Thr Pro Lys
    1205                1210                1215

Ile Ala Phe Leu Phe Thr Gly Gln Gly Ser Gln Tyr Val Gly Met
    1220                1225                1230

Gly Tyr Gln Leu Tyr Gln Thr Gln Pro Thr Phe Lys Thr Ala Leu
    1235                1240                1245

Asp Thr Cys Ala Asp Leu Leu Ser Pro Tyr Leu Lys Arg Pro Leu
    1250                1255                1260
```

-continued

```
Leu Glu Ile Leu Tyr Pro Gln Asp Ser Thr Ala Ile Ser Asp Glu
    1265                1270                1275
Leu Asp Gln Thr Ala Tyr Thr Gln Pro Ala Leu Phe Ala Leu Glu
    1280                1285                1290
Tyr Ala Leu Ala Gln Leu Trp Leu Ser Trp Gly Ile Glu Pro Ser
    1295                1300                1305
Ile Val Met Gly His Ser Val Gly Glu Tyr Val Ala Ala Thr Leu
    1310                1315                1320
Ala Gly Val Phe Ser Leu Glu Asp Gly Ile Lys Leu Ile Ala His
    1325                1330                1335
Arg Gly Lys Leu Met Gln Ala Leu Pro Gln Asn Gly Gln Met Val
    1340                1345                1350
Ala Val Leu Ser Asp Glu Val Thr Val Lys Lys Ala Ile Asn Ser
    1355                1360                1365
His His Gln Lys Val Val Ile Ala Ala Ile Asn Gly Glu Lys Ser
    1370                1375                1380
Leu Val Ile Ser Gly Glu His Gln Ala Val Ile Glu Val Thr Glu
    1385                1390                1395
Val Leu Lys Asn Gln Gly Ile Lys Thr Lys Pro Leu Thr Val Ser
    1400                1405                1410
His Ala Phe His Ser Pro Leu Met Gln Pro Met Leu Thr Glu Phe
    1415                1420                1425
Glu Arg Val Ala Gln Glu Ile Glu Tyr Ser Leu Pro Leu Ile Pro
    1430                1435                1440
Ile Val Ser Asn Val Thr Gly Asn Ile Ala Gly Glu Glu Met Ala
    1445                1450                1455
Thr Pro His Tyr Trp Val Asn His Val Val Asp Thr Val Gln Phe
    1460                1465                1470
Ala Ser Ser Met Lys Cys Leu Glu Lys Gln Gly Tyr Lys Val Phe
    1475                1480                1485
Leu Glu Ile Gly Ala Lys Pro Thr Leu Leu Gly Met Gly Arg Ser
    1490                1495                1500
Thr Leu Glu Ser Asp Pro Leu Asn Ser Asn Ser Ser Pro Tyr Leu
    1505                1510                1515
Trp Leu Pro Ser Leu Arg Pro Glu Gln Glu Asp Trp Gln Gln Ile
    1520                1525                1530
Leu Ser Ser Leu Ala Gln Leu Tyr Val Asn Gly Ile Trp Val Asp
    1535                1540                1545
Trp Ala Gly Phe Asp Gln Asp Tyr Pro Arg Gln Arg Val Ile Gly
    1550                1555                1560
Leu Pro Thr Tyr Pro Phe Asp Arg Gln Ser Tyr Trp Leu Thr Gln
    1565                1570                1575
Thr Pro Gln Leu Asn Ser His Gly Leu Tyr Gln Val Glu Trp Glu
    1580                1585                1590
Val Lys Gln Pro Ile Asn Asp Asn Phe Ser Leu Ile Asn Pro Ser
    1595                1600                1605
Thr Trp Leu Ile Leu Ala Asp Glu Gln Gly Leu Gly Glu Leu Leu
    1610                1615                1620
Gly Gln Glu Leu Glu Lys Leu Gly Gln Thr Cys Leu Leu Ile Tyr
    1625                1630                1635
Pro Glu Asn Gly Lys Gly Gln Lys Glu Thr Phe Glu Ser Leu Leu
    1640                1645                1650
```

```
Ala Glu Val Lys Gln Thr Gln Gln Thr Leu Gly Gly Ile Ile His
    1655            1660                1665

Leu Trp Ser Leu Asp Glu Val Thr Leu Thr Glu Ala Gln His Arg
    1670            1675                1680

Gly Cys Glu Ser Ile Leu Tyr Leu Leu Gln Thr Leu Tyr Glu Gln
    1685            1690                1695

Glu Ile Ser Ser Lys Val Trp Ile Ala Thr Arg Gly Thr Gln Arg
    1700            1705                1710

Val Thr Leu Gln Glu Asn Ser Leu Ser His Leu Gln Gly Thr Leu
    1715            1720                1725

Trp Gly Leu Ser Lys Val Val Ala Leu Glu Tyr Ser Gln Tyr Trp
    1730            1735                1740

Gly Gly Ile Ile Asp Leu Asp Pro Glu His Asp Pro Gln Glu Ala
    1745            1750                1755

Gln Phe Phe Leu Ser Glu Ile Phe Asn Ser Gln Lys Glu Thr Tyr
    1760            1765                1770

Leu Ala Phe Arg Lys Gly Gln Arg Tyr Val Thr Arg Leu Lys Lys
    1775            1780                1785

Ala Thr Leu Thr Pro Gln Lys Leu Ser Leu Tyr Gln Glu Gly Thr
    1790            1795                1800

Tyr Leu Ile Thr Gly Gly Leu Gly Ala Val Gly Leu Lys Val Ala
    1805            1810                1815

Gln Trp Leu Val Lys Glu Gly Ala Lys His Leu Val Leu Met Gly
    1820            1825                1830

Arg Ser Gln Pro Ser Ala Asn Ala Gln Glu Ile Leu Asn Thr Leu
    1835            1840                1845

Glu Glu Lys Gly Val Asn Leu Ser Ile Val Gln Gly Asp Val Thr
    1850            1855                1860

Glu Leu Glu Asp Ile Asn Arg Ile Phe Asn Gln Ile Lys Asn Ser
    1865            1870                1875

His Pro Pro Leu Lys Gly Ile Ile His Ala Ala Gly Leu Leu Lys
    1880            1885                1890

Asp Gly Ile Leu Gln Gly Leu Ser Trp Glu Ser Phe Gln Gln Val
    1895            1900                1905

Leu Ala Pro Lys Val Gln Gly Thr Trp Asn Leu His Gln Ala Ser
    1910            1915                1920

Leu Asp Leu Ser Leu Asp Phe Phe Val Met Phe Ser Ser Ala Ala
    1925            1930                1935

Ser Leu Leu Gly Ser Pro Gly Gln Gly Asn Tyr Ala Ala Ala Asn
    1940            1945                1950

Gly Phe Leu Asp Ala Phe Ala His Tyr Arg His Ser Leu Gly Leu
    1955            1960                1965

Pro Gly Leu Thr Ile Asn Trp Gly Ala Leu Ser Ala Gly Met Ala
    1970            1975                1980

Thr Ser Thr Arg Leu Gly Val Lys Gly Leu Glu Met Ile Glu Ile
    1985            1990                1995

Glu Ser Ala Leu Glu Met Leu Ser Ser Leu Leu Thr Thr Ser Thr
    2000            2005                2010

Pro Gln Val Gly Val Leu Ser Val Lys Trp Asp Ser Leu Ser Glu
    2015            2020                2025

Gln Phe Pro Asp Leu Leu Lys Thr Pro Phe Phe Gln Glu Val Ile
    2030            2035                2040

Ser Gln Asp Asn Lys Pro Ser His Glu His Ser Glu Ile Phe Thr
```

-continued

```
          2045                2050                2055
Thr Leu Leu Thr Leu Ser Pro Pro Gln Arg Thr Glu Val Leu Ile
          2060                2065                2070
Thr Tyr Leu Gln Ser Ser Ile Ala Arg Ile Leu His Leu Ser Pro
          2075                2080                2085
Ala Asp Ile Ser Pro Ser Asp Ser Leu Val Asp Leu Gly Met Asp
          2090                2095                2100
Ser Leu Met Val Met Glu Ala Ile Asn Thr Leu Lys Lys Asp Leu
          2105                2110                2115
Gln Leu Met Leu Tyr Pro Arg Glu Ile Tyr His Pro Lys Ile
          2120                2125                2130
Glu Ala Leu Ala Thr Tyr Leu Gly Thr Glu Phe Glu Gly Thr His
          2135                2140                2145
Gly Gln Ser Pro Lys Ser Pro Gln His Asn Pro Gln Lys Gln Glu
          2150                2155                2160
Leu Val Val Ser Arg Phe Ser Lys Thr Tyr Gln Pro Leu Thr Ile
          2165                2170                2175
Thr Lys Lys Leu Pro Gly Ile Ile Phe Ile Leu Ser Ser Pro Arg
          2180                2185                2190
Ala Gly Ser Thr Leu Leu Arg Val Met Phe Ala Gly His Pro Asp
          2195                2200                2205
Leu Ile Ser Pro Pro Glu Leu His Leu Leu Pro Phe Asn Thr Met
          2210                2215                2220
Gly Gln Arg Asp Gln Glu Leu Ala Leu Ser Tyr Leu Gly Glu Gly
          2225                2230                2235
Leu Gln Arg Ala Phe Met Glu Leu Gly Gly Leu Asp Ser Gln Thr
          2240                2245                2250
Ser Gln Ser Leu Ile Glu Glu Leu Ile His Gln Asn Thr Ser Ile
          2255                2260                2265
Pro Asp Val Tyr Gln Arg Leu Gln Glu Leu Ala Gly Asn Arg Leu
          2270                2275                2280
Leu Val Asp Lys Ser Pro Thr Tyr Gly Met Gln Arg Glu Ile Leu
          2285                2290                2295
Asp Arg Gly Glu Ala Met Phe Glu Gly Ala Lys Tyr Ile His Leu
          2300                2305                2310
Val Arg His Pro Tyr Ser Val Ile Asp Ser Phe Ser Arg Met Arg
          2315                2320                2325
Met Asp Lys Leu Val Gly Val Ser Gly Asp Asn Pro Tyr Ser Ile
          2330                2335                2340
Ala Glu Ser Val Trp Leu Glu Ser Asn Arg Asn Ile Leu Asp Phe
          2345                2350                2355
Ser Gln Thr Ile Asp Lys Glu Arg Tyr Tyr Gln Leu Arg Tyr Glu
          2360                2365                2370
Asp Leu Val Thr Gln Pro Ser Gln Met Met Arg Ser Leu Cys Glu
          2375                2380                2385
Phe Leu Asp Ile Pro Phe Asn Ser Ala Leu Leu Asp Pro Tyr Gln
          2390                2395                2400
Gly Asp Arg Met Thr Asp Gly Val Tyr Asn Gln Ser Ile Ser Val
          2405                2410                2415
Gly Asp Pro Asn Phe Ser Gln Arg Arg Gln Ile Asp Pro Lys Leu
          2420                2425                2430
Ala Asp Ala Trp Lys Lys Ile His Leu Pro Gln Pro Leu Gly Asp
          2435                2440                2445
```

```
Thr Thr Leu Arg Leu Ala Ala Ser Phe Asn Tyr Glu Leu Pro His
    2450                2455                2460

Glu Thr Val Leu Pro Ser Pro Pro Arg Gly Val Gly Gly Glu
    2465                2470                2475

Val Ile Ser Ile Pro Met Gln Glu Asn Tyr Leu Thr Ile Arg Gly
    2480                2485                2490

Leu Lys Leu Cys Leu Cys Ser Trp Gly Pro Glu Gly Glu Leu
    2495                2500                2505

Ile Leu Cys Ile His Gly Ile Leu Glu Gln Gly Ala Ala Trp Glu
    2510                2515                2520

Glu Val Ala Thr Arg Leu Ala Gln Lys Gly Tyr Arg Val Ile Ala
    2525                2530                2535

Pro Asp Leu Arg Gly His Gly Lys Ser Asp His Val Gly Asn Gly
    2540                2545                2550

Gly Ser Tyr Asn Leu Ile Asp Phe Leu Gly Asp Leu Asp Ala Ile
    2555                2560                2565

Ala Thr His Leu Thr Asp Lys Pro Phe Thr Leu Val Gly His Ser
    2570                2575                2580

Leu Gly Ser Ile Ile Ala Ala Met Phe Thr Ser Ile Arg Pro Glu
    2585                2590                2595

Lys Val Lys His Leu Val Leu Val Glu Thr Val Leu Pro Thr Glu
    2600                2605                2610

Val His Glu Gly Asp Thr Val Glu Gln Leu Ala Thr His Leu Asn
    2615                2620                2625

Tyr Leu Ser Ser Pro Pro Lys His Pro Val Phe Pro Asp Val Glu
    2630                2635                2640

Thr Ala Ala Lys Arg Leu Gln Thr Ala Thr Pro Ala Met Ser Glu
    2645                2650                2655

Gln Leu Ala Met Lys Leu Ala Lys Arg Ile Thr Gln Ala Gly Glu
    2660                2665                2670

Gly Gly Ile Gln Trp Arg Trp Asp Ser Leu Leu Arg Thr Arg Ala
    2675                2680                2685

Gly Ile Glu Phe Asn Gly Ile Asn Arg Ser Arg Tyr Leu Ser Leu
    2690                2695                2700

Leu Lys Gln Ile Gln Ala Lys Ile Thr Leu Ile Tyr Gly Asp Gln
    2705                2710                2715

Ser Asp Phe Asn Arg Pro Glu Asp Leu Gln Leu Gln Gln Gln Thr
    2720                2725                2730

Met Ser Gln Ala Asn Arg Ile Val Val Asn Gly Gly His Asn Leu
    2735                2740                2745

His Leu Glu Ala Phe Glu Leu Ala Asn Ile Ile Asn Gly
    2750                2755                2760

<210> SEQ ID NO 9
<211> LENGTH: 2775
<212> TYPE: PRT
<213> ORGANISM: Cyanothece sp.

<400> SEQUENCE: 9

Met Lys Arg Asn Phe Ser Asn Phe Val Asp Leu Leu Asn His Gln Ala
1               5                   10                  15

Glu Ala Gln Ser Asp Lys Thr Ile Phe Thr Phe Leu Gly Asp Gly Glu
                20                  25                  30

Ser Glu Thr Leu Ser Leu Thr Tyr Gln Gln Leu Asp Gln Gln Ala Arg
```

```
            35                  40                  45
Ala Ile Ala Val Gln Leu Gln Ser Leu Gln Ala Gly Glu Arg Ala
 50                  55                  60
Leu Leu Leu Tyr Gln Pro Gly Leu Glu Phe Ile Ser Ala Phe Phe Gly
 65                  70                  75                  80
Cys Leu Tyr Gly Gly Val Ile Pro Val Pro Ala Tyr Pro Pro Arg Ala
                     85                  90                  95
Asn Arg Ser Ile Glu Arg Leu Gln Ala Ile Val Ser Asp Ala Glu Ala
                    100                 105                 110
Lys Phe Ala Leu Thr Thr Gln Gly Ile Val Ser Thr Ile Glu Gly Lys
                    115                 120                 125
Leu Thr Gln Ser Gln Ile Ser Thr Glu Ala Ile Gln Cys Val Thr Thr
                    130                 135                 140
Asp Asn Leu Glu Leu Ser Leu Ser Asn Gln Trp Arg Arg Pro Asn Leu
145                 150                 155                 160
Lys Pro Asp Gln Leu Ala Phe Leu Gln Tyr Thr Ser Gly Ser Thr Gly
                    165                 170                 175
Asn Pro Lys Gly Val Met Val Ser His Gly Asn Leu Met His Asn Ala
                    180                 185                 190
Ala Leu Ile Asn Gly Tyr Phe Arg Asp Thr Pro Ser Ser Arg Gly Ala
                    195                 200                 205
Ser Trp Leu Pro Pro Tyr His Asp Met Gly Leu Ile Gly Gly Ile Leu
                    210                 215                 220
Gln Pro Ile Tyr Ala Asp Val Tyr Val Val Leu Met Pro Pro Val Thr
225                 230                 235                 240
Phe Leu Gln Arg Pro Leu Arg Trp Leu Glu Val Ile Ser Arg Tyr Arg
                    245                 250                 255
Ile Thr Thr Ser Gly Ala Pro Asn Phe Ala Tyr Glu Leu Cys Ala Thr
                    260                 265                 270
Gln Ile Thr Pro Glu Gln Arg Glu Asn Leu Asp Leu Ser Cys Trp Glu
                    275                 280                 285
Leu Ala Phe Ser Gly Ala Glu Pro Val Arg Ala Gln Thr Leu Ala Gln
                    290                 295                 300
Phe Ala Glu Ala Phe Ala Pro Cys Gly Phe Arg Lys Glu Ala Phe Tyr
305                 310                 315                 320
Pro Cys Tyr Gly Met Ala Glu Thr Thr Leu Ile Val Ser Gly Gly Thr
                    325                 330                 335
Arg Gly Val Tyr Pro Leu Leu Lys Asp Phe Asp Ala Lys Gly Ile Glu
                    340                 345                 350
Lys Asn Gln Val Ile Pro Ser Ser Pro Leu Glu Pro Asn Asn Leu Thr
                    355                 360                 365
Leu Val Ser Cys Gly Lys Ile Ser Gly Gly Gln Lys Val Ile Ile Val
                    370                 375                 380
Asn Pro Asp Thr Leu Lys Gln Cys Asp Asn Tyr Gln Ile Gly Glu Ile
385                 390                 395                 400
Trp Val Asn Ser Glu Ser Val Ala Lys Gly Tyr Trp Lys Arg Pro Gln
                    405                 410                 415
Leu Thr Glu Ala Ile Phe Asn Ala Tyr Thr Ala Asp Thr Gln Glu Gly
                    420                 425                 430
Pro Phe Leu Arg Thr Gly Asp Leu Gly Phe Leu Glu Asp Gly Glu Leu
                    435                 440                 445
Phe Val Thr Gly Arg Leu Lys Asp Leu Ile Ile Ile Arg Gly Arg Asn
450                 455                 460
```

```
His Tyr Pro Gln Asp Ile Glu Met Thr Ala Glu Lys Ser His Pro Ala
465                 470                 475                 480

Leu Arg Glu Ser Cys Gly Ala Ala Phe Ser Val Glu Val Gly Glu Glu
            485                 490                 495

Glu Arg Leu Val Ile Thr Tyr Val Lys Arg Ser Tyr Ile Arg Lys
        500                 505                 510

Leu Asn Val Glu Glu Val Thr Ser Ala Ile Arg Lys Ala Val Thr Gln
            515                 520                 525

Thr His Glu Leu Gln Pro Tyr Ala Ile Val Leu Leu Lys Thr Gly Ser
530                 535                 540

Ile Pro Lys Thr Ser Ser Gly Lys Ile Gln Arg His Ala Cys Lys Ala
545                 550                 555                 560

Glu Phe Leu Glu Gly Ser Leu Asn Ser Val Gly Gln Trp Ser Ala Ala
            565                 570                 575

Gln Thr Leu Pro Lys Thr Ser Lys Gln Leu Leu Glu Val Asn Ser Arg
            580                 585                 590

Lys Lys Arg Gly His Ile Ile Lys Ser Asn Pro Gln Gln Glu Ile Ile
            595                 600                 605

Glu Asn Trp Leu Val Thr Asn Ile Ala Gln Arg Leu Gly Leu Ser Pro
610                 615                 620

Thr Glu Ile Glu Ile Thr Glu Pro Phe Ala Ser Tyr Gly Leu Asp Ser
625                 630                 635                 640

Val Gln Ala Val Arg Ile Thr Ala Glu Leu Glu Asp Trp Leu Lys Val
                645                 650                 655

Lys Leu Ser Pro Thr Leu Ala Tyr Asp His Pro Thr Val Glu Ser Leu
            660                 665                 670

Ala Lys Tyr Leu Ala Ser Gly Thr Val Glu Thr Thr Leu Ala Thr Ser
        675                 680                 685

Lys Pro Leu Lys Thr Ser Ser Ser Val Ala Ile Ile Gly Met Ser Cys
        690                 695                 700

Arg Leu Pro Gly Ala Asn Ser Pro Asp Glu Phe Trp Gln Leu Leu Arg
705                 710                 715                 720

Gln Gly Lys Asp Gln Ile Thr Gln Val Asn Ala Arg Trp Asp Arg Asp
                725                 730                 735

Asp Trp Gly Gly Tyr Leu Lys Gly Val Asp Leu Phe Asp Ala Gln Phe
            740                 745                 750

Phe Gly Ile Ser Pro Arg Glu Ala Gln Glu Met Asp Pro Gln Gln Arg
            755                 760                 765

Leu Leu Leu Glu Val Ser Trp Glu Ala Leu Glu Lys Ala Ala Leu Ala
        770                 775                 780

Ala Asn Gln Leu Ala Gly Ser Asn Thr Gly Val Phe Ile Gly Ile Ser
785                 790                 795                 800

Ser His Asp Tyr Ser Gln Ile Arg Leu Lys Asn Ala Leu Glu Pro Ser
            805                 810                 815

Ala Tyr Ala Gly Thr Gly Asn Ala Ala Ser Ile Ala Ala Asn Arg Leu
            820                 825                 830

Ser Tyr Leu Tyr Asp Phe Arg Gly Pro Ser Leu Thr Val Asp Thr Ala
        835                 840                 845

Cys Ser Ser Ser Leu Val Ala Ile His Leu Ala Ile Lys Ser Leu Gln
        850                 855                 860

Ser Gly Glu Cys Gln Met Ala Leu Ala Gly Gly Val Asn Ile Leu Leu
865                 870                 875                 880
```

```
Ser Pro Glu Leu Ser Glu Thr Phe Thr Gln Ala Gly Met Met Ala Pro
            885                 890                 895
Asp Gly Arg Cys Lys Thr Phe Asp Glu Ser Ala Asp Gly Tyr Val Arg
            900                 905                 910
Gly Glu Gly Cys Gly Val Ile Val Leu Lys Ser Leu Glu Asp Ala Ile
            915                 920                 925
Arg Asp Gly Asp Pro Ile Leu Gly Val Ile His Gly Ser Ala Ile Asn
            930                 935                 940
Gln Asp Gly Arg Ser Asn Gly Leu Thr Ala Pro Asn Gly Ile Ala Gln
945                 950                 955                 960
Gln Gly Val Ile Arg Gln Ala Leu Met Asn Ala Gly Met Ser Ala Ala
            965                 970                 975
Asp Ile Ser Tyr Val Glu Thr His Gly Thr Gly Thr Ala Leu Gly Asp
            980                 985                 990
Pro Ile Glu Val Asn Ser Leu Lys Ser Val Leu Met Glu Gly Arg Ser
            995                 1000                1005
Glu Lys His Pro Leu Trp Leu Gly Ser Val Lys Thr Asn Ile Gly
        1010                1015                1020
His Leu Glu Ala Ala Ala Gly Ile Ala Gly Leu Ile Lys Val Leu
        1025                1030                1035
Leu Cys Leu Gln His Gln Glu Ile Pro Pro His Leu His Leu Tyr
        1040                1045                1050
Arg Leu Asn Ser His Ile Asn Leu Asp Asp Ser Pro Ile Ser Ile
        1055                1060                1065
Pro Thr Gln Leu Thr Pro Trp Lys Pro Glu Asn Arg Pro Arg Leu
        1070                1075                1080
Ala Gly Val Ser Ser Phe Gly Phe Gly Gly Thr Asn Ala His Ile
        1085                1090                1095
Ile Val Gly Glu Tyr Gln Asn Leu Ser Pro Thr Lys Arg Gly Gln
        1100                1105                1110
Val Glu Glu Leu Glu Arg Pro Leu His Ile Leu Thr Leu Ala Ala
        1115                1120                1125
Lys Arg Glu Lys Asp Leu Ser Ser Leu Val Lys Ser Tyr Gln His
        1130                1135                1140
Tyr Leu Thr Ala Phe Pro Ser Ala Ser Leu Glu Asp Ile Cys Phe
        1145                1150                1155
Thr Ala Asn Asn Gly Arg Thr Gln Phe Lys Asn Arg Leu Ala Ile
        1160                1165                1170
Ile Ala Gln Ser Arg Glu Gln Leu Ala Glu Lys Leu Ser Arg Gly
        1175                1180                1185
Glu Phe Ile Thr Pro Gln Ile Ala Gln Lys Leu Asn Pro Lys Ile
        1190                1195                1200
Ala Phe Leu Phe Thr Gly Gln Gly Ser Gln Tyr Ile Gly Met Gly
        1205                1210                1215
Tyr Gln Leu Tyr Gln Thr Gln Pro Thr Phe Arg Ala Ala Leu Asn
        1220                1225                1230
Thr Cys Ala Asp Leu Leu Glu Pro Tyr Leu Glu Tyr Pro Leu Leu
        1235                1240                1245
Glu Val Leu Tyr Pro Gln Glu Asn Ser Asn Leu Ala His Tyr Leu
        1250                1255                1260
Asp Gln Thr Ala Tyr Thr Gln Pro Ala Leu Phe Ala Leu Glu Tyr
        1265                1270                1275
Ala Leu Ala Gln Leu Trp Leu Ser Trp Gly Ile Glu Pro Ser Val
```

```
              1280            1285            1290
Val Met Gly His Ser Val Gly Glu Tyr Val Ala Ala Thr Leu Ala
    1295            1300            1305
Gly Val Phe Ser Leu Glu Asp Gly Leu Lys Leu Ile Ala His Arg
    1310            1315            1320
Gly Lys Leu Met Gln Ser Leu Pro Gln Asn Gly Gln Met Val Ala
    1325            1330            1335
Val Leu Ser Asp Glu Glu Thr Val Lys Lys Ala Ile Asn Ser His
    1340            1345            1350
Asp Glu Lys Val Val Ile Ala Ala Ile Asn Gly Glu Arg Asn Leu
    1355            1360            1365
Val Ile Ser Gly Glu Asn Gln Ala Ile Ile Glu Val Thr Asp Arg
    1370            1375            1380
Leu Thr His Gln Gly Ile Lys Thr Lys Pro Leu Gln Val Ser His
    1385            1390            1395
Ala Phe His Ser Pro Leu Met Gln Pro Met Leu Glu Glu Phe Ala
    1400            1405            1410
Ser Ile Ala Arg Glu Val Glu Tyr Ser Leu Pro Gln Ile Pro Leu
    1415            1420            1425
Val Ser Asn Val Ser Gly Asn Leu Ala Ala Glu Ala Ile Ala Thr
    1430            1435            1440
Pro Glu Tyr Trp Val Asn His Val Ile Asn Pro Val His Phe Ser
    1445            1450            1455
Pro Ser Ile Lys Leu Met Glu Ser Lys Gly Tyr Gln Ile Phe Leu
    1460            1465            1470
Glu Ile Gly Ala Lys Pro Thr Leu Leu Gly Met Gly Arg Ser Ile
    1475            1480            1485
Ile Glu Ser Asp Ser Ser Val Asn His Gln Asn Ala Tyr Leu Trp
    1490            1495            1500
Leu Pro Ser Leu Arg Pro Gly Gln Ser Asp Trp Gln Gln Met Leu
    1505            1510            1515
Thr Ser Leu Ala Gln Leu Tyr Val Gln Gly Ile Asn Ile Asp Trp
    1520            1525            1530
Ala Gly Phe Glu Ala Asp Tyr Gln Arg Gln Arg Met Gly Gly Leu
    1535            1540            1545
Pro Thr Tyr Pro Phe Glu Arg Gln Arg Tyr Trp Leu Lys Pro Glu
    1550            1555            1560
Leu Glu Ile His Thr Gly Thr Lys Arg Leu Thr Thr Glu Gln Val
    1565            1570            1575
Ser Pro Pro Asn Gln Asp Trp Leu Tyr Gln Val Val Trp Glu Ala
    1580            1585            1590
Lys Pro Ile Asn Pro His Gln Leu Ser Asn Gln Lys Thr Ser Thr
    1595            1600            1605
Trp Leu Ile Phe Gly Asp Gln Gly Leu Ala Lys Thr Val Ala
    1610            1615            1620
Glu Gln Leu Glu Lys Leu Gly Lys Thr Ser Leu Leu Val Gln Ser
    1625            1630            1635
Asp Lys Gly Asp Lys Asn Gly Asn His Lys Thr Leu Asn Pro Thr
    1640            1645            1650
Glu Lys Asn Asp Phe Gln Arg Leu Leu Thr Pro Phe Lys Thr Ser
    1655            1660            1665
Gly Glu Ser Leu Glu Gly Ile Ile Tyr Leu Trp Ser Leu Glu Glu
    1670            1675            1680
```

```
Asp Glu Ile Ser Lys Ser Asn Pro Gln Ser Ile Leu Tyr Leu Leu
1685                1690                1695

Gln Thr Leu Tyr Glu Gln Asn Leu Ser Ser Arg Leu Trp Ile Ala
1700                1705                1710

Thr Arg Gly Ile Gln Pro Val Thr Thr Glu Asp Leu Ala Ala Pro
1715                1720                1725

His Ile Pro Leu Gln Gly Met Leu Trp Gly Leu Gly Lys Val Ile
1730                1735                1740

Ala Leu Glu Tyr Ser Asp Tyr Trp Gly Gly Leu Ile Asp Ile Gly
1745                1750                1755

Thr Gln Pro His Thr Asp Glu Ala Lys Leu Leu Leu Ser Ala Ile
1760                1765                1770

Ile Asn Pro Asp Gly Glu Gln Tyr Leu Ala Phe Arg Asp Gly Gln
1775                1780                1785

Arg Tyr Val Ala Arg Ile Asp Lys Ala Glu Ile Lys Pro Lys Lys
1790                1795                1800

Phe Ser Ile Asp Glu Asn Gly Ser Tyr Leu Ile Thr Gly Gly Leu
1805                1810                1815

Gly Ala Val Gly Leu Lys Val Ala Gln Trp Leu Ala Lys Ala Gly
1820                1825                1830

Ala Lys His Leu Ile Leu Met Gly Arg Ser His Pro Thr Ala Asn
1835                1840                1845

Ala Gln Glu Thr Ile Lys His Leu Glu Lys Gln Gly Ile Glu Ile
1850                1855                1860

Ile Ile Ala Gln Ala Asp Val Thr Arg Gln Glu Asp Ile Asp Arg
1865                1870                1875

Val Phe Asn Gln Ile Lys Thr Pro Leu Lys Gly Ile Ile His Ala
1880                1885                1890

Ala Gly Leu Leu Asp Asp Gly Ile Leu Gln Gly Leu Ser Trp Glu
1895                1900                1905

Lys Phe Lys Lys Val Leu Ala Pro Lys Val Glu Gly Thr Trp Asn
1910                1915                1920

Leu His Lys Ala Ser Leu Asn His Pro Leu Asp Phe Phe Val Met
1925                1930                1935

Phe Ser Ser Ala Ala Ser Leu Phe Gly Ser Pro Gly Gln Gly Asn
1940                1945                1950

Tyr Ala Ala Ala Asn Gly Phe Leu Asp Gly Met Ala Tyr Tyr Arg
1955                1960                1965

Gln Ser Gln Gly Leu Pro Ala Leu Thr Val Asn Trp Gly Ala Leu
1970                1975                1980

Ser Gly Gly Met Ala Lys Ala Thr Arg Leu Ala Val Lys Gly Leu
1985                1990                1995

Asp Leu Ile Asp Ile Glu Pro Ala Leu Asp Ile Leu Ser His Leu
2000                2005                2010

Leu Ala Asp Lys Ile Ala Gln Ile Gly Val Val Ser Val Asp Trp
2015                2020                2025

Glu Thr Leu Ala Gln Gln Phe Pro Gln Leu Arg Gln Ser Pro Tyr
2030                2035                2040

Phe Gln Arg Val Ile Thr Gln Leu Ser Pro Glu Gln Val Lys Pro
2045                2050                2055

Asp His Ser Gln Ser Gln Ile Leu Ala Asn Leu Leu Ala Leu Ser
2060                2065                2070
```

```
Pro Glu Gln Arg Thr Glu Ala Leu Thr Ala Tyr Leu Gln Ser Ala
2075                2080                2085

Met Ala Gln Ile Met Gln Leu Ser Pro Ser Gln Ile Ser Gly Glu
2090                2095                2100

Asp Ser Leu Leu Asp Ile Gly Met Asp Ser Leu Met Ile Met Glu
2105                2110                2115

Ala Ile Asn Gln Leu Lys Arg Asp Leu Gln Leu Met Leu Tyr Pro
2120                2125                2130

Arg Glu Ile Tyr Gln His Pro Lys Ile Glu Ala Leu Ala Asn Tyr
2135                2140                2145

Leu Ala Ala Glu Phe Glu Arg Thr His Gly Lys Gly Gln Ile Pro
2150                2155                2160

Val Thr Ser Lys Gln Glu Leu Val Val Ser Arg Leu Thr Ile Ala
2165                2170                2175

Asn Gln Pro Leu Thr Ile Thr Lys Lys Leu Pro Gly Ile Leu Phe
2180                2185                2190

Ile Leu Ser Ser Pro Arg Ala Gly Ser Thr Leu Leu Arg Val Met
2195                2200                2205

Leu Ala Gly His Pro Asp Leu Ala Ser Pro Pro Glu Leu His Leu
2210                2215                2220

Leu Pro Phe Asn Ser Met Gly Gln Arg Asn Gln Glu Leu Ala Leu
2225                2230                2235

Ser Tyr Leu Gly Glu Gly Leu Gln Arg Ala Phe Met Asp Leu Gln
2240                2245                2250

Gly Leu Asp Ser Ala Thr Ser Gln Gln Leu Ile Glu Arg Leu Ile
2255                2260                2265

Ala Glu Asp Ile Ser Ile Pro Asp Val Tyr Glu Met Leu Gln Gln
2270                2275                2280

Ser Ala Gly Lys Arg Leu Leu Val Asp Lys Ser Pro Thr Tyr Gly
2285                2290                2295

Met Gln Arg Glu Ile Leu Asp Arg Ala Glu Ala Ile Phe Glu Gly
2300                2305                2310

Ala Lys Tyr Ile His Leu Val Arg His Pro Tyr Pro Val Ile Asp
2315                2320                2325

Ser Phe Cys Arg Met Arg Met Asp Lys Leu Val Gly Ser Glu Gly
2330                2335                2340

Asp Asn Pro Tyr Gln Leu Ala Glu Ser Ile Trp Trp Glu Ser Asn
2345                2350                2355

Arg Asn Ile Ile Glu Phe Ser Lys Thr Ile Ser Ser Asp Arg Tyr
2360                2365                2370

Tyr Gln Leu Arg Tyr Glu Asp Leu Val Thr Gln Pro Ser Gln Ala
2375                2380                2385

Met Gln Ala Leu Cys Glu Phe Leu Asp Ile Pro Phe Asp Ser Ala
2390                2395                2400

Leu Leu Asp Pro Tyr Gln Gly Gln Arg Met Thr Asp Gly Val Tyr
2405                2410                2415

Asn Gln Ser Met Ser Val Gly Asp Pro Asn Phe Ser Lys Arg Lys
2420                2425                2430

Gln Ile Asp Pro Lys Leu Ala Asp Ala Trp Lys Asp Ile Gln Leu
2435                2440                2445

Pro His Pro Leu Gly Asp Asn Thr Arg Gln Leu Ala Ile Ser Leu
2450                2455                2460

Asn Tyr Pro Leu Pro His Gln Asn Ile Pro Pro Leu Leu Arg Gly
```

-continued

```
              2465                    2470                    2475
Glu  Gly  Gly  Ile  Thr  Glu  Glu  Val  His  Leu  Glu  Glu  Glu  Tyr  Ile
       2480                    2485                    2490

Asn  Ile  Arg  Gly  Leu  Asn  Leu  Cys  Leu  Cys  Ser  Trp  Gly  Pro  Lys
       2495                    2500                    2505

Gln  Gly  Glu  Leu  Ile  Leu  Cys  Val  His  Gly  Ile  Leu  Glu  Gln  Gly
       2510                    2515                    2520

Ala  Ala  Trp  Gly  Gln  Met  Ala  Thr  Arg  Leu  Ala  Gly  Leu  Gly  Tyr
       2525                    2530                    2535

Arg  Val  Val  Ala  Pro  Asp  Leu  Arg  Gly  Gln  Gly  Lys  Ser  Asp  His
       2540                    2545                    2550

Val  Gly  Lys  Gly  Gly  Ser  Tyr  Asn  Leu  Ile  Asp  Phe  Leu  Ala  Asp
       2555                    2560                    2565

Leu  Asp  Ala  Ile  Ala  Asn  Ser  Leu  Thr  Asp  Gln  Pro  Phe  Thr  Leu
       2570                    2575                    2580

Val  Gly  His  Ser  Leu  Gly  Ser  Ile  Ile  Ala  Ala  Met  Phe  Thr  Ser
       2585                    2590                    2595

Ile  Arg  Pro  Glu  Lys  Val  Lys  Asn  Leu  Val  Leu  Val  Glu  Thr  Val
       2600                    2605                    2610

Leu  Pro  Thr  Glu  Val  Ser  Gln  Thr  Asp  Ala  Val  Glu  Gln  Leu  Ala
       2615                    2620                    2625

Thr  His  Leu  Asn  Tyr  Leu  Ala  Ser  Pro  Pro  Glu  His  Pro  Val  Phe
       2630                    2635                    2640

Pro  Asp  Val  Glu  Thr  Ala  Ala  Lys  Arg  Leu  Gln  Thr  Ala  Thr  Pro
       2645                    2650                    2655

Ala  Met  Ser  Glu  Ala  Leu  Ala  Ile  Ser  Leu  Ala  Lys  Arg  Ile  Thr
       2660                    2665                    2670

Glu  Pro  Cys  Glu  Gly  Gly  Ile  Arg  Trp  Arg  Trp  Asp  Ser  Leu  Leu
       2675                    2680                    2685

Arg  Thr  Arg  Ala  Gly  Ile  Glu  Phe  Asn  Gly  Ile  Asn  Arg  Ser  Arg
       2690                    2695                    2700

Tyr  Ile  Ser  Leu  Leu  Glu  Gln  Ile  Gln  Ala  Pro  Ile  Thr  Leu  Ile
       2705                    2710                    2715

Tyr  Gly  Asp  Asn  Ser  Asp  Phe  Asn  Arg  Pro  Glu  Asp  Leu  Gln  Ala
       2720                    2725                    2730

Gln  Gln  Lys  Ala  Met  Ser  Ala  Ala  Lys  Arg  Ile  Ile  Leu  Lys  Gly
       2735                    2740                    2745

Gly  His  Asn  Leu  His  Leu  Asp  Ala  Tyr  Glu  Gln  Leu  Ala  Asn  Ile
       2750                    2755                    2760

Ile  Lys  Gln  Ile  Leu  Gly  Lys  Thr  Gly  Gln  Ser  Phe
       2765                    2770                    2775
```